US006599728B2

(12) United States Patent
Morin et al.

(10) Patent No.: US 6,599,728 B2
(45) Date of Patent: Jul. 29, 2003

(54) SECOND MAMMALIAN TANKYRASE

(75) Inventors: Gregg B. Morin, Davis, CA (US); Walter D. Funk, Hayward, CA (US); Mieczyslaw A. Piatyszek, Morgan Hill, CA (US)

(73) Assignee: Geron Corporation, Menlo Park, CA (US)

( * ) Notice: Subject to any disclaimer, the term of this patent is extended or adjusted under 35 U.S.C. 154(b) by 0 days.

(21) Appl. No.: 09/972,115

(22) Filed: Oct. 5, 2001

(65) Prior Publication Data

US 2003/0032769 A1 Feb. 13, 2003

Related U.S. Application Data

(63) Continuation of application No. PCT/US00/09558, filed on Apr. 10, 2000.

(60) Provisional application No. 60/128,577, filed on Apr. 9, 1999, and provisional application No. 60/129,123, filed on Apr. 13, 1999.

(51) Int. Cl.$^{7}$ .......................... C12N 9/12; C12N 9/00; C12N 5/00; A61K 38/16; C07H 21/04

(52) U.S. Cl. ....................... 435/194; 435/183; 435/325; 530/358; 536/23.1

(58) Field of Search ................................ 435/194, 183, 435/325; 530/358; 536/23.1

(56) References Cited

U.S. PATENT DOCUMENTS 6,277,613 B1 8/2001 De Lange et al.
6,455,290 B1 * 9/2002 Berthelsen et al. ......... 435/194

FOREIGN PATENT DOCUMENTS

WO WO 99/15647 4/1999
WO WO 99/64606 12/1999
WO WO 01/00849 A1 1/2001
WO WO 01/04326 A1 1/2001
WO WO 01/30987 A2 5/2001

OTHER PUBLICATIONS

Ame et al., PARP–2, A novel mammalian DNA damage–dependent poly (ADP–ribose) polymerase, J. Biol. Chem. 274:17860, 1999.

Bennett et al., Ankyrins. Adaptors between diverse plasma membrane proteins and the cytoplasm, J. Biol. Chem. 267:8703, 1992.

Bianchi et al., TRF1 binds a bipartite telomeric site with extreme spatial flexibility, EMBO J. 18:5735, 1999.

Bodnar et al., Extension of life–span by introduction of telomerase into normal human cells , Science 279:349, 1998.

Bork et al., Hundreds of ankyrin–like repeats in functionally diverse proteins: mobile modules that cross phyla horizontally?, Proteins: Structure, Function & Genetics 17:363, 1993.

Broccoli et al., Human telomeres contain two distinct Myb–related proteins TRF1 and TRF2, Nature Genetics 17:231, 1997.

(List continued on next page.)

*Primary Examiner*—Hankyel T. Park
(74) *Attorney, Agent, or Firm*—J. Michael Schiff; David J. Earp

(57) ABSTRACT

A new protein named Tankyrase II is described in this disclosure. Sequences for the human Tankyrase II cDNA and the protein translation product are provided. Also provided are species homologs, muteins, related nucleic acids, peptides, and drug screening assays. Tankyrase II interacts with telomere-associated proteins, thereby affecting telomerase activity and potentially telomere length. The materials and techniques provided in this disclosure allow Tankyrase II activity to be studied in vitro and manipulated inside cells—to the potential benefit of clinical conditions associated with a defect in telomerase activity, or the replicative capacity of affected cells.

22 Claims, 18 Drawing Sheets

OTHER PUBLICATIONS

Brown et al., Sorting proteins to their target membranes, Kidney Intl. 57:816, 2000.
Chi et al, Tankyrase is a golgi–associated mitogen–activated protein kinase substrate that interacts with IRAP in GLUT4 visicles, J. Biol. Chem. 275–38437, 2000.
Chi et al, The primordial high energy compound: ATP or inorganic pyrophosphate?, J. Biol. Chem. 275:35677, 2000.
de Murcia et al., Poly (ADP–ribose) polymerase: a molecular nick–sensor, TIBS 19:172, 1994.
Griffith et al., TRF1 promotes parallel pairing of telomeric tracts in vitro, J. Mol. Biol. 278:79, 1998.
Griffith et al, Mammalian telomeres end in a large duplex loop, Cell 97:503, 1999.
Harley et al., Telomeres and telomerase in aging and cancer, Curr. Opin. Genet. Dev. 5:249, 1995.
Jeggo, P.A., DNA repair: PARP—another guardian angel?, Current Biol. 8:R49, 1998.
Kaminker et al., Tank2, a new trf1–associated poly(adp–ribose) polymerase, causes rapid induction of cell death upon overexpression, J. Biol. Chem. 276:35891, 2001.
Karlseder et al., p53– and ATM–dependent apoptosis induced by telomeres lacking TRF2, Science 283:1321, 1999.
Kickhoefer, J., The 193–kD vault protein, VPARP, is a novel poly(ADP–ribose) polymerase, Cell Biol. 146:917, 1999.
Kim et al., TIN2, a new regulator of telomere length in human cells, Nature Genetics 23:405, 1999.
Konig et al., Sequence–specific DNA recognition by the Myb–like domain of the human telomere binding protein TRF1: a model for the protein–DNA complex, Nucleic Acids Res. 26:1731, 1998.
Kuimov et al., Cloning and characterization of TNKL, a member of tankyrase gene family, Genes Immun. 2:52, 2001.
Kyba et al., The SAM domain of polyhomeotic, RAE28, and Scm mediates specific interactions through conserved residues, Dev. Genetics 22:74 (1998).
Lamb et al., Neural induction by the secreted polypeptide noggin, Science 262:713 (1993).
Lim et al., Noggin antagonizes BMP signaling to create a niche for adult neurogenesis, Neuron 28:713 (2000).
Lindahl et al., Post–translational modification of poly (ADP–Ribose) polymerase induced by DNA strand breaks, TIBS 20:405 (1995).
Lyons, Identification of a novel human tankyrase through its interaction with the adaptor protein Grb14J, Biol. Chem. 276:17172, 2001.
Michaely et al., The ANK Repeat: a Ubiq2uitous Motif involved in Macromolecular Recognition, TICB, 2:127, 1992.
Michaely et al., Mechanism for binding site diversity on ankyrin. J. Biol. Chem, 270:31298, 1995.
Monz et al., Novel Tankyrase–related gene detected with meningioma–specific sera, Clin. Cancer Res. 7:113, 2001.
Pennisi, A possible new partner for telomerase, Science 282:1395 (1998).
Ponting, SAM: a novel motif in yeast sterile and *drosophila* polyhomeotic proteins, Protein Science 4:1928 (1995).
Rolli et al., Random Mutageneses of the Poly (ADP–ribose) Polymerase Catalytic Domain Reveals Amino Acids Involved in Polymer Branching, Biochemistry 36 :12147, 1997.
Sasai et al., Regulationof neural induction by the Chd and Bmp–4 antagonistic patterning signals in *Xenopus*, Nature 376:333 (1995).
Sallmann et al., Rapid detection of poly(ADP–ribose) polymerase by enzyme–linked immunosorbent assay during its purification and improvement of its purification, Mol Cell Biochem. 185:199, 1998.
Simonin et al., Identification of Potential Active–site Residues in the Human Poly (ADP–ribose) Polymerase, J Biol Chem. 268:8529 1993.
Smith et al., Tankyrase promotes telomere elongation in human cells, Curr. Biol. 10:1299, 2000.
Smith et al., Cell cycle dependent localization of the telomeric PARP, tankyrase, to nuclear pore complexes and centrosomes, J. Cell Sci. 112:3649, 1999.
Smith et al., Tankyrase, a poly(ADP–ribose) polymerase at human telomeres, Science 282:1484, 1998.
Smogorzewska et al., Control of human telomere length by TRF1 and TRF2, Mol. Cellular Biol. 20:000, 2000.
Stapleton et al., The crystal structure of an Eph receptor SAM domain reveals a mechanism for modular dimerization, Nature Struct. Biol. 6:44, 1999.
Still et al., Identification of a novel gene (ADPRTL1) encoding a potential Poly(ADP–ribosyl)transferase protein, Genomics 62:533, 1999.
Thanos et al., Oligomeric structure of the human EphB2 receptor SAM domain, Science 283: 833, 1999.
van Steensel et al., TRF2 protects human telomeres from end–to–end fusions, Cell 92:401, 1998.
Zhu et al., Chromosomal mapping of the tankyrase gene in human and mouse, Genomics. 1999 Genomics, 57:320.
Ziegler et al., A cellular survival switch: poly(ADP–ribosyl)ation stimulates DNA repair and silences transcription, Bioessays 23:543, 2001.
GenBank Accession No. AF309033, *Homo Sapiens* Tankyrase–2 (TNKS–2) mRNA, complete cds.
GenBank Accession No. XM 051724, *Homo Sapiens* Similar to Tankyrase 2 (*H. Sapiens*)(LOC94771), mRNA.

* cited by examiner

Figure 2(A)

```
    NNNNNNNNNNNNNNNNNNNNNNNNNNNNNNNNNNNNNNNNNNNNNNNNNNNNNNNNNNNN
  1 ---------+---------+---------+---------+---------+---------+ 60
    ?  ?  ?  ?  ?  ?  ?  ?  ?  ?  ?  ?  ?  ?  ?  ?  ?  ?  ?  ?   -

    NNNNNNNNNNNNNNNNNNNNNNNNNNNNNNNNNNNNNNNNNNNNNNNNNNNNNNNNNNNN
 61 ---------+---------+---------+---------+---------+---------+ 120
    ?  ?  ?  ?  ?  ?  ?  ?  ?  ?  ?  ?  ?  ?  ?  ?  ?  ?  ?  ?   -

    NNNNNNNNNNNNNNNNNNNNNNNNNNNNNNNNNNNNNNNNNNNNNNNNNNNNNNNNNNNN
121 ---------+---------+---------+---------+---------+---------+ 180
    ?  ?  ?  ?  ?  ?  ?  ?  ?  ?  ?  ?  ?  ?  ?  ?  ?  ?  ?  ?   -

    NNNNNNNNNNNNNNNNNNNNNNNNNNNNNNNNNNNNNNNNNNNNNNNNNNNNNNNNNNNN
181 ---------+---------+---------+---------+---------+---------+ 240
    ?  ?  ?  ?  ?  ?  ?  ?  ?  ?  ?  ?  ?  ?  ?  ?  ?  ?  ?  ?   -

    NNNNNNNNNNNNNNNNNNNNNNNNNNNNNNNNNNNNNNNNNNNNNNNNNNNNNNNNNNNN
241 ---------+---------+---------+---------+---------+---------+ 300
    ?  ?  ?  ?  ?  ?  ?  ?  ?  ?  ?  ?  ?  ?  ?  ?  ?  ?  ?  ?   -

    NNNNNNNNNNNNNNNNNNNNNNNNNNNNNNNNNNNNNNNNNNNNNNNNNNNNNNNNNNNN
301 ---------+---------+---------+---------+---------+---------+ 360
    ?  ?  ?  ?  ?  ?  ?  ?  ?  ?  ?  ?  ?  ?  ?  ?  ?  ?  ?  ?   -

    NNNNNNNNNNNNNNNNNNNNNNNNNNNNNNNNNNNNNNNNNNNNNNNNNNNNNNNNNNNN
361 ---------+---------+---------+---------+---------+---------+ 420
    ?  ?  ?  ?  ?  ?  ?  ?  ?  ?  ?  ?  ?  ?  ?  ?  ?  ?  ?  ?   -

    NNNNNNNNNNNNNNNNNNNNNNNNNNNNNNNNNNNNNNNNNNNNNNNNNNNNNNNNNNNN
421 ---------+---------+---------+---------+---------+---------+ 480
    ?  ?  ?  ?  ?  ?  ?  ?  ?  ?  ?  ?  ?  ?  ?  ?  ?  ?  ?  ?   -

                                                          <-|-> ANK
    NNNNNNNNNNNNNNNNNNNNNNNNNNNNNNNNNNNNNNNNNNNNNNNNNNNNNNNNNNNN
481 ---------+---------+---------+---------+---------+---------+ 540
    ?  ?  ?  ?  ?  ?  ?  ?  ?  ?  ?  ?  ?  ?  ?  ?  ?  ?  ?  ?   -

    NNNNNNNNNNNNNNNNNNNNNNNNNNNNNNNNNNNNNNNNNNNNNNAACCATTCCNNAGG
541 ---------+---------+---------+---------+---------+---------+ 600
    ?  ?  ?  ?  ?  ?  ?  ?  ?  ?  ?  ?  ?  ?  ?  ?  P  F  ?  R   -

    CTGGTGACCCCTGAAAAGGTNAACANCCNCAACACGGNGGGCAGGAAATCCACCCCGCTG
601 ---------+---------+---------+---------+---------+---------+ 660
    L  V  T  P  E  K  V  N  ?  ?  N  T  ?  G  R  K  S  T  P  L   -

    CACTTCCCCGCAGGTTTTGGGCGGAAAAACCTNNTTAAATATTTGCTTCAAAATGGTGCA
661 ---------+---------+---------+---------+---------+---------+ 720
    H  F  P  A  G  F  G  R  K  N  L  ?  K  Y  L  L  Q  N  G  A   -

    AATNTCCAANCACTTTATAATGGGGGCCTTATTCCTCTTCATANTGCATGCTCTTTTGGT
721 ---------+---------+---------+---------+---------+---------+ 780
    N  ?  Q  ?  L  Y  N  G  G  L  I  P  L  H  ?  A  C  S  F  G   -

    CATGCTAAAANTATCAATCTCCTTTTGCGACATGGTGCAGACCCCAATGCTCGAGATAAT
781 ---------+---------+---------+---------+---------+---------+ 840
```

Figure 2(B)

```
              H  A  K  ?  I  N  L  L  L  R  H  G  A  D  P  N  A  R  D  N    -
      TGGAATTATACTCCTCTCCATGAAGCTGCAATTAAAGGAAAGATTGATGTTTGCATTGTG
 841  ------------+---------+---------+---------+---------+---------+  900
      W  N  Y  T  P  L  H  E  A  A  I  K  G  K  I  D  V  C  I  V    -

      CTGTTACAGCATGGAGCTGAGCCAACCATCCGAAATACAGATGGAAGGACAGCATTGGAT
 901  ------------+---------+---------+---------+---------+---------+  960
       L  L  Q  H  G  A  E  P  T  I  R  N  T  D  G  R  T  A  L  D   -

      TTAGCAGATCCATCTGCCAAAGCAGTGCTTACTGGTGAATATAAGAAAGATGAACTCTTA
 961  ------------+---------+---------+---------+---------+---------+  1020
       L  A  D  P  S  A  K  A  V  L  T  G  E  Y  K  K  D  E  L  L   -

      GAAAGTGCCAGGAGTGGCAATGAAGAAAAAATGATGGCTCTACTCACACCATTAAATGTC
1021  ------------+---------+---------+---------+---------+---------+  1080
       E  S  A  R  S  G  N  E  E  K  M  M  A  L  L  T  P  L  N  V   -

      AACTGCCACGCAAGTGATGGCAGAAAGTCAACTCCATTACATTTGGCAGCAGGATATAAC
1081  ------------+---------+---------+---------+---------+---------+  1140
       N  C  H  A  S  D  G  R  K  S  T  P  L  H  L  A  A  G  Y  N   -

      AGAGTAAAGATTGTACAGCTGTTACTGCAACATGGAGCTGATGTCCATGCTAAAGATAAA
1141  ------------+---------+---------+---------+---------+---------+  1200
       R  V  K  I  V  Q  L  L  L  Q  H  G  A  D  V  H  A  K  D  K   -

      GGTGATCTGGTACCATTACACAATGCCTGTTCTTATGGTCATTATGAAGTAACTGAACTT
1201  ------------+---------+---------+---------+---------+---------+  1260
       G  D  L  V  P  L  H  N  A  C  S  Y  G  H  Y  E  V  T  E  L   -

      TTGGTCAAGCATGGTGCCTGTGTAAATGCAATGGACTTGTGGCAATTCACTCCTCTTCAT
1261  ------------+---------+---------+---------+---------+---------+  1320
       L  V  K  H  G  A  C  V  N  A  M  D  L  W  Q  F  T  P  L  H   -

      GAGGCAGCTTCTAAGAACAGGGTTGAAGTATGTTCTCTTCTCTTAAGTTATGGTGCAGAC
1321  ------------+---------+---------+---------+---------+---------+  1380
       E  A  A  S  K  N  R  V  E  V  C  S  L  L  L  S  Y  G  A  D   -

      CCAACACTGCTCAATTGTCACAATAAAAGTGCTATAGACTTGGCTCCCACACCACAGTTA
1381  ------------+---------+---------+---------+---------+---------+  1440
       P  T  L  L  N  C  H  N  K  S  A  I  D  L  A  P  T  P  Q  L   -

      AAAGAAAGATTAGCATATGAATTTAAAGGCCACTCGTTGCTGCAAGCTGCACGAGAAGCT
1441  ------------+---------+---------+---------+---------+---------+  1500
       K  E  R  L  A  Y  E  F  K  G  H  S  L  L  Q  A  A  R  E  A   -

      GATGTTACTCGAATCAAAAAACATCTCTCTCTGGAAATGGTGAATTTCAAGCATCCTCAA
1501  ------------+---------+---------+---------+---------+---------+  1560
       D  V  T  R  I  K  K  H  L  S  L  E  M  V  N  F  K  H  P  Q   -

      ACACATGAAACAGCATTGCATTGTGCTGCTGCATCTCCATATCCCAAAAGAAAGCAAATA
1561  ------------+---------+---------+---------+---------+---------+  1620
       T  H  E  T  A  L  H  C  A  A  A  S  P  Y  P  K  R  K  Q  I   -

      TGTGAACTGTTGCTAAGAAAAGGAGCAAACATCAATGAAAAGACTAAAGAATTCTTGACT
1621  ------------+---------+---------+---------+---------+---------+  1680
       C  E  L  L  L  R  K  G  A  N  I  N  E  K  T  K  E  F  L  T   -
```

Figure 2(C)

```
     CCTCTGCACGTGGCATCTGAGAAAGCTCATAATGATGTTGTTGAAGTAGTGGTGAAACAT
1681 ---------+---------+---------+---------+---------+---------+ 1740
     P  L  H  V  A  S  E  K  A  H  N  D  V  V  E  V  V  V  K  H   -

     GAAGCAAAGGTTAATGCTCTGGATAATCTTGGTCAGACTTCTCTACACAGAGCTGCATAT
1741 ---------+---------+---------+---------+---------+---------+ 1800
     E  A  K  V  N  A  L  D  N  L  G  Q  T  S  L  H  R  A  A  Y   -

     TGTGGTCATCTACAAACCTGCCGCCTACTCCTGAGCTATGGGTGTGATCCTAACATTATA
1801 ---------+---------+---------+---------+---------+---------+ 1860
     C  G  H  L  Q  T  C  R  L  L  L  S  Y  G  C  D  P  N  I  I   -

     TCCCTTCAGGGCTTTACTGCTTTACAGATGGGAAATGAAAATGTACAGCAACTCCTCCAA
1861 ---------+---------+---------+---------+---------+---------+ 1920
     S  L  Q  G  F  T  A  L  Q  M  G  N  E  N  V  Q  Q  L  L  Q   -

     GAGGGTATCTCATTAGGTAATTCAGAGGCAGACAGACAATTGCTGGAAGCTGCAAAGGCT
1921 ---------+---------+---------+---------+---------+---------+ 1980
     E  G  I  S  L  G  N  S  E  A  D  R  Q  L  L  E  A  A  K  A   -

     GGAGATGTCGAAACTGTAAAAAAACTGTGTACTGTTCAGAGTGTCAACTGCAGAGACATT
1981 ---------+---------+---------+---------+---------+---------+ 2040
     G  D  V  E  T  V  K  K  L  C  T  V  Q  S  V  N  C  R  D  I   -

     GAAGGGCGTCAGTCTACACCACTTCATTTTGCAGCTGGGTATAACAGAGTGTCCGTGGTG
2041 ---------+---------+---------+---------+---------+---------+ 2100
     E  G  R  Q  S  T  P  L  H  F  A  A  G  Y  N  R  V  S  V  V   -

     GAATATCTGCTACAGCATGGAGCTGATGTGCATGCTAAAGATAAAGGNGGCCTTGTACCT
2101 ---------+---------+---------+---------+---------+---------+ 2160
     E  Y  L  L  Q  H  G  A  D  V  H  A  K  D  K  G  G  L  V  P   -

     TTGCACAATGCATGTTNTTATGGACATTATGAAGTTGCAGAACTTCTTGTTAAACATGGA
2161 ---------+---------+---------+---------+---------+---------+ 2220
     L  H  N  A  C  ?  Y  G  H  Y  E  V  A  E  L  L  V  K  H  G   -

     GCAGTAGTTAATGTAGCTGATTTATGGAAATTTACACCTTTACATGAAGCAGCAGCAAAA
2221 ---------+---------+---------+---------+---------+---------+ 2280
     A  V  V  N  V  A  D  L  W  K  F  T  P  L  H  E  A  A  A  K   -

     GGAAAATATGAAATTTGCAAACTTCTGCTCCAGCATGGTGCAGACCCTACAAAAAAAAAC
2281 ---------+---------+---------+---------+---------+---------+ 2340
     G  K  Y  E  I  C  K  L  L  L  Q  H  G  A  D  P  T  K  K  N   -

     AGGGATGGAAATACTCTTTTGGATCTTGTTAAAGATGGAGANACAGATATTCAAGATNTG
2341 ---------+---------+---------+---------+---------+---------+ 2400
     R  D  G  N  T  L  L  D  L  V  K  D  G  ?  T  D  I  Q  D  ?   -

     CTTAGGGGAGATGCAGTTTTGTTAGATGCTGCCAAGAAGGGTTGTTTAGCCAGAGTGAAG
2401 ---------+---------+---------+---------+---------+---------+ 2460
     L  R  G  D  A  V  L  L  D  A  A  K  K  G  C  L  A  R  V  K   -

     AAGTTNTNTTTTCCTGATAATGTAAATTGCCGNGATACCCAAGGCAGACATTCAACACCT
2461 ---------+---------+---------+---------+---------+---------+ 2520
     K  ?  ?  F  P  D  N  V  N  C  R  D  T  Q  G  R  H  S  T  P   -

     TTACATTTAGCAGGTNNNNNNNNNNNNNNNNNNNNNNNNNNNNNNNNNNNNNNNNNNNNN
2521 ---------+---------+---------+---------+---------+---------+ 2580
```

```
      L  H  L  A  G  ?  ?  ?  ?  ?  ?  ?  ?  ?  ?  ?  ?  ?  ?  ?   -

      NNNNNNNNNNNNNNNNNNNNNNNNNNNNNNNNNNNNNNNNNNNNNNNNNNNNNNNNNNNN
 2581 ---------+---------+---------+---------+---------+---------+ 2640
      ?  ?  ?  ?  ?  ?  ?  ?  ?  ?  ?  ?  ?  ?  ?  ?  ?  ?  ?  ?   -

      NNNNNNNNNNNNNNNNNNNNNNNNNNNNNNNNNNNNNNNNNNNNNNNNNNNNNNNNNNNN
 2641 ---------+---------+---------+---------+---------+---------+ 2700
      ?  ?  ?  ?  ?  ?  ?  ?  ?  ?  ?  ?  ?  ?  ?  ?  ?  ?  ?  ?   -

      NNNNNNNNNNNNNNNNNNNNNNNNNNNNNNNNNNNNNNNNNNNNNNNNNNNNNNNNNNNN
 2701 ---------+---------+---------+---------+---------+---------+ 2760
      ?  ?  ?  ?  ?  ?  ?  ?  ?  ?  ?  ?  ?  ?  ?  ?  ?  ?  ?  ?   -

      NNNNNNNNNNNNNNNNNNNNNNNNNNNNNNNNNNNNNNNNNNNNNNNNNNNNNNNNNNNN
 2761 ---------+---------+---------+---------+---------+---------+ 2820
      ?  ?  ?  ?  ?  ?  ?  ?  ?  ?  ?  ?  ?  ?  ?  ?  ?  ?  ?  ?   -

      NNNNNNNNNNNNNNNNNNNNNNNNNNNNNNNNNNNNNNNNTGACAGCAGCCATGCCCCCA
 2821 ---------+---------+---------+---------+---------+---------+ 2880
      ?  ?  ?  ?  ?  ?  ?  ?  ?  ?  ?  ?  ?  ?  T  A  A  M  P  P   -

      TCTGTTCTGCCCTCTTGTAACAAGCCTCAAGTGCTCAATGGTGTGAGAAGCCCAGGAGCC
 2881 ---------+---------+---------+---------+---------+---------+ 2940
      S  V  L  P  S  C  N  K  P  Q  V  L  N  G  V  R  S  P  G  A   -

      ACTGCAGATGCTCTCTCTTCAGGTCCATCTAGCCCATCAAGCCTTTCTGCAGCCAGCAGT
 2941 ---------+---------+---------+---------+---------+---------+ 3000
      T  A  D  A  L  S  S  G  P  S  S  P  S  S  L  S  A  A  S  S   -

                                                  ANK <-|
      CTTGACAACTTATCTGGGAGTTTTTCAGAACTGTCTTCAGTAGTTAGTTCAAGTGGAACA
 3001 ---------+---------+---------+---------+---------+---------+ 3060
      L  D  N  L  S  G  S  F  S  E  L  S  S  V  V  S  S  S  G  T   -

                                |-> SAM
      GAGGGTGCTTCCAGTTTGGAGAAAAAGGAGGTTCCAGGAGTAGATTTTAGCATAACTCAA
 3061 ---------+---------+---------+---------+---------+---------+ 3120
      E  G  A  S  S  L  E  K  K  E  V  P  G  V  D  F  S  I  T  Q   -

      TTCGTAAGGAATCTTGGACTTGAGCACCTAATGGATATATTTNAGAGAGAACAGATCACT
 3121 ---------+---------+---------+---------+---------+---------+ 3180
      F  V  R  N  L  G  L  E  H  L  M  D  I  F  ?  R  E  Q  I  T   -

      TTGGATGTATTAGTTGAGATGGGGCACAAGGAGCTGAAGGAGATTGGWATCAATGCTTAT
 3181 ---------+---------+---------+---------+---------+---------+ 3240
      L  D  V  L  V  E  M  G  H  K  E  L  K  E  I  G  I  N  A  Y   -

                                               SAM <-|
      GGACATAGGCACAAACTAATTAAAGGAGTCGAGAGACTTATCTCCGGACAACAAGGTCTT
 3241 ---------+---------+---------+---------+---------+---------+ 3300
      G  H  R  H  K  L  I  K  G  V  E  R  L  I  S  G  Q  Q  G  L   -

      AACCCATATTTAACTTTGAACACCTCTGGTAGTGGAACAATTCTTATAGATCTGTCTCCT
 3301 ---------+---------+---------+---------+---------+---------+ 3360
      N  P  Y  L  T  L  N  T  S  G  S  G  T  I  L  I  D  L  S  P   -

      GATGATAAAGAGTTTCAGTCTGTGGAGGAAGAGATGCAAAGTACAGTTCGAGAGCACAGA
```

```
3361 ---------+---------+---------+---------+---------+---------+ 3420
     D  D  K  E  F  Q  S  V  E  E  E  M  Q  S  T  V  R  E  H  R  -

     GATGGAGGTCATGCAGGTGGAATCTTCAACAGATACAATATTCTCAAGATTCAGAAGGTT
3421 ---------+---------+---------+---------+---------+---------+ 3480
     D  G  G  H  A  G  G  I  F  N  R  Y  N  I  L  K  I  Q  K  V  -

     TGTAACANNNNNNNNNNNNGAGCCAAGATTCGGCACGAGGAAAGATACACTCACCGGAGA
3481 ---------+---------+---------+---------+---------+---------+ 3540
     C  N  ?  ?  ?  ?  ?  A  K  I  R  H  E  E  R  Y  T  H  R  R  -

                                   |-> PARP
     AAAGAAGTTTCTGAAGAAAACCACAACCATGCCAATGAACGAATGCTATTTCATGGGTCT
3541 ---------+---------+---------+---------+---------+---------+ 3600
     K  E  V  S  E  E  N  H  N  H  A  N  E  R  M  L  F  H  G  S  -

     CCTTTTGTGAATGCAATTATCCACAAAGGCTTTGATGAAAGGCATGCGTACATAGGTGGT
3601 ---------+---------+---------+---------+---------+---------+ 3660
     P  F  V  N  A  I  I  H  K  G  F  D  E  R  H  A  Y  I  G  G  -

     ATGTTTGGAGCTGGCATTTATTTTGCTGAAAACTCTTCCAAAAGCAATCAATATGTATAT
3661 ---------+---------+---------+---------+---------+---------+ 3720
     M  F  G  A  G  I  Y  F  A  E  N  S  S  K  S  N  Q  Y  V  Y  -

     GGAATTGGAGGAGGTACTGGGTGTCCAGTTCACAAAGACAGATCTTGTTACATTTGCCAC
3721 ---------+---------+---------+---------+---------+---------+ 3780
     G  I  G  G  G  T  G  C  P  V  H  K  D  R  S  C  Y  I  C  H  -

     AGGCAGCTGCTCTTTTGCCGGGTAACCTTGGGAAAGTCTTTCCTGCAGTTCAGTGCAATG
3781 ---------+---------+---------+---------+---------+---------+ 3840
     R  Q  L  L  F  C  R  V  T  L  G  K  S  F  L  Q  F  S  A  M  -

     AAAATGGCACATTCTCCTCCAGGTCATCACTCAGTCACTGGTAGGCCCAGTGTAAATGGC
3841 ---------+---------+---------+---------+---------+---------+ 3900
     K  M  A  H  S  P  P  G  H  H  S  V  T  G  R  P  S  V  N  G  -

     CTAGCATTAGCTGAATATGTTATTTACAGAGGAGAACAGGCTTATCCTGAGTATTTAATT
3901 ---------+---------+---------+---------+---------+---------+ 3960
     L  A  L  A  E  Y  V  I  Y  R  G  E  Q  A  Y  P  E  Y  L  I  -

                   PARP <-|                    | STOP
     ACTTACCAGATTATGAGGCCTGAAGGTATGGTCGATGGATAAATAGTTATTTTAAGAAAC
3961 ---------+---------+---------+---------+---------+---------+ 4020
     T  Y  Q  I  M  R  P  E  G  M  V  D  G  *

     TAATTCCACTGAACCTAAAATCATCAAAGCAGCAGTGGCCTCTACGTTTTACTCCTTTGC
4021 ---------+---------+---------+---------+---------+---------+ 4080

     TGAAAAAAAATCATCTTGCCCACAGGCCTGTGGCAAAAGGATAAAAATGTGAACGAAGTT
4081 ---------+---------+---------+---------+---------+---------+ 4140

     TAACATTCTGACTTGATAAAGCTTTAATAATGTACAGTGTTTTCTAAATATTTCCTGTTT
4141 ---------+---------+---------+---------+---------+---------+ 4200

     TTTCAGCACTTTAACAGATGCCATTCCAGGTTAAACTGGGTTGTCTGTACTAAATTATAA
4201 ---------+---------+---------+---------+---------+---------+ 4260

     ACAGAGTTAACTTGAACCTTTTATATGTTATGCATTGATTCTAACAAACTGTAATGCCCT
```

```
4261 ---------+---------+---------+---------+---------+---------+ 4320

     CAACAGAACTAATTTTACTAATACAATACTGTGTTCTTTAAAACACAGCATTTACACTCA
4321 ---------+---------+---------+---------+---------+---------+ 4380

     ATACAATTTCATTTGTAAAACTGTAAATAAGAGCTTTTGTACTAGCCCAGTATTTATTTA
4381 ---------+---------+---------+---------+---------+---------+ 4440

     CATTGCTTTGTAATATAAATCTGTTTTAGAACTGCAAAAAAAAAAAAAAAAAA
4441 ---------+---------+---------+---------+---------+--- 4493
```

Figure 3(A)

```
     CCCACGCGTCCGGGCAGGAGGGGCCTTGCCAGCTTCCGCCGCCGCGTCGTTTCAGGACC
     --+---------+---------+---------+---------+---------+------- 137

     ?  H  A  S  G  Q  E  G  P  C  Q  L  P  P  P  R  R  F  R  T  -

     CGGACGGCGGATTCGCGCTGCCTCCGCCGCCGCGGGGCAGCCGGGGGGCAGGGAGCCCAT
 138 --+---------+---------+---------+---------+---------+------- 197

     R  T  A  D  S  R  C  L  R  R  R  G  A  A  G  G  Q  G  A  H  -

     CGAANGGGCGCGCGTGGGCGCGGCCATGGGACTGCGCCGGATCCGGTGACAGCAGGGAGC
 198 --+---------+---------+---------+---------+---------+------- 257

     R  ?  G  A  R  G  R  G  H  G  T  A  P  D  P  V  T  A  G  S  -

     CAAGCGGCCCGGGCCCTGAGCGCGTCTTCTCCGGGGGGCCTCGCCCTCCTGCTCGCGGGG
 258 --+---------+---------+---------+---------+---------+------- 317

     Q  A  A  R  A  L  S  A  S  S  P  G  G  L  A  L  L  L  A  G  -

     CCGGGGCTCCTGCTCCGGTTGCTGGCGCTGTTGCTGGCTGTGGCGGCGGCCANGATCATG
 318 --+---------+---------+---------+---------+---------+------- 377

     P  G  L  L  L  R  L  L  A  L  L  L  A  V  A  A  A  ?  I  M  -

     TCGGGTCGCCGCTGCGCCGGCGGGGGANCGGCCTGCGCGANCGCCGCGGCCGAAGCCGTG
 378 --+---------+---------+---------+---------+---------+------- 437

     S  G  R  R  C  A  G  G  G  ?  A  C  A  ?  A  A  A  E  A  V  -
          ANK
     GAACCGGCCGCCCGAAANCTGTTCGAAGCGTGCCGCAACGGGGACGTGGAACGANTCAAG
 438 --+---------+---------+---------+---------+---------+------- 497

     E  P  A  A  R  ?  L  F  E  A  C  R  N  G  D  V  E  R  ?  K  -

     AAGCTGGTGACNCCTGARAAGGTGAACAGCCGCGACACNGCGGGCAGGAAATCCACCCCG
 498 --+---------+---------+---------+---------+---------+------- 557

     K  L  V  T  P  E  K  V  N  S  R  D  T  A  G  R  K  S  T  P  -

     CTGCACTTYCCCGCANGTTTTGGGCGGAAAGACTTANTTRAATATTTGCTTCANAATGGT
 558 --+---------+---------+---------+---------+---------+------- 617

     L  H  F  P  A  ?  F  G  R  K  D  L  ?  ?  Y  L  L  ?  N  G  -

     GCAAATGTYCAANCACGTGATNATGGGGGCCTTATTCCTCTTCATAATGCATGCTCTTTT
 618 --+---------+---------+---------+---------+---------+------- 677

     A  N  V  Q  ?  R  D  ?  G  G  L  I  P  L  H  N  A  C  S  F  -

     GGTCMTGCTRAAANTATCNATCTCCTTTTGCNACATNGTGCANAMCCCAATGCTCGAGAT
 678 --+---------+---------+---------+---------+---------+------- 737

     G  ?  A  ?  ?  I  ?  L  L  L  ?  H  ?  A  ?  P  N  A  R  D  -

     AATTGGAATTATACTCCTCNCNATGAAGCTGCAATTAAAGGAAAGATTGANNNTTGCATT
 738 --+---------+---------+---------+---------+---------+------- 797

     N  W  N  Y  T  P  ?  ?  E  A  A  I  K  G  K  I  ?  ?  C  I  -
```

```
     GTGCTGTTACAGCATGGAGCTGAGCCAACCATCCGAAATACAGATGGAAGGACAGCATTG
798  --+---------+---------+---------+---------+---------+------- 857
      V  L  L  Q  H  G  A  E  P  T  I  R  N  T  D  G  R  T  A  L   -

     GATTTAGCAGATCCATCTGCCAAAGCAGTGCTTACTGGTGAATATAAGAAAGATGAACTC
858  --+---------+---------+---------+---------+---------+------- 917
      D  L  A  D  P  S  A  K  A  V  L  T  G  E  Y  K  K  D  E  L   -

     TTAGAAAGTGCCAGGAGTGGCAATGAAGAAAAAATGATGGCTCTACTCACACCATTAAAT
918  --+---------+---------+---------+---------+---------+------- 977
      L  E  S  A  R  S  G  N  E  E  K  M  M  A  L  L  T  P  L  N   -

     GTCAACTGCCACGCAAGTGATGGCAGAAAGTCAACTCCATTACATTTGGCAGCAGGATAT
978  --+---------+---------+---------+---------+---------+------- 1037
      V  N  C  H  A  S  D  G  R  K  S  T  P  L  H  L  A  A  G  Y   -

      AACAGAGTAAAGATTGTACAGCTGTTACTGCAACATGGAGCTGATGTCCATGCTAAAGAT
1038 --+---------+---------+---------+---------+---------+------- 1097
      N  R  V  K  I  V  Q  L  L  L  Q  H  G  A  D  V  H  A  K  D   -

      AAAGGTGATCTGGTACCATTACACAATGCCTGTTCTTATGGTCATTATGAAGTAACTGAA
1098 --+---------+---------+---------+---------+---------+------- 1157
      K  G  D  L  V  P  L  H  N  A  C  S  Y  G  H  Y  E  V  T  E   -

      CTTTTGGTCAAGCATGGTGCCTGTGTAAATGCAATGGACTTGTGGCAATTCACTCCTCTT
1158 --+---------+---------+---------+---------+---------+------- 1217
      L  L  V  K  H  G  A  C  V  N  A  M  D  L  W  Q  F  T  P  L   -

      CATGAGGCAGCTTCTAAGAACAGGGTTGAAGTATGTTCTCTTCTCTTAAGTTATGGTGCA
1218 --+---------+---------+---------+---------+---------+------- 1277
      H  E  A  A  S  K  N  R  V  E  V  C  S  L  L  L  S  Y  G  A   -

      GACCCAACACTGCTCAATTGTCACAATAAAAGTGCTATAGACTTGGCTCCCACACCACAG
1278 --+---------+---------+---------+---------+---------+------- 1337
      D  P  T  L  L  N  C  H  N  K  S  A  I  D  L  A  P  T  P  Q   -

      TTAAAAGAAAGATTAGCATATGAATTTAAAGGCCACTCGTTGCTGCAAGCTGCACGAGAA
1338 --+---------+---------+---------+---------+---------+------- 1397
      L  K  E  R  L  A  Y  E  F  K  G  H  S  L  L  Q  A  A  R  E   -

      GCTGATGTTACTCGAATCAAAAAACATCTCTCTCTGGAAATGGTGAATTTCAAGCATCCT
1398 --+---------+---------+---------+---------+---------+------- 1457
      A  D  V  T  R  I  K  K  H  L  S  L  E  M  V  N  F  K  H  P   -

      CAAACACATGAAACAGCATTGCATTGTGCTGCTGCATCTCCATATCCCAAAAGAAAGCAA
1458 --+---------+---------+---------+---------+---------+------- 1517
      Q  T  H  E  T  A  L  H  C  A  A  A  S  P  Y  P  K  R  K  Q   -

      ATATGTGAACTGTTGCTAAGAAAAGGAGCAAACATCAATGAAAAGACTAAAGAATTCTTG
1518 --+---------+---------+---------+---------+---------+------- 1577
      I  C  E  L  L  L  R  K  G  A  N  I  N  E  K  T  K  E  F  L   -
```

Figure 3(C)

```
      ACTCCTCTGCACGTGGCATCTGAGAAAGCTCATAATGATGTTGTTGAAGTAGTGGTGAAA
1578  --+---------+---------+---------+---------+---------+------ 1637
       T  P  L  H  V  A  S  E  K  A  H  N  D  V  V  E  V  V  V  K  -

      CATGAAGCAAAGGTTAATGCTCTGGATAATCTTGGTCAGACTTCTCTACACAGAGCTGCA
1638  --+---------+---------+---------+---------+---------+------ 1697
       H  E  A  K  V  N  A  L  D  N  L  G  Q  T  S  L  H  R  A  A  -

      TATTGTGGTCATCTACAAACCTGCCGCCTACTCCTGAGCTATGGGTGTGATCCTAACATT
1698  --+---------+---------+---------+---------+---------+------ 1757
       Y  C  G  H  L  Q  T  C  R  L  L  L  S  Y  G  C  D  P  N  I  -

      ATATCCCTTCAGGGCTTTACTGCTTTACAGATGGGAAATGAAAATGTACAGCAACTCCTC
1758  --+---------+---------+---------+---------+---------+------ 1817
       I  S  L  Q  G  F  T  A  L  Q  M  G  N  E  N  V  Q  Q  L  L  -

      CAAGAGGGTATCTCATTAGGTAATTCAGAGGCAGACAGACAATTGCTGGAAGCTGCAAAG
1818  --+---------+---------+---------+---------+---------+------ 1877
       Q  E  G  I  S  L  G  N  S  E  A  D  R  Q  L  L  E  A  A  K  -

      GCTGGAGATGTCGAAACTGTAAAAAAACTGTGTACTGTTCAGAGTGTCAACTGCAGAGAC
1878  --+---------+---------+---------+---------+---------+------ 1937
       A  G  D  V  E  T  V  K  K  L  C  T  V  Q  S  V  N  C  R  D  -

      ATTGAAGGGCGTCAGTCTACACCACTTCATTTTGCAGCTGGGTATAACAGAGTGTCCGTG
1938  --+---------+---------+---------+---------+---------+------ 1997
       I  E  G  R  Q  S  T  P  L  H  F  A  A  G  Y  N  R  V  S  V  -

      GTGGAATATCTGCTACAGCATGGAGCTGATGTGCATGCTAAAGATAAAGGNGGCCTTGTA
1998  --+---------+---------+---------+---------+---------+------ 2057
       V  E  Y  L  L  Q  H  G  A  D  V  H  A  K  D  K  G  G  L  V  -

      CCTTTGCACAATGCATGTTNTTATGGACATTATGAAGTTGCAGAACTTCTTGTTAAACAT
2058  --+---------+---------+---------+---------+---------+------ 2117
       P  L  H  N  A  C  ?  Y  G  H  Y  E  V  A  E  L  L  V  K  H  -

      GGAGCAGTAGTTAATGTAGCTGATTTATGGAAATTTACACCTTTACATGAAGCAGCAGCA
2118  --+---------+---------+---------+---------+---------+------ 2177
       G  A  V  V  N  V  A  D  L  W  K  F  T  P  L  H  E  A  A  A  -

      AAAGGAAAATATGAAATTTGCAAACTTCTGCTCCAGCATGGTGCAGACCCTACAAAAAAA
2178  --+---------+---------+---------+---------+---------+------ 2237
       K  G  K  Y  E  I  C  K  L  L  L  Q  H  G  A  D  P  T  K  K  -

      AAAAAAAAAGGAAANATTCNTTTGGATCTTGTTAAAGATGGAGANACAGATATTCAAGAT
2238  --+---------+---------+---------+---------+---------+------ 2297
       K  K  K  G  ?  I  ?  L  D  L  V  K  D  G  ?  T  D  I  Q  D  -

      NTGCTTAGGGGAGATGCAGTTTTGTTAGATGCTGCCAAGAAGGGTTGTTTAGCCAGAGTG
2298  --+---------+---------+---------+---------+---------+------ 2357
       ?  L  R  G  D  A  V  L  L  D  A  A  K  K  G  C  L  A  R  V  -

      AAGAAGTTNTNTTTTCCTGATAATGTAAATTGCCGNGATACCCAAGGCAGACATTCAACA
```

CCTTTACATTTAGCAGGTNNNNNNNNNNNNNNNNNNNNNNNNNNNNNNNNNNNNNNNNNN
--+---------+---------+---------+---------+---------+------- 2477

P L H L A G ? ? ? ? ? ? ? ? ? ? ? ? ? ? -

NNNNNNNNNNNNNNNNNNNNNNNNNNNNNNNNNNNNNNNNNNNNNNNNNNNNNNNNNNNN
--+---------+---------+---------+---------+---------+------- 2537

? ? ? ? ? ? ? ? ? ? ? ? ? ? ? ? ? ? ? ? -

NNNNNNNNNNNNNNNNNNNNNNNNNNNNNNNNNNNNNNNNNNNNNNNNNNNNNNNNNNNN
--+---------+---------+---------+---------+---------+------- 2597

? ? ? ? ? ? ? ? ? ? ? ? ? ? ? ? ? ? ? ? -

NNNNNNNNNNNNNNNNNNNNNNNNNNNNNNNNNNNNNNNNNNNNNNNNNNNNNNNNNNNN
--+---------+---------+---------+---------+---------+------- 2657

? ? ? ? ? ? ? ? ? ? ? ? ? ? ? ? ? ? ? ? -

NNNNNNNNNNNNNNNNNNNNNNNNNNNNNNNNNNNNNNNNNNNNNNNNNNNNNNNNNNNN
--+---------+---------+---------+---------+---------+------- 2717

? ? ? ? ? ? ? ? ? ? ? ? ? ? ? ? ? ? ? ? -

NNNNNNNNNNNNNNNNNNNNNNNNNNNNNNNNNNTGACAGCAGCCATGCCCCCATCTGTT
--+---------+---------+---------+---------+---------+------- 2777

? ? ? ? ? ? ? ? ? ? ? ? T A A M P P S V -

CTGCCCTCTTGTAACAAGCCTCAAGTGCTCAATGGTGTGAGAAGCCCAGGAGCCACTGCA
--+---------+---------+---------+---------+---------+------- 2837

L P S C N K P Q V L N G V R S P G A T A -

GATGCTCTCTCTTCAGGTCCATCTAGCCCATCAAGCCTTTCTGCAGCCAGCAGTCTTGAC
--+---------+---------+---------+---------+---------+------- 2897

D A L S S G P S S P S S L S A A S S L D -

ANC

AACTTATCTGGGAGTTTTTCAGAACTGTCTTCAGTAGTTAGTTCAAGTGGAACAGAGGGT
--+---------+---------+---------+---------+---------+------- 2957

N L S G S F S E L S S V V S S S G T E G -

SAM

GCTTCCAGTTTGGAGAAAAAGGAGGTTCCAGGAGTAGATTTTAGCATAACTCAATTCGTA
--+---------+---------+---------+---------+---------+------- 3017

A S S L E K K E V P G V D F S I T Q F V -

AGGAATCTTGGACTTGAGCACCTAATGGATATATTTNAGAGAGAACAGATCACTTTGGAT
--+---------+---------+---------+---------+---------+------- 3077

R N L G L E H L M D I F ? R E Q I T L D -

GTATTAGTTGAGATGGGGCACAAGGAGCTGAAGGAGATTGGWATCAATGCTTATGGACAT
--+---------+---------+---------+---------+---------+------- 3137

V L V E M G H K E L K E I G I N A Y G H -

SAM

AGGCACAAACTAATTAAAaGttTCGAGAGACTTATCTCCGGACAACAAGGTCTTAACCCA
--+---------+---------+---------+---------+---------+------- 3197

Figure 3(E)

```
       R  H  K  L  I  K  S  F  E  R  L  I  S  G  Q  Q  G  L  N  P  -
       TATTTAACTTTGAACACCTCTGGTAGTGGAACAATTCTTATAGATCTGTCTCCTGATGAT
3198   --+---------+---------+---------+---------+---------+------- 3257
       Y  L  T  L  N  T  S  G  S  G  T  I  L  I  D  L  S  P  D  D  -
       AAAGAGTTTCAGTCTGTGGAGGAAGAGATGCAAAGTACAGTTCGAGAGCACAGAGATGGA
3258   --+---------+---------+---------+---------+---------+------- 3317
       K  E  F  Q  S  V  E  E  E  M  Q  S  T  V  R  E  H  R  D  G  -
       GGTCATGCAGGTGGAATCTTCAACAGATACAATATTCTCAAGATTCAGAAGGTTTGTAAC
3318   --+---------+---------+---------+---------+---------+------- 3377
       G  H  A  G  G  I  F  N  R  Y  N  I  L  K  I  Q  K  V  C  N  -
       AgagccaagattcggcacgaGGAAAGATACACTCACCGGAGAAAAGAAGTTTCTGAAGAA
3378   --+---------+---------+---------+---------+---------+------- 3437
       R  A  K  I  R  H  E  E  R  Y  T  H  R  R  K  E  V  S  E  E  -
       AACCACAACCATGCCAATGAACGAATGCTATTTCATGGGTCTCCTTTTGTGAATGCAATT
3438   --+---------+---------+---------+---------+---------+------- 3497
       N  H  N  H  A  N  E  R  M  L  F  H  G  S  P  F  V  N  A  I  -
       ATCCACAAAGGCTTTGATGAAAGGCATGCGTACATAGGTGGTATGTTTGGAGCTGGCATT
3498   --+---------+---------+---------+---------+---------+------- 3557
       I  H  K  G  F  D  E  R  H  A  Y  I  G  G  M  F  G  A  G  I  -
       TATTTTGCTGAAAACTCTTCCAAAAGCAATCAATATGTATATGGAATTGGAGGAGGTACT
3558   --+---------+---------+---------+---------+---------+------- 3617
       Y  F  A  E  N  S  S  K  S  N  Q  Y  V  Y  G  I  G  G  G  T  -
       GGGTGTCCAGTTCACAAAGACAGATCTTGTTACATTTGCCACAGGCAGCTGCTCTTTTGC
3618   --+---------+---------+---------+---------+---------+------- 3677
       G  C  P  V  H  K  D  R  S  C  Y  I  C  H  R  Q  L  L  F  C  -
       CGGGTAACCTTGGGAAAGTCTTTCCTGCAGTTCAGTGCAATGAAAATGGCACATTCTCCT
3678   --+---------+---------+---------+---------+---------+------- 3737
       R  V  T  L  G  K  S  F  L  Q  F  S  A  M  K  M  A  H  S  P  -
       CCAGGTCATCACTCAGTCACTGGTAGGCCCAGTGTAAATGGCCTAGCATTAGCTGAATAT
3738   --+---------+---------+---------+---------+---------+------- 3797
       P  G  H  H  S  V  T  G  R  P  S  V  N  G  L  A  L  A  E  Y  -
       GTTATTTACAGAGGAGAACAGGCTTATCCTGAGTATTTAATTACTTACCAGATTATGAGG
3798   --+---------+---------+---------+---------+---------+------- 3857
       V  I  Y  R  G  E  Q  A  Y  P  E  Y  L  I  T  Y  Q  I  M  R  -
       CCTGAAGGTATGGTCGATGGATAAATAGTTATTTTAAGAAACTAATTCCACTGAACCTAA
3858   --+---------+---------+---------+---------+---------+------- 3917
       P  E  G  M  V  D  G  *  I  V  I  L  R  N  *  F  H  *  T  *  -
       AATCATCAAAGCAGCAGTGGCCTCTACGTTTTACTCCTTTGCTGAAAAAAAATCATCTTG
3918   --+---------+---------+---------+---------+---------+------- 3977
```

Figure 3(F)

```
      N  H  Q  S  S  S  G  L  Y  V  L  L  L  C  *  K  K  I  I  L  -
     CCCACAGGCCTGTGGCAAAAGGATAAAAATGTGAACGAAGTTTAACATTCTGACTTGATA
3978 --+---------+---------+---------+---------+---------+------- 4037
      P  T  G  L  W  Q  K  D  K  N  V  N  E  V  *  H  S  D  L  I  -
     AAGCTTTAATAATGTACAGTGTTTTCTAAATATTTCCTGTTTTTTCAGCACTTTAACAGA
4038 --+---------+---------+---------+---------+---------+------- 4097
      K  L  *  *  C  T  V  F  S  K  Y  F  L  F  F  Q  H  F  N  R  -
     TGCCATTCCAGGTTAAACTGGGTTGTCTGTACTAAATTATAAACAGAGTTAACTTGAACC
4098 --+---------+---------+---------+---------+---------+------- 4157
      C  H  S  R  L  N  W  V  V  C  T  K  L  *  T  E  L  T  *  T  -
     TTTTATATGTTATGCATTGATTCTAACAAACTGTAATGCCCTCAACAGAACTAATTTTAC
4158 --+---------+---------+---------+---------+---------+------- 4217
      F  Y  M  L  C  I  D  S  N  K  L  *  C  P  Q  Q  N  *  F  Y  -
     TAATACAATACTGTGTTCTTTAAAACACAGCATTTACACTGAATACAATTTCATTTGTAA
4218 --+---------+---------+---------+---------+---------+------- 4277
      *  Y  N  T  V  F  F  K  T  Q  H  L  H  *  I  Q  F  H  L  *  -
     AACTGTAAATAAGAGCTTTTGTACTAGCCCAGTATTTATTTACATTGCTTTGTAATATAA
4278 --+---------+---------+---------+---------+---------+------- 4337
      N  C  K  *  E  L  L  Y  *  P  S  I  Y  L  H  C  F  V  I  *  -
     ATCTGTTTTAGAACTGCAAAAAAAAAAAAAAAAAATC
4338 --+---------+---------+---------+---- 4374
      I  C  F  R  T  A  K  K  K  K  K  N     -
```

Figure 4(A)

```
        10         20         30         40         50         60         70         80         90        100
1234567890 1234567890 1234567890 1234567890 1234567890 1234567890 1234567890 1234567890 1234567890 1234567890
GGCAGGAGGG GCCTTGCCAG CTTCCGCCGC CGCGTCGTTT CAGGACCCGG ACGGCGGATT CGCGCTGCCT CCGCCGCCGC GGGGCAGCCG GGGGGCAGGG   100

AGCCCATCGA GGGGCGCGCG TGGGCGCGGC CATGGGACTG CGCCGGATCC GGTGACAGCA GGGAGCCAAG CGGCCCGGGC CCTGAGCGCG TCTTCTCCGG   200

GGGGCCTCGC CCTCCTGCTC GCGGGGCCGG GGCTCCTGCT CCGGTTGCTG GCGCTGTTGC TGGCTGTGGC GGCGGCCAGG ATCATGTCGG GTCGCCGCTG   300
                                                                                            M  S  G   R  R  C
CGCCGGCGGG GGAGCGGCCT GCGCGAGCGC CGCGGCCGAG GCCGTGGAGC CGGCCGCCCG AGAGCTGTTC GAGGCGTGCC GCAACGGGGA CGTGGAACGA   400
 A  G  G   G  A  A  C   A  S  A   A  A  E   A  V  E  P   A  A  R   E  L  F   E  A  C  R   N  G  D   V  E  R
GTCAAGAGGC TGGTGACGCC TGAGAAGGTG AACAGCCGCG ACACGGCGGG CAGGAAATCC ACCCCGCTGC ACTTCGCCGC AGGTTTTGGG CGGAAAGACG   500
V  K  R  L   V  T  P   E  K  V   N  S  R  D   T  A  G   R  K  S   T  P  L  H   F  A  A   G  F  G   R  K  D  V
TAGTTGAATA TTTGCTTCAG AATGGTGCAA ATGTCCAAGC ACGTGATGAT GGGGGCCTTA TTCCTCTTCA TAATGCATGC TCTTTTGGTC ATGCTGAAGT   600
  V  E  Y   L  L  Q   N  G  A  N   V  Q  A   R  D  D   G  G  L  I   P  L  H   N  A  C   S  F  G  H   A  E  V
AGTCAATCTC CTTTTGCGAC ATGGTGCAGA CCCCAATGCT CGAGATAATT GGAATTATAC TCCTCTCCAT GAAGCTGCAA TTAAAGGAAA GATTGATGTT   700
 V  N  L   L  L  R  H   G  A  D   P  N  A   R  D  N  W   N  Y  T   P  L  H   E  A  A  I   K  G  K   I  D  V
TGCATTGTGC TGTTACAGCA TGGAGCTGAG CCAACCATCC GAAATACAGA TGGAAGGACA GCATTGGATT TAGCAGATCC ATCTGCCAAA GCAGTGCTTA   800
C  I  V  L   L  Q  H   G  A  E   P  T  I  R   N  T  D   G  R  T   A  L  D  L   A  D  P   S  A  K   A  V  L  T
CTGGTGAATA TAAGAAAGAT GAACTCTTAG AAAGTGCCAG GAGTGGCAAT GAAGAAAAAA TGATGGCTCT ACTCACACCA TTAAATGTCA ACTGCCACGC   900
  G  E  Y   K  K  D   E  L  L  E   S  A  R   S  G  N   E  E  K  M   M  A  L   L  T  P   L  N  V  N   C  H  A
AAGTGATGGC AGAAAGTCAA CTCCATTACA TTTGGCAGCA GGATATAACA GAGTAAAGAT TGTACAGCTG TTACTGCAAC ATGGAGCTGA TGTCCATGCT  1000
 S  D  G   R  K  S  T   P  L  H   L  A  A   G  Y  N  R   V  K  I   V  Q  L   L  L  Q  H   G  A  D   V  H  A
AAAGATAAAG GTGATCTGGT ACCATTACAC AATGCCTGTT CTTATGGTCA TTATGAAGTA ACTGAACTTT TGGTCAAGCA TGGTGCCTGT GTAAATGCAA  1100
K  D  K  G   D  L  V   P  L  H   N  A  C  S   Y  G  H   Y  E  V   T  E  L  L   V  K  H   G  A  C   V  N  A  M
TGGACTTGTG GCAATTCACT CCTCTTCATG AGGCAGCTTC TAAGAACAGG GTTGAAGTAT GTTCTCTTCT CTTAAGTTAT GGTGCAGACC CAACACTGCT  1200
  D  L  W   Q  F  T   P  L  H  E   A  A  S   K  N  R   V  E  V  C   S  L  L   L  S  Y   G  A  D  P   T  L  L
CAATTGTCAC AATAAAAGTG CTATAGACTT GGCTCCCACA CCACAGTTAA AAGAAAGATT AGCATATGAA TTTAAAGGCC ACTCGTTGCT GCAAGCTGCA  1300
 N  C  H   N  K  S  A   I  D  L   A  P  T   P  Q  L  K   E  R  L   A  Y  E   F  K  G  H   S  L  L   Q  A  A
CGAGAAGCTG ATGTTACTCG AATCAAAAAA CATCTCTCTC TGGAAATGGT GAATTTCAAG CATCCTCAAA CACATGAAAC AGCATTGCAT TGTGCTGCTG  1400
R  E  A  D   V  T  R   I  K  K   H  L  S  L   E  M  V   N  F  K   H  P  Q  T   H  E  T   A  L  H   C  A  A  A
CATCTCCATA TCCCAAAAGA AAGCAAATAT GTGAACTGTT GCTAAGAAAA GGAGCAAACA TCAATGAAAA GACTAAAGAA TTCTTGACTC CTCTGCACGT  1500
  S  P  Y   P  K  R   K  Q  I  C   E  L  L   L  R  K   G  A  N  I   N  E  K   T  K  E   F  L  T  P   L  H  V
GGCATCTGAG AAAGCTCATA ATGATGTTGT TGAAGTAGTG GTGAAACATG AAGCAAAGGT TAATGCTCTG GATAATCTTG GTCAGACTTC TCTACACAGA  1600
 A  S  E   K  A  H  N   D  V  V   E  V  V   V  K  H  E   A  K  V   N  A  L   D  N  L  G   Q  T  S   L  H  R
GCTGCATATT GTGGTCATCT ACAAACCTGC CGCCTACTCC TGAGCTATGG GTGTGATCCT AACATTATAT CCCTTCAGGG CTTTACTGCT TTACAGATGG  1700
A  A  Y  C   G  H  L   Q  T  C   R  L  L  L   S  Y  G   C  D  P   N  I  I  S   L  Q  G   F  T  A   L  Q  M  G
```

Figure 4(B)

```
         10         20         30         40         50         60         70         80         90        100
1234567890 1234567890 1234567890 1234567890 1234567890 1234567890 1234567890 1234567890 1234567890 1234567890
GAAATGAAAA TGTACAGCAA CTCCTCCAAG AGGGTATCTC ATTAGGTAAT TCAGAGGCAG ACAGACAATT GCTGGAAGCT GCAAAGGCTG GAGATGTCGA 1800
 N  E  N   V  Q  Q   L  L  Q  E   G  I  S   L  G  N   S  E  A  D   R  Q  L   L  E  A   A  K  A  G   D  V  E

AACTGTAAAA AAACTGTGTA CTGTTCAGAG TGTCAACTGC AGAGACATTG AAGGGCGTCA GTCTACACCA CTTCATTTTG CAGCTGGGTA TAACAGAGTG 1900
 T  V  K   K  L  C  T   V  Q  S   V  N  C   R  D  I  E   G  R  Q   S  T  P   L  H  F  A   A  G  Y   N  R  V

TCCGTGGTGG AATATCTGCT ACAGCATGGA GCTGATGTGC ATGCTAAAGA TAAAGGAGGC CTTGTACCTT TGCACAATGC ATGTTCTTAT GGACATTATG 2000
S  V  V  E   Y  L  L   Q  H  G   A  D  V  H   A  K  D   K  G  G   L  V  P  L   H  N  A   C  S  Y   G  H  Y  E

AAGTTGCAGA ACTTCTTGTT AAACATGGAG CAGTAGTTAA TGTAGCTGAT TTATGGAAAT TTACACCTTT ACATGAAGCA GCAGCAAAAG GAAAATATGA 2100
 V  A  E   L  L  V   K  H  G  A   V  V  N   V  A  D   L  W  K  F   T  P  L   H  E  A   A  A  K  G   K  Y  E

AATTTGCAAA CTTCTGCTCC AGCATGGTGC AGACCCTACA AAAAAAAACA GGGATGGAAA TACTCCTTTG GATCTTGTTA AAGATGGAGA TACAGATATT 2200
 I  C  K   L  L  L  Q   H  G  A   D  P  T   K  K  N  R   D  G  N   T  P  L   D  L  V  K   D  G  D   T  D  I

CAAGATCTGC TTAGGGGAGA TGCAGCTTTG CTAGATGCTG CCAAGAAGGG TTGTTTAGCC AGAGTGAAGA AGTTGTCTTC TCCTGATAAT GTAAATTGCC 2300
Q  D  L  L   R  G  D   A  A  L   L  D  A  A   K  K  G   C  L  A   R  V  K  K   L  S  S   P  D  N   V  N  C  R

GCGATACCCA AGGCAGACAT TCAACACCTT TACATTTAGC AGCTGGTTAT AATAATTTAG AAGTTGCAGA GTATTTGTTA CAACACGGAG CTGATGTGAA 2400
 D  T  Q   G  R  H   S  T  P  L   H  L  A   A  G  Y   N  N  L  E   V  A  E   Y  L  L   Q  H  G  A   D  V  N

TGCCCAAGAC AAAGGAGGAC TTATTCCTTT ACATAATGCA GCATCTTACG GGCATGTAGA TGTAGCAGCT CTACTAATAA AGTATAATGC ATGTGTCAAT 2500
 A  Q  D   K  G  G  L   I  P  L   H  N  A   A  S  Y  G   H  V  D   V  A  A   L  L  I  K   Y  N  A   C  V  N

GCCACGGACA AATGGGCTTT CACACCTTTG CACGAAGCAG CCCAAAAGGG ACGAACACAG CTTTGTGCTT TGTTGCTAGC CCATGGAGCT GACCCGACTC 2600
A  T  D  K   W  A  F   T  P  L   H  E  A  A   Q  K  G   R  T  Q   L  C  A  L   L  L  A   H  G  A   D  P  T  L

TTAAAAATCA GGAAGGACAA ACACCTTTAG ATTTAGTTTC AGCGGATGAT GTCAGCGCTC TTCTGACAGC AGCCATGCCC CCATCTGCTC TGCCCTCTTG 2700
 K  N  Q   E  G  Q   T  P  L  D   L  V  S   A  D  D   V  S  A  L   L  T  A   A  M  P   P  S  A  L   P  S  C

TTACAAGCCT CAAGTGCTCA ATGGTGTGAG AAGCCCAGGA GCCACTGCAG ATGCTCTCTC TTCAGGTCCA TCTAGCCCAT CAAGCCTTTC TGCAGCCAGC 2800
 Y  K  P   Q  V  L  N   G  V  R   S  P  G   A  T  A  D   A  L  S   S  G  P   S  S  P  S   S  L  S   A  A  S

AGTCTTGACA ACTTATCTGG GAGTTTTTCA GAACTGTCTT CAGTAGTTAG TTCAAGTGGA ACAGAGGGTG CTTCCAGTTT GGAGAAAAAG GAGGTTCCAG 2900
S  L  D  N   L  S  G   S  F  S   E  L  S  S   V  V  S   S  S  G   T  E  G  A   S  S  L   E  K  K   E  V  P  G

GAGTAGATTT TAGCATAACT CAATTCGTAA GGAATCTTGG ACTTGAGCAC CTAATGGATA TATTTGAGAG AGAACAGATC ACTTTGGATG TATTAGTTGA 3000
 V  D  F   S  I  T   Q  F  V  R   N  L  G   L  E  H   L  M  D  I   F  E  R   E  Q  I   T  L  D  V   L  V  E

GATGGGGCAC AAGGAGCTGA AGGAGATTGG AATCAATGCT TATGGACATA GGCACAAACT AATTAAAGGA GTCGAGAGAC TTATCTCCGG ACAACAAGGT 3100
 M  G  H   K  E  L  K   E  I  G   I  N  A   Y  G  H  R   H  K  L   I  K  G   V  E  R  L   I  S  G   Q  Q  G

CTTAACCCAT ATTTAACTTT GAACACCTCT GGTAGTGGAA CAATTCTTAT AGATCTGTCT CCTGATGATA AAGAGTTTCA GTCTGTGGAG GAAGAGATGC 3200
L  N  P  Y   L  T  L   N  T  S   G  S  G  T   I  L  I   D  L  S   P  D  D  K   E  F  Q   S  V  E   E  E  M  Q

AAAGTACAGT TCGAGAGCAC AGAGATGGAG GTCATGCAGG TGGAATCTTC AACAGATACA ATATTCTCAA GATTCAGAAG GTTTGTAACA AGAAACTATG 3300
 S  T  V   R  E  H   R  D  G  G   H  A  G   G  I  F   N  R  Y  N   I  L  K   I  Q  K   V  C  N  K   K  L  W

GGAAAGATAC ACTCACCGGA GAAAAGAAGT TTCTGAAGAA AACCACAACC ATGCCAATGA ACGAATGCTA TTTCATGGGT CTCCTTTTGT GAATGCAATT 3400
 E  R  Y   T  H  R  R   K  E  V   S  E  E   N  H  N  H   A  N  E   R  M  L   F  H  G  S   P  F  V   N  A  I

ATCCACAAAG GCTTTGATGA AAGGCATGCG TACATAGGTG GTATGTTTGG AGCTGGCATT TATTTTGCTG AAAACTCTTC CAAAAGCAAT CAATATGTAT 3500
I  H  K  G   F  D  E   R  H  A   Y  I  G  G   M  F  G   A  G  I   Y  F  A  E   N  S  S   K  S  N   Q  Y  V  Y

ATGGAATTGG AGGAGGTACT GGGTGTCCAG TTCACAAAGA CAGATCTTGT TACATTTGCC ACAGGCAGCT GCTCTTTTGC CGGGTAACCT TGGGAAAGTC 3600
 G  I  G   G  G  T   G  C  P  V   H  K  D   R  S  C   Y  I  C  H   R  Q  L   L  F  C   R  V  T  L   G  K  S

TTTCCTGCAG TTCAGTGCAA TGAAAATGGC ACATTCTCCT CCAGGTCATC ACTCAGTCAC TGGTAGGCCC AGTGTAAATG GCCTAGCATT AGCTGAATAT 3700
 F  L  Q   F  S  A  M   K  M  A   H  S  P   P  G  H  H   S  V  T   G  R  P   S  V  N  G   L  A  L   A  E  Y

GTTATTTACA GAGGAGAACA GGCTTATCCT GAGTATTTAA TTACTTACCA GATTATGAGG CCTGAAGGTA TGGTCGATGG ATAAATAGTT ATTTTAAGAA 3800
V  I  Y  R   G  E  Q   A  Y  P   E  Y  L  I   T  Y  Q   I  M  R   P  E  G  M   V  D  G

ACTAATTCCA CTGAACCTAA AATCATCAAA GCAGCAGTGG CCTCTACGTT TTACTCCTTT GCTGAAAAAA AATCATCTTG CCCACAGGCC TGTGGCAAAA 3900

GGATAAAAAT GTGAACGAAG TTTAACATTC TGACTTGATA AAGCTTTAAT AATGTACAGT GTTTTCTAAA TATTTCCTGT TTTTTCAGCA CTTTAACAGA 4000

TGCCATTCCA GGTTAAACTG GGTTGTCTGT ACTAAATTAT AAACAGAGTT AACTTGAACC TTTTATATGT TATGCATTGA TTCTAACAAA CTGTAATGCC 4100

CTCAACAGAA CTAATTTTAC TAATACAATA CTGTGTTCTT TAAAACACAG CATTTACACT GAATACAATT TCATTTGTAA AACTGTAAAT AAGAGCTTTT 4200

GTACTAGCCC AGTATTTATT TACATTGCTT TGTAATATAA ATCTGTTTTA GAACTGCAAA AAAAAAAAAA AAAAA                            4275
```

Figure 5

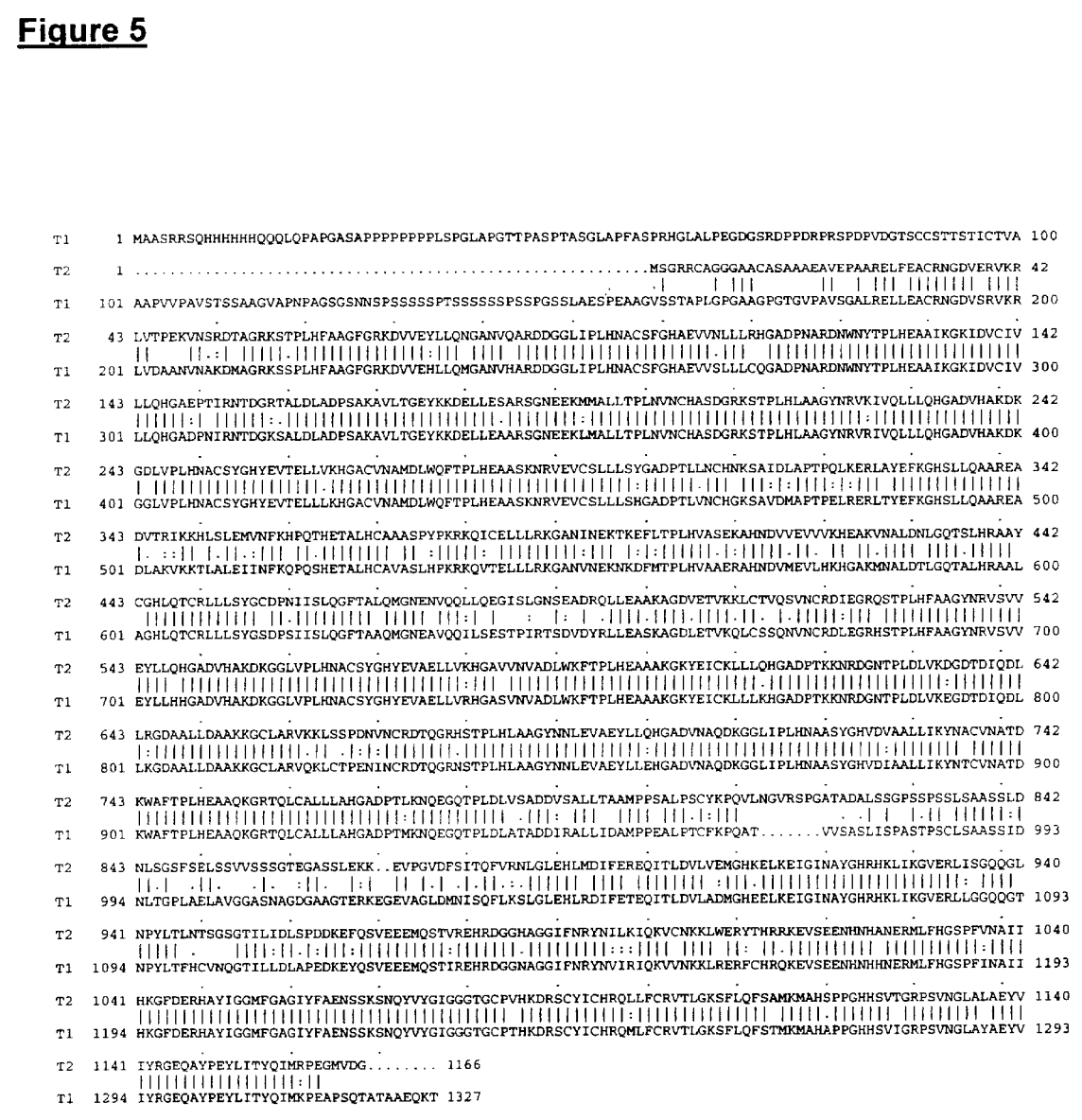

```
T1     1 MAASRRSQHHHHHHQQQLQPAPGASAPPPPPPPPLSPGLAPGTTPASPTASGLAPFASPRHGLALPEGDGSRDPPDRPRSPDPVDGTSCCSTTSTICTVA 100
T2     1 ..............................................MSGRRCAGGGAACASAAAEAVEPAARELFEACRNGDVERVKR 42
                                                         .|  ||||    || |.||| ||||||||  ||||
T1   101 AAPVVPAVSTSSAAGVAPNPAGSGSNNSPSSSSSPTSSSSSPSSPGSSLAESPEAAGVSSTAPLGPGAAGPGTGVPAVSGALRELLEACRNGDVSRVKR 200

T2    43 LVTPEKVNSRDTAGRKSTPLHFAAGFGRKDVVEYLLQNGANVQARDDGGLIPLHNACSFGHAEVVNLLLRHGADPNARDNWNYTPLHEAAIKGKIDVCIV 142
         ||    ||.:| |||||.||||||||||||||:||| |||| ||||||||||||||||||||||.||  ||||||||||||||||||||||||||||
T1   201 LVDAANVNAKDMAGRKSSPLHFAAGFGRKDVVEHLLQMGANVHARDDGGLIPLHNACSFGHAEVVSLLLCQGADPNARDNWNYTPLHEAAIKGKIDVCIV 300

T2   143 LLQHGAEPTIRNTDGRTALDLADPSAKAVLTGEYKKDELLESARSGNEEKMMALLTPLNVNCHASDGRKSTPLHLAAGYNRVKIVQLLLQHGADVHAKDK 242
         ||||||:| |||||:.||||||||||||||||||||||||:.||||||||:|||||||||||||||||||||||||||||.|||||||||||||||||
T1   301 LLQHGADPNIRNTDGKSALDLADPSAKAVLTGEYKKDELLEAARSGNEEKLMALLTPLNVNCHASDGRKSTPLHLAAGYNRVRIVQLLLQHGADVHAKDK 400

T2   243 GDLVPLHNACSYGHYEVTELLVKHGACVNAMDLWQFTPLHEAASKNRVEVCSLLLSYGADPTLLNCHNKSAIDLAPTPQLKERLAYEFKGHSLLQAAREA 342
         ||||||||||||||||||||||.|||||||||||||||||||||||||||||||||||||||||||.||:||:|:|||||:|||||||||||||||||
T1   401 GGLVPLHNACSYGHYEVTELLLKHGACVNAMDLWQFTPLHEAASKNRVEVCSLLLSHGADPTLVNCHGKSAVDMAPTPELRERLTYEFKGHSLLQAAREA 500

T2   343 DVTRIKKHLSLEMVNFKHPQTHETALHCAAASPYPKRKQICELLLRKGANINEKTKEFLTPLHVASEKAHNDVVEVVVKHEAKVNALDNLGQTSLHRAAY 442
         |.. ::||.|..:|||.|||||||||||:|||.|||||:|||||||||||:|||||||||||||||.|||||:|||||.||  ||.|||| ||||||||
T1   501 DLAKVKKTLALEIINFKQPQSHETALHCAVASLHPKRKQVTELLLRKGANVNEKNKDFMTPLHVAAERAHNDVMEVLHKHGAKMNALDTLGQTALHRAAL 600

T2   443 CGHLQTCRLLLSYGCDPNIISLQGFTALQMGNENVQQLLQEGISLGNSEADRQLLEAAKAGDVETVKKLCTVQSVNCRDIEGRQSTPLHFAAGYNRVSVV 542
         .|||||||||||:|.||||:||||||||||:|||:|||.|.:|    || |||:.|:|||:||||:||||||||||||||||:|||||||||||||||
T1   601 AGHLQTCRLLLSYGSDPSIISLQGFTAAQMGNEAVQQILSESTPIRTSDVDYRLLEASKAGDLETVKQLCSSQNVNCRDLEGRHSTPLHFAAGYNRVSVV 700

T2   543 EYLLQHGADVHAKDKGGLVPLHNACSYGHYEVAELLVKHGAVVNVADLWKFTPLHEAAAKGKYEICKLLLQHGADPTKKNRDGNTPLDLVKDGDTDIQDL 642
         ||||.|||||||||||||||||||||||||||||||:||||.|||||||||||||||||||||||||||.|||||||||||||||||||:||||||||
T1   701 EYLLHHGADVHAKDKGGLVPLHNACSYGHYEVAELLVRHGASVNVADLWKFTPLHEAAAKGKYEICKLLLKHGADPTKKNRDGNTPLDLVKEGDTDIQDL 800

T2   643 LRGDAALLDAAKKGCLARVKKLSSPDNVNCRDTQGRHSTPLHLAAGYNNLEVAEYLLQHGADVNAQDKGGLIPLHNAASYGHVDVAALLIKYNACVNATD 742
         |:|||||||||||||||||:.||.| |:|||||||:|||||||||||||||||||||.||||||||||||||||||||||||:||||||||| |||||
T1   801 LKGDAALLDAAKKGCLARVQKLCTPENINCRDTQGRNSTPLHLAAGYNNLEVAEYLLEHGADVNAQDKGGLIPLHNAASYGHVDIAALLIKYNTCVNATD 900

T2   743 KWAFTPLHEAAQKGRTQLCALLLAHGADPTLKNQEGQTPLDLVSADDVSALLTAAMPPSALPSCYKPQVLNGVRSPGATADALSSGPSSPSSLSAASSLD 842
         |||||||||||||||||||||||||||||||:|||||||||| :||| |||  |||   |||.|:||          ..| |.|| ||||||:|
T1   901 KWAFTPLHEAAQKGRTQLCALLLAHGADPTMKNQEGQTPLDLATADDIRALLIDAMPPEALPTCFKPQAT.......VVSASLISPASTPSCLSAASSID 993

T2   843 NLSGSFSELSSVVSSSGTEGASSLEKK..EVPGVDFSITQFVRNLGLEHLMDIFEREQITLDVLVEMGHKELKEIGINAYGHRHKLIKGVERLISGQOGL 940
         ||.| .||.    .|..  |:| ||.| |.|| :||||||:||||||||||||:||||||||||:||||||||||||||||||||||||||||:||||
T1   994 NLTGPLAELAVGGASNAGDGAAGTERKEGEVAGLDMNISQFLKSLGLEHLRDIFETEQITLDVLADMGHEELKEIGINAYGHRHKLIKGVERLLGGQQGT 1093

T2   941 NPYLTLNTSGSGTILIDLSPDDKEFQSVEEEMQSTVREHRDGGHAGGIFNRYNILKIQKVCNKKLWERYTHRRKEVSEENHNANERMLFHGSPFVNAII 1040
         ||||| .    ||||:||.|:||||||||||||||:|||||||||||||||||||||:||||||||||||||||||||||||||||:||||||||||
T1  1094 NPYLTFHCVNQGTILLDLAPEDKEYQSVEEEMQSTIREHRDGGNAGGIFNRYNVIRIQKVVNKKLRERFCHRQKEVSEENHNHHNERMLFHGSPFINAII 1193

T2  1041 HKGFDERHAYIGGMFGAGIYFAENSSKSNQYVYGIGGGTGCPVHKDRSCYICHRQLLFCRVTLGKSFLQFSAMKMAHSPPGHHSVTGRPSVNGLALAEYV 1140
         ||||||||||||||||||||||||||||||||||||||||||:|||||||||||||:||||||||||||::||||||| ||||||:||||||||||||
T1  1194 HKGFDERHAYIGGMFGAGIYFAENSSKSNQYVYGIGGGTGCPTHKDRSCYICHRQMLFCRVTLGKSFLQFSTMKMAHAPPGHHSVIGRPSVNGLAYAEYV 1293

T2  1141 IYRGEQAYPEYLITYQIMRPEGMVDG........ 1166
         ||||||||||||||||||||:||
T1  1294 IYRGEQAYPEYLITYQIMKPEAPSQTATAAEQKT 1327
```

Figure 6(A)

```
1    ...........................................................................................GG 2
101  TCCCCCACTCAGCCCTGGCCTGGCCCCGGGGACCACCCCAGCCTCTCCCACGGCCAGCGGCCTGGCCCCCTTCGCCTCCCCGCGGCACGGCCTAGCGCTG 200

5    CAGGAGGGGCCTTGCCAGCTTCCGCCGCCGCGTCGTTTCAGGACCCGGACGGCGGATTCGCGCTGCCTCCGCCGCCGCGGGGCAGCCGGGGGGCAGGGAG 102
201  CCGGAGGGGGATGGCAGTCGGGATCCGCCCGACAGGCCCCGATCCCCGGACCCGGTT...GACGGTACCAGCTGTTGCAGTACCACCAGCACAATCTGTA 297

103  CCCATCGAGGGGCGCGCGTGGGCGCGGC.CATGGGACTGCGCCGGATCCGGTGACAGCAGGGAGCCAAGCGGCCCGGGCCCTGAGCGCGTCTTC.TCCGG 200
298  CCGTCGCCGCCGCTCCCGTGGTCCCAGCGGTTTCTACTTCATCTGCCGCTGGGGTCGCTCCCAACCCAGCCGGCAGTGGCAGTAACAATTCACCGTCGTC 397

201  GGGGCCTCGCCCTCCTGCTCGCGGGGCCGGGGCTCCTGCTCCGGTTGCTGGCGCTGTTGCTGGCTGTGGCGGCGGCCAGGATCATGTCGGGTCGCCGCTG 300
398  CTCTTCTTCCCCGACTTCTTCCTCATCTTCCTCTCCATCCTCCCCTGGATCGAGCTTGGCGGAGAGCCCCGAGGCGGCCGGAGTTAGCAGCACAGCACCA 497

301  CGCCGGCGGGGGAGCGGCCTGCGCGAGCGCCGCGGCCGAGGCCGTGGAGCCGGCCGCCCGAGAGCTGTTCGAGGCGTGCCGCAACGGGGACGTGGAACGA 400
498  CTGGGGCCTGGG.GCAGCAGGACCTGGGACAGGGGTCCCAGCAGTGAGCGGGGCCCTACGGGAACTGCTGGAGGCCTGTCGCAATGGGGACGTGTCCCGG 596

401  GTCAAGAGGCTGGTGACGCCTGAGAAGGTGAACAGCCGCGACACGGCGGGCAGGAAATCCACCCCGCTGCACTTCGCCGCAGGTTTTGGGCGGAAAGACG 500
597  GTAAAGAGGCTGGTGGACGCGGCAAACGTAAATGCAAAGGACATGGCCGGCCGGAAGTCTTCTCCCCTGCACTTCGCTGCAGGTTTTGGAAGGAAGGATG 696

501  TAGTTGAATATTTGCTTCAGAATGGTGCAAATGTCCAAGCACGTGATGATGGGGGCCTTATTCCTCTTCATAATGCATGCTCTTTTGGTCATGCTGAAGT 600
697  TTGTAGAACACTTACTACAGATGGGTGCTAATGTCCACGCTCGTGATGATGGAGGTCTCATCCCGCTTCATAATGCCTGTTCTTTTGGCCATGCTGAGGT 796

601  AGTCAATCTCCTTTTGCGACATGGTGCAGACCCCAATGCTCGAGATAATTGGAATTATACTCCTCTCCATGAAGCTGCAATTAAAGGAAAGATTGATGTT 700
797  TGTGAGTCTGTTATTGTGCCAAGGAGCTGATCCAAATGCCAGGGATAACTGGAACTATACACCTCTGCATGAAGCTGCTATTAAAGGGAAGATCGATGTG 896

701  TGCATTGTGCTGTTACAGCATGGAGCTGAGCCAACCATCCGAAATACAGATGGAAGGACAGCATTGGATTTAGCAGATCCATCTGCCAAAGCAGTGCTTA 800
897  TGCATTGTGCTGCTGCAGCACGGAGCTGACCCAAACATTCGGAACACTGATGGGAAATCAGCCCTGGACCTGGCAGATCCTTCAGCAAAAGCTGTCCTTA 996

801  CTGGTGAATATAAGAAAGATGAACTCTTAGAAAGTGCCAGGAGTGGCAATGAAGAAAAAATGATGGCTCTACTCACACCATTAAATGTCAACTGCCACGC 900
997  CAGGTGAATACAAGAAAGACGAACTCCTAGAAGCTGCTAGGAGTGGTAATGAAGAAAAACTAATGGCTTTACTGACTCCTCTAAATGTGAATTGCCATGC 1096

901  AAGTGATGGCAGAAAGTCAACTCCATTACATTTGGCAGCAGGATATAACAGAGTAAAGATTGTACAGCTGTTACTGCAACATGGAGCTGATGTCCATGCT 1000
1097 AAGTGATGGGCGAAAGTCGACTCCTTTACATCTAGCAGCGGGCTACAACAGAGTTCGAATAGTTCAGCTTCTTCTTCAGCATGGTGCTGATGTTCATGCA 1196

1001 AAAGATAAAGGTGATCTGGTACCATTACACAATGCCTGTTCTTATGGTCATTATGAAGTAACTGAACTTTTGGTCAAGCATGGTGCCTGTGTAAATGCAA 1100
1197 AAAGACAAAGGTGGACTTGTGCCTCTTCATAATGCATGTTCATATGGACATTATGAAGTCACAGAACTGCTACTAAAGCATGGAGCTTGTGTTAATGCCA 1296

1101 TGGACTTGTGGCAATTCACTCCTCTTCATGAGGCAGCTTCTAAGAACAGGGTTGAAGTATGTTCTCTTCTCTTAAGTTATGGTGCAGACCCAACACTGCT 1200
1297 TGGATCTCTGGCAGTTTACTCCACTGCACGAGGCTGCTTCCAAGAACCGTGTAGAAGTCTGCTCTTTGTTACTTAGCCATGGCGCTGATCCTACGTTAGT 1396

1201 CAATTGTCACAATAAAAGTGCTATAGACTTGGCTCCCACACCACAGTTAAAAGAAAGATTAGCATATGAATTTAAAGGCCACTCGTTGCTGCAAGCTGCA 1300
1397 CAACTGCCATGGCAAAAGTGCTGTGGATATGGCTCCAACTCCGGAGCTTAGGGAGAGATTGACTTATGAATTTAAAGGTCATTCTTTACTACAAGCAGCC 1496

1301 CGAGAAGCTGATGTTACTCGAATCAAAAAACATCTCTCTCTGGAAATGGTGAATTTCAAGCATCCTCAAACACATGAAACAGCATTGCATTGTGCTGCTG 1400
1497 AGAGAAGCAGACTTAGCTAAAGTTAAAAAAACACTCGCTCTGGAAATCATTAATTTCAAACAACCGCAGTCTCATGAAACAGCACTGCACTGTGCTGTGG 1596

1401 CATCTCCATATCCCAAAAGAAAGCAAATATGTGAACTGTTGCTAAGAAAAGGAGCAAACATCAATGAAAAGACTAAAGAATTCTTGACTCCTCTGCACGT 1500
1597 CCTCTCTGCATCCCAAACGTAAACAAGTGACAGAATTGTTACTTAGAAAAGGAGCAAATGTTAATGAAAAAAATAAAGATTTCATGACTCCCCTGCATGT 1696

1501 GGCATCTGAGAAAGCTCATAATGATGTTGTTGAAGTAGTGGTGAAACATGAAGCAAAGGTTAATGCTCTGGATAATCTTGGTCAGACTTCTCTACACAGA 1600
1697 TGCAGCCGAAAGAGCCCATAATGATGTCATGGAAGTTCTGCATAAGCATGGCGCCAAGATGAATGCACTGGACACCCTTGGTCAGACTGCTTTGCATAGA 1796

1601 GCTGCATATTGTGGTCATCTACAAACCTGCCGCCTACTCCTGAGCTATGGGTGTGATCCTAACATTATATCCCTTCAGGGCTTTACTGCTTTACAGATGG 1700
1797 GCCGCCCTAGCAGGCCACCTGCAGACCTGCCGCCTCCTGCTGAGTTACGGCTCTGACCCCTCCATCATCTCCTTACAAGGCTTCACAGCAGCACAGATGG 1896

1701 GAAATGAAAATGTACAGCAACTCCTCCAAGAGGGTATCTCATTAGGTAATTCAGAGGCAGACAGACAATTGCTGGAAGCTGCAAAGGCTGGAGATGTCGA 1800
1897 GCAATGAAGCAGTGCAGCAGATTCTGAGTGAGAGTACACCTATACGTACTTCTGATGTTGATTATCGACTCTTAGAGGCATCTAAAGCTGGAGACTTGGA 1996

1801 AACTGTAAAAAAACTGTGTACTGTTCAGAGTGTCAACTGCAGAGACATTGAAGGGCGTCAGTCTACACCACTTCATTTTGCAGCTGGGTATAACAGAGTG 1900
1997 AACTGTGAAGCAACTTTGCAGCTCTCAAAATGTGAATTGTAGAGACTTAGAGGGCCGGCATTCCACGCCCTTACACTTCGCAGCAGGCTACAACCGCGTG 2096

1901 TCCGTGGTGGAATATCTGCTACAGCATGGAGCTGATGTGCATGCTAAAGATAAAGGAGGCCTTGTACCTTTGCACAATGCATGTTCTTATGGACATTATG 2000
2097 TCTGTTGTAGAGTACCTGCTACACCACGGTGCCGATGTCCATGCCAAAGACAAGGGTGGCTTGGTGCCCCTTCATAATGCCTGTTCATATGGACACTATG 2196

2001 AAGTTGCAGAACTTCTTGTTAAACATGGAGCAGTAGTTAATGTAGCTGATTTATGGAAATTTACACCTTTACATGAAGCAGCAGCAAAAGGAAAATATGA 2100
2197 AGGTGGCTGAGCTTTTAGTAAGGCATGGGGCTTCTGTCAATGTGGCGGACTTATGGAAATTTACCCCTCTCCATGAAGCAGCAGCTAAAGGAAAGTATGA 2296

2101 AATTTGCAAACTTCTGCTCCAGCATGGTGCAGACCCTACAAAAAAAAACAGGGATGGAAATACTCCTTTGGATCTTGTTAAAGATGGAGATACAGATATT 2200
2297 AATCTGCAAGCTCCTTTTAAAACATGGAGCAGATCCAACTAAAAAGAACAGAGATGGAAATACACCTTTGGATTTGGTAAAGGAAGGAGACACAGATATT 2396
```

Figure 6(B)

```
2201 CAAGATCTGCTTAGGGGAGATGCAGCTTTGCTAGATGCTGCCAAGAAGGGTTGTTTAGCCAGAGTGAAGAAGTTGTCTTCTCCTGATAATGTAAATTGCC 2300
2397 CAGGACTTACTGAAAGGGGATGCTGCTTTGTTGGATGCTGCCAAGAAGGGCTGCCTGGCAAGAGTGCAGAAGCTCTGTACCCCAGAGAATATCAACTGCA 2496

2301 GCGATACCCAAGGCAGACATTCAACACCTTTACATTTAGCAGCTGGTTATAATAATTTAGAAGTTGCAGAGTATTTGTTACAACACGGAGCTGATGTGAA 2400
2497 GAGACACCCAGGGCAGAAATTCAACCCCTCTGCACCTGGCAGCAGGCTATAATAACCTGGAAGTAGCTGAATATCTTCTAGAGCATGGAGCTGATGTTAA 2596

2401 TGCCCAAGACAAAGGAGGACTTATTCCTTTACATAATGCAGCATCTTACGGGCATGTAGATGTAGCAGCTCTACTAATAAAGTATAATGCATGTGTCAAT 2500
2597 TGCCCAGGACAAGGGTGGTTTAATTCCTCTTCATAATGCGGCATCTTATGGGCATGTTGACATAGCGGCTTTATTGATAAAATACAACACGTGTGTAAAT 2696

2501 GCCACGGACAAATGGGCTTTCACACCTTTGCACGAAGCAGCCCAAAAGGGACGAACACAGCTTTGTGCTTTGTTGCTAGCCCATGGAGCTGACCCGACTC 2600
2697 GCAACAGATAAGTGGGCGTTTACTCCCCTCCATGAAGCAGCCCAGAAAGGAAGGACGCAGCTGTGCGCCCTCCTCCTAGCGCATGGTGCAGACCCCACCA 2796

2601 TTAAAAATCAGGAAGGACAAACACCTTTAGATTTAGTTTCAGCGGATGATGTCAGCGCTCTTCTGACAGCAGCCATGCCCCCATCTGCTCTGCCCTCTTG 2700
2797 TGAAGAACCAGGAAGGCCAGACGCCTCTGGATCTGGCAACAGCTGACGATATCAGAGCTTTGCTGATAGATGCCATGCCCCCAGAGGCCTTACCTACCTG 2896

2701 TTACAAGCCTCAAGTGCTCAATGGTGTGAGAAGCCCAGGAGCCACTGCAGATGCTCTCTCTTCAGGTCCATCTAGCCCATCAAGCCTTTCTGCAGCCAGC 2800
2897 TTTTAAACCTCA...GGCTACTGTAGTGAG..................TGCCTCTCTGATCTCACCAGCATCCACCCCCTCCTGCCTCTCGGCTGCCAGC 2975

2801 AGTCTTGACAACTTATCTGGGAGTTTTTCAGAACTGTCTTCAGTAGTTAGTTCAAGTGGAACAGAGGGTGCTTCCAGTTTGGAGAAAAAG......GAGG 2894
2976 AGCATAGACAACCTCACTGGCCCTTTAGCAGAGTTGGCCGTAGGAGGAGCCTCCAATGCAGGGGATGGCGCCGCGGGAACAGAAAGGAAGGAAGGAGAAG 3075

2895 TTCCAGGAGTAGATTTTAGCATAACTCAATTCGTAAGGAATCTTGGACTTGAGCACCTAATGGATATATTTGAGAGAGAACAGATCACTTTGGATGTATT 2994
3076 TTGCTGGTCTTGACATGAATATCAGCCAATTTCTAAAAAGCCTTGGCCTTGAACACCTTCGGGATATCTTTGAAACAGAACAGATTACACTAGATGTGTT 3175

2995 AGTTGAGATGGGGCACAAGGAGCTGAAGGAGATTGGAATCAATGCTTATGGACATAGGCACAAACTAATTAAAGGAGTCGAGAGACTTATCTCCGGACAA 3094
3176 GGCTGATATGGGTCATGAAGAGTTGAAAGAAATAGGCATCAATGCATATGGGCACCGCCACAAATTAATCAAAGGAGTAGAAAGACTCTTAGGTGGACAA 3275

3095 CAAGGTCTTAACCCATATTTAACTTTGAACACCTCTGGTAGTGGAACAATTCTTATAGATCTGTCTCCTGATGATAAAGAGTTTCAGTCTGTGGAGGAAG 3194
3276 CAAGGCACCAATCCTTATTTGACTTTTCACTGTGTTAATCAGGGAACGATTTTGCTGGATCTTGCTCCAGAAGATAAAGAATATCAGTCAGTGGAAGAAG 3375

3195 AGATGCAAAGTACAGTTCGAGAGCACAGAGATGGAGGTCATGCAGGTGGAATCTTCAACAGATACAATATTCTCAAGATTCAGAAGGTTTGTAACAAGAA 3294
3376 AGATGCAAAGTACTATTCGAGAACACAGAGATGGTGGTAATGCTGGCGGCATCTTCAACAGATACAATGTCATTCGAATTCAAAAAGTTGTCAACAAGAA 3475

3295 ACTATGGGAAAGATACACTCACCGGAGAAAAGAAGTTTCTGAAGAAAACCACAACCATGCCAATGAACGAATGCTATTTCATGGGTCTCCTTTTGTGAAT 3394
3476 GTTGAGGGAGCGGTTCTGCCACCGACAGAAGGAAGTGTCTGAGGAGAATCACAACCATCACAATGAGCGCATGTTGTTTCATGGTTCTCCTTTCATTAAT 3575

3395 GCAATTATCCACAAAGGCTTTGATGAAAGGCATGCGTACATAGGTGGTATGTTTGGAGCTGGCATTTATTTTGCTGAAAACTCTTCCAAAAGCAATCAAT 3494
3576 GCCATTATTCATAAAGGGTTTGATGAGCGACATGCATACATAGGAGGAATGTTTGGGGCCGGGATTTATTTTGCTGAAAACTCCTCAAAAAGCAACCAAT 3675

3495 ATGTATATGGAATTGGAGGAGGTACTGGGTGTCCAGTTCACAAAGACAGATCTTGTTACATTTGCCACAGGCAGCTGCTCTTTTGCCGGGTAACCTTGGG 3594
3676 ATGTTTATGGAATTGGAGGAGGAACAGGCTGCCCTACACACAAGGACAGGTCATGCTATATATGTCACAGACAAATGCTCTTCTGTAGAGTGACCCTTGG 3775

3595 AAAGTCTTTCCTGCAGTTCAGTGCAATGAAAATGGCACATTCTCCTCCAGGTCATCACTCAGTCACTGGTAGGCCCAGTGTAAATGGCCTAGCATTAGCT 3694
3776 GAAATCCTTTCTGCAGTTTAGCACCATGAAAATGGCCCACGCGCCTCCAGGGCACCACTCAGTCATTGGTAGACCGAGCGTCAATGGGCTGGCATATGCT 3875

3695 GAATATGTTATTTACAGAGGAGAACAGGCTTATCCTGAGTATTTAATTACTTACCAGATTATGAGGCCTGAAGGTATGGTCGATGGATAAATAGTTATTT 3794
3876 GAATATGTCATCTACAGAGGAGAACAGGCATACCCAGAGTATCTTATCACTTACCAGATCATGAAGCCAGAAGCCCCTTCCCAGACCGCAACAG...CCG 3972

3795 TAAGAAACTAATTCCACTGAACCTAAAATCATCAAAG.CAGCAGTGGCCTCTACGTTTTACTCCTTTGCTGAAAAAAAATCATCTTGCCCACAGGCCTGT 3893
3973 CAGAGCAGAAGACCTAGTGAATGCCTGCTGGTGAAGGCCAGATCAGATTTCAACCTGGGACTGGATTACAGAGGATTGTTTCTAATAACAACATCAATAT 4072

3894 GGCAAAAGGATAAAAATGTGAACGAAGTTTAACATTCTGACTTGATAAAGCTTTAATAATGTACAGTGTTTTCTAAATATTTCCTGTTTTTTCAGCACTT 3993
4073 TCTAGAAGTCCCTGACAGCCTA.GAAATAAGCTGTTTGTCTTCTATAAAGCATTGCTATAGTG.......................................... 4134
```

SECOND MAMMALIAN TANKYRASE

RELATED APPLICATIONS

This application is a continuation of PCT/US00/09558, an International patent application designating the U.S., filed on Apr. 10, 2000, and published on Oct. 19, 2001 as WO 00/61813. Both the PCT application and this continuation claim the priority basis of U.S. Provisional Patent Application Nos. 60/128,577, filed Apr. 9, 1999; and 60/129,123, filed Apr. 13, 1999. The aforelisted priority documents are hereby incorporated herein by reference in their entirety.

TECHNICAL FIELD

This invention relates generally to the field of molecular biology of telomere and telomere associated proteins, and the maintenance of telomere structure. More specifically, this invention relates to a novel protein that shares three domains of homology with the telomerase associated protein Tankyrase I.

BACKGROUND

Recent research has described what may be a key switch in the control of cellular aging. The telomeres at chromosome ends are made up of multiple repeats of the DNA sequence TTAGGG, which are thought to stabilize the chromosome during replication. Telomeres shorten each time the cell divides, and cells become senescent when the telomeres are too short to protect the chromosome. But in some cells, including embryonic cells, an enzyme called telomerase rebuilds the telomeres after each division, extending the replicative capacity of the cell. (Bodnar et al., Science 279:349, 1998; Harley et al., Curr. Opin. Genet. Dev. 5:249,1995).

Regulation of telomerase activity is a complex process involving several protein components. Two such proteins have DNA binding activity, and are named telomeric repeat binding factors (TRF1 and TRF2). It is thought that TRF1 is involved in regulating telomere length, because overexpression of wild-type TRF1 makes telomeres shorter, while overexpression of a dominant-negative form of TRF1 makes telomeres longer—perhaps by affecting the access of telomerase to the chromosome terminus (van Steensel et al., Nature, 385:740, 1997). TRF1 promotes parallel pairing of telomeric tracts, apparently pairing in parallel homodimers that form filamentous structures on longer telomeric repeat arrays (Griffith et al., J. Mol. Biol. 278:79–88, 1998).

The role of TRF2 appears to be protection of the chromosome terminus, since expression of a dominant-negative form of TRF2 leads to chromosome—chromosome fusions. (Griffith et al., J Mol Biol. 278:79, 1998; Broccoli et al., Nature Genetics 17:231, 1997; van Steensel et al., Cell 92:401, 1998). This in turn leads to p53—and ATM-dependent apoptosis of the cell (Karlseder et al., Science 283:1321, 1999). TRF1 and TRF2 have been implicated in large duplex loops at the end of telomeres that may provide a general mechanism for telomere protection and replication (Griffith et al., Cell 97:503, 1999).

Smith et al. (Science 282:1484, 1998; Genomics 57:320, 1999; J. Cell Sci. 112:3649, 1999) have reported a novel protein that associates with TRF1, which they named "Tankyrase". A yeast two-hybrid screen was used with human TRF1 as bait, and yielded two overlapping cDNAs which provided the full-length sequence. Northern blot analysis revealed that multiple mRNAs were ubiquitously expressed in human tissues, with the highest amounts detectable in testes. It has been proposed that tankyrase interferes with the binding of TRF1 to telomeres, which in turn has an effect on telomere length. Tankyrase co-localizes with TRF1 at the ends of human chromosomes in metaphase and interphase, and also resides at nuclear pore complexes and centrosomes. Smith et al. reported that the gene for tankyrase is positioned at 17.6 $cR_{10000}$ on human chromosome 8 with a LOD of 8.2 on the G3 map.

The molecular events involved in managing chromosome structure and regulating cell senescence are extremely complex. Each new protein found to participate in this process provides new opportunities for monitoring and intervening in some of the fundamental events of cell biology.

SUMMARY OF THE INVENTION

This invention provides a new human protein which is hereby designated Tankyrase II. This new protein shares three domains with the Tankyrase protein of Smith et al.: the ANK domain comprising 24 repeats of the ankyrin motif, the SAM domain thought to be involved in protein—protein interaction, and the PARP domain that is responsible for the poly(ADP-ribose) polymerase activity. Tankyrase II further comprises has a new domain at the N-terminal, designated the GC domain, which has no known homologs.

One of the embodiments of this invention is an isolated polynucleotide having at least about 30 consecutive nucleotides contained in a human Tankyrase II encoding sequence, or that is contained in plasmids deposited under Accession No. 203919, or that hybridizes under stringent conditions to a Tankyrase II encoding sequence, but does not consist of the encoding sequence for human Tankyrase I or other previously known structurally related proteins, such as those having PARP activity. Another embodiment of this invention is an isolated polynucleotide having at least 100 consecutive nucleotides that is at least 90% identical to a Tankyrase II sequence, or contained in the deposited plasmids, but not in λ-phage, Tankyrase I, or other previously known sequences. Certain polynucleotides of this invention encode a protein comprising a GC domain, a PARP domain, a SAM domain, or an ANK domain, or a protein that binds other telomere-associated proteins like TRF1, TRF2, TIN2, and Tankyrase I, or that ADP-ribosylates a target protein in the presence of $NAD^+$. Polynucleotides of this invention can be used to obtain the encoded polypeptide, or to determine other polynucleotides that encode Tankyrase II-like protein.

Another embodiment of this invention is an isolated polypeptide comprising a sequence of at least 10 consecutive amino acids that is contained in Tankyrase II, or is contained in the deposited plasmids, but is not contained in any previously known peptide sequence. Another embodiment of this invention is an isolated polypeptide comprising a sequence of at least 25 consecutive amino acids that is at least 90% identical to a Tankyrase II protein sequence, or a protein sequence encoded in the deposited plasmids. Certain polypeptides of this invention comprise a GC domain, a PARP domain, a SAM domain, or an ANK domain, or have activity for binding other telomere-associated proteins like TRF1, TRF2, TIN2, and Tankyrase I, or ADP-ribosylate a target protein in the presence of $NAD^+$.

A further embodiment of this invention is an isolated human Tankyrase II protein or fragment thereof, at least 10-fold higher in purity (or more) on a weight per weight basis than what occurs in natural sources.

Also embodied in this invention are polynucleotides encoding the polypeptides of this invention, and antibodies of any sort that bind specifically to the polypeptides of this invention. Some of the antibodies inhibit the catalytic activity of Tankyrase II; inhibit the binding of Tankyrase II to other telomere associated protein; or inhibit protein ribosylation mediated by Tankyrase II. Peptides can be obtained by expressing a polynucleotide of the invention in a suitable host cell. Also provided are means for obtaining any antibody of this invention, comprising immunizing an animal or contacting an immunocompetent particle with a polypeptide of this invention. Peptides of this invention can be isolated from a mixture by using an antibody as a specific adsorbant; conversely, antibodies of this invention can be isolated using a peptide epitope as a specific adsorbant.

A further embodiment of this invention is a method for ribosylating a target protein, comprising incubating the target protein with a peptide of this invention in the presence of $NAD^+$.

Assay methods of this invention include determining Tankyrase II binding activity by incubating with a peptide of this invention under conditions where the protein can bind the peptide specifically to form a complex, and then correlating any complex formed with the presence or amount of the protein in the sample. The protein that has Tankyrase II binding activity can optionally be TRF1, TRF2, TIN2, or Tankyrase I.

Another assay method of this invention is for screening a test compound to determine an ability to affect Tankyrase II activity, comprising incubating the compound with containing a peptide of this invention and a conjugate binding ligand, and determining any effect of the test compound on complex formation. Another such method comprises incubating a test compound with a peptide of this invention, a potential target protein, and $NAD^+$; then determining any effect of the test compound on the amount or rate of ribosylation of the target.

This invention also includes a method for modulating Tankyrase II expression in a cell, comprising contacting the cell with the polynucleotide of this invention such as an antisense polynucleotide, a ribozyme, or an inhibitory RNA under conditions where the polynucleotide can interfere with mRNA translation. Modulating Tankyrase II expression in turn is believed to modulate telomere length in the cell.

These and other embodiments of the invention will be apparent from the description that follows.

BRIEF DESCRIPTION OF THE FIGURES

FIGS. 2, 3, and 4 are sequence listings showing cDNA and amino acid sequence data for human Tankyrase II (SEQ. ID NOs: 1 to 6). The data from FIGS. 2–3 were obtained as described in Examples 1–4; the data from FIG. 4 were obtained as described in Examples 6–7.

FIG. 5 is a sequence listing comparing Tankyrase II (SEQ. ID NO:6) with its closest known intraspecies homolog, Tankyrase I (SEQ. ID NO:8), at the protein level.

FIG. 6 is a sequence listing comparing Tankyrase II (SEQ. ID NO:5) with Tankyrase I (SEQ. ID NO:7), at the cDNA level.

DETAILED DESCRIPTION OF THE INVENTION

Figure 1:
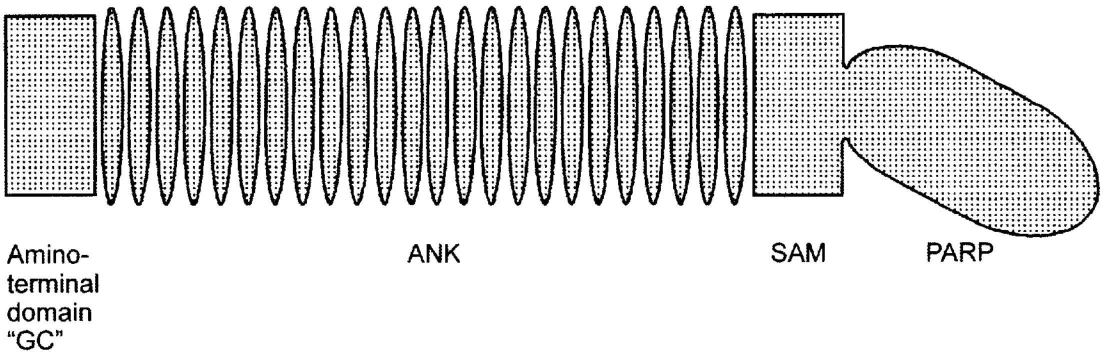
FIG. 1 is a schematic depiction of Tankyrase II protein. The domains depicted are the GC domain (encoded by a gene segment rich in GC), the ANK domain, containing contains 24 ankyrin repeats thought to be involved in protein—protein interaction, the sterile alpha motif (SAM) domain, thought to be involved in cellular signaling, and the poly (ADP)-ribose polymerase (PARP) domain, with enzymatic activity for ribosylating target proteins such as TRF1.

This disclosure describes the newly discovered protein Tankyrase II. Polynucleotides, polypeptides, and antibodies related to Tankyrase II are provided and exemplified. The protein has enzymatic activity that causes ribosylation of proximal target proteins using NAD as substrate. Tankyrase II is thought to have binding activity for other telomere-associated proteins, which could become ribosylated targets of the enzyme. This in turn could play a role in the regulation of telomere length, thereby affecting the replicative capacity of the cell. The techniques and materials in this disclosure provide the means to model Tankyrase II activity in vitro, and provide a way to monitor and modulate Tankyrase II activity in vivo. Modulation of Tankyrase II activity may be used to regulate telomerase activity or telomere length.

FIG. 1 shows the structurally distinct domains of Tankyrase II, which provide different functional features of tankyrase activity. There is a unique amino-terminal (GC) domain, followed by an ankyrin (ANK) motif domain, a sterile alpha module (SAM) domain, and a carboxy-terminal poly(ADP) ribose polymerase (PARP) domain.

The ankyrin (ANK) domain of Tankyrase II contains 24 ankyrin repeats—a motif of about 33 residues found in a number of different proteins, and thought to act as modular adapters for heterologous protein—protein interactions (reviewed by Bennett et al., J. Biol. Chem. 267:8703, 1992; Bennett et al., and Michaely, TICB 2:127, 1992; Bork et al., Proteins: Structure, Function, & Genetics 17:363, 1993). A correlation has been observed between the number of ankyrin repeats and the nature of the protein—protein association. Ankyrin family members containing 24 ankyrin repeats bind cytoskeletal proteins such as tubulin and spectrin.

The sterile alpha motif (SAM) domain of Tankyrase II lies downstream from the ANK domain. SAM domains are found in signaling proteins such as transcription factors, serine/threonine protein kinases, and GTPases, (Stapleton et al., 1999, Nature Struct. Biol. 6:44–9; Thamos et al., 1999, Science 283: 833–36). SAM-containing proteins form hetero- and homo-dimers with other SAM-containing proteins that can regulate cellular signaling processes.

The carboxy-terminus of Tankyrase II is a domain homologous to other proteins with poly (ADP)-ribose polymerase activity, referred to as the PARP domain. Proteins that contain a PARP domain catalyze the addition of long branched chains of ADP-ribose to target proteins, using nicotinamide adenine dinucleotide ($NAD^+$) as a substrate (reviewed by Still et al., Genomics 62:533, 1999; de Murcia et al., Trends Biochem. Sci. 19:172, 1994; Lindahl et al., Trends Biochem. Sci. 20:405, 1995). The first such protein, PARP-1 (Adprt1) contains DNA-binding zinc fingers, a nuclear localization sequence, and an automodification domain. PARP-1 binds to nicked DNA, and is thought to play a role in chromosomal damage repair (P. A. Jeggo, Current Biol. 8:R49, 1998). PARP-2 (AdprtL2) is a homologous protein with ribosylation activity that also binds damaged DNA (Amé et al. J. Biol. Chem. 274:17860, 1999). VPARP is a related protein that ribosylates major vault protein in the mammalian ribonucleoprotein complex (Kickhoefer, J. Cell Biol. 146:917, 1999). Other members of the PARP family include Tankyrase I and AdprtL1 (Still et al., supra).

The presence of the ANK, SAM and PARP domains in Tankyrase II suggests that Tankyrase II plays a role in intercellular or intracellular communication (e.g., signal transduction), possibly in conjunction with proteins involved in DNA repair pathways or maintenance of telomeres. Ribosylation can also play an important role in how Tankyrase II regulates other proteins involved in telomere management. Ribosylation of telomere-associated proteins may result in them leaving the telomere, potentially modulating the activity of telomerase reverse transcriptase, and thereby affecting telomere length and replicative capacity of the cell.

The SAM, PARP and ANK domains of Tankyrase II are homologous to counterpart domains in the Tankyrase I protein. However, the N-terminal domains appear to have no homology. Tankyrase I has a 180-residue HPS domain, so called for the abundance of histidine, proline, and serine residues. In contrast, Tankyrase II has a substantially different amino acid composition, encoded by a highly GC-rich gene sequence. This N-terminal domain of Tankyrase II will be referred to in this disclosure as the "Divergent" or "GC" domain.

There is a relationship between the attainment of a critical telomere length in dividing somatic cells and DNA damage, and both processes lead to cell cycle arrest and the activation of gene expression pathways. Thus, Tankyrase II may communicate with a subset of the signaling molecules in DNA repair processes to initiate the specific arrest and gene activation pathways of cellular senescence. Notably, Tankyrase I has been demonstrated to ribosylate both itself and TRF1 (Smith et al., 1998, supra), resulting in a reduction of the ability of TRF1 to bind telomeric DNA. The link between telomere structure and DNA repair is supported by the observation that p53-and ATM (ataxia telangiectasia mutated) dependent apoptosis is induced by telomeres with attenuated TRF2 function (Karlseder et al., 1999, Science 283:1321–1325).

The structural features of Tankyrase II indicate that it binds to nuclear and cell proteins, and is involved in intercellular or intracellular cell signaling that affect telomere structure and metabolism. Compositions and treatments that modulate Tankyrase II expression or function are likely to be of therapeutic benefit for cancer, disorders associated with replicative senescence, and other conditions associated with perturbations of telomerase activity or telomere length.

Definitions

The term "polynucleotide" as used in this disclosure refers to a polymeric form of nucleotides of any length. Included are genes and gene fragments, mRNA, tRNA, rRNA, ribozymes, cDNA, recombinant polynucleotides, branched polynucleotides, plasmids, vectors, isolated DNA and RNA, nucleic acid probes, and primers. Also included are nucleotide analogs, including but not limited to thiol-derivatized nucleosides (U.S. Pat. No. 5,578,718), oligonucleotides with modified backbones (U.S. Pat. Nos. 5,541,307 and 5,378,825), and peptide nucleic acids (U.S. Pat. No. 5,786,461). The term polynucleotide, as used in this disclosure, refers interchangeably to double- and single-stranded molecules. Unless otherwise specified or required, any embodiment of the invention that is a polynucleotide encompasses both a double-stranded form, and each of the two complementary single-stranded forms known or predicted to make up the double-stranded form.

The term "oligonucleotide" is reserved for polynucleotides of no more than 100 bases in length, and may or may not be accompanied with an antisense strand, depending on context. Oligonucleotides are often used as probes in specific hybridization reactions, or as primers in amplification reactions.

When comparison is made between polynucleotides for degree of identity, it is implicitly understood that complementary strands are easily generated, and the sense or antisense strand is selected or predicted that maximizes the degree of identity between the polynucleotides being compared. Percentage of sequence identity is calculated by first aligning the polynucleotide being examined with the reference counterpart, and then counting the number of residues shared between the sequences being compared as a percentage of the region under examination. No penalty is imposed for the presence of insertions or deletions, but insertions or deletions are permitted only where clearly required to readjust the alignment. The percentage is given in terms of residues in the sequence being examined that are identical to residues in the comparison or reference sequence. Particularly desirable polynucleotide sequences preserve at least one function of the prototype. By way of example and depending on context, the function preserved may include an ability to hybridize with a target sequence, the function of a polypeptide it may encode, or (for certain gene targeting vectors) the ability to facilitate homologous recombination or gene inactivation. An example of an algorithm suitable for finding homologous sequences and determining percent sequence identity is the BLAST algorithm, (Altschul et al., 1990, J. Mol. Biol. 215:403, 1990; Karlin et al., Proc. Natl. Acad. Sci. USA 90:5873, 1993), available through the National Center for Biotechnology Information (www.ncbi.nlm.nih.gov/entrez).

Polynucleotide sequences are said to be in a "non-natural arrangement" when they are joined together or interposed with another sequence in an arrangement not found in nature.

"Hybridization" refers to a reaction in which one or more polynucleotides react to form a complex that is stabilized via hydrogen bonding between the bases of the nucleotide residues. The hydrogen bonding can occur by Watson-Crick base pairing, Hoogsteen binding, triplex formation, or complexing in any other sequence-specific manner. A hybridization reaction will, on occasion, be a step in a more extensive process, such as part of PCR amplification. Hybridization reactions can be performed under conditions of different "stringency". Conditions that increase the stringency of a hybridization reaction are widely known (see e.g., Sambrook et al., infra). Examples of conditions in order of increasing stringency: incubation temperatures of 25° C., 37° C., 50° C., and 68° C.; concentrations of 10×SSC, 6×SSC, 1×SSC, 0.1×SSC (where SSC is 0.15 M NaCl and 15 mM citrate buffer, pH 7.2) and their equivalent using other buffer systems; formamide concentrations of 0%, 25%, 50%, and 75%; incubation times from 5 min to 24 h; 1, 2, or more washing steps; wash incubation times of 1, 5, or 15 min; and wash solutions of 6×SSC, 1×SSC, 0.1×SSC, or deionized water. Typical conditions of high stringency for the binding of a probe of about 100 base pairs and above is a hybridization reaction at 65° C. in 2×SSC, followed by repeat washes at 0.1×SSC—or the equivalent combination of solvent and temperature conditions for the particular nucleic acids being studied.

A "hybrid" of polynucleotides, or a "complex" formed between any two or more components in a biochemical reaction (such as antibody and antigen), refers to a duplex or higher-order complex that is sufficiently long-lasting to persist between its formation and subsequent detection.

A "control element" or "control sequence" is a nucleotide sequence involved in an interaction of molecules that contributes to the functional regulation of a polynucleotide, including replication, duplication, transcription, splicing, translation, or degradation of the polynucleotide. "Operatively linked" refers to an operative relationship between genetic elements, in which the function of one element influences the function of another element. For example, an expressible encoding sequence may be operatively linked to control element that permit transcription and translation.

The terms "polypeptide", "peptide" and "protein" are used interchangeably in this disclosure to refer to polymers of amino acids of any length. The polymer may comprise modified amino acids, it may be linear or branched, and it may be interrupted by non-amino acids. The terms also encompass an amino acid polymer that has been modified naturally or by intervention; for example, disulfide bond formation, glycosylation, lipidation, acetylation, and/or phosphorylation.

Percentage of sequence identity is calculated for polypeptides by first aligning the polypeptide being examined with the reference counterpart or prototype, and then counting the number of residues shared between the sequences being compared as a percentage of the region under examination. No penalty is imposed for the presence of insertions or deletions, but insertions or deletions are permitted only where clearly required to readjust the alignment. The percentage is given in terms of residues in the sequence being examined that are identical to residues in the comparison or reference sequence. Where substitutions are made, conservative substitutions (in which one amino acid is substituted by another with similar charge, size, hydrophobicity, or aromaticity) are typically better tolerated. Desirable sequences preserves the function of the prototype: for example, the enzymatic activity, the binding of specific substrates, and the binding of specific antibody as detectable in a standard competition inhibition immunoassay. In certain embodiments, the identity may exist over a region that is at least about 10, 20–25, or 50–100 amino acids in length.

The term "antibody" as used in this disclosure refers to both polyclonal and monoclonal antibody of any species. The ambit of the term deliberately encompasses not only intact immunoglobulin molecules, but also such fragments and genetically engineered derivatives of immunoglobulin molecules (including humanized forms) that may be prepared by techniques known in the art, and retaining the binding specificity of the antigen binding site.

An "immunogenic" compound or composition is capable of stimulating production of a specific immunological response when administered to a suitable host, usually a mammal.

An "isolated" polynucleotide, polypeptide, protein, antibody, or other substance refers to a preparation of the substance devoid of at least some of the other components that may also be present where the substance or a similar substance naturally occurs or is initially obtained from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Enrichments by 2, 10, 100, and 1000 fold achieve improved degrees of purification. A substance can also be provided in an isolated state by a process of artificial assembly, such as by chemical synthesis or recombinant expression. An "isolated" cell is a cell that has been separated from the organism in which it was grown.

A polynucleotide used in a reaction, such as a probe used in a hybridization reaction or a vector used in gene targeting is referred to as "specific" or "selective" if it hybridizes or reacts with the intended target more frequently, more rapidly, or with greater duration than it does with alternative substances. Similarly, a polypeptide is referred to as "specific" or "selective" if it binds an intended target, such as a ligand, hapten, substrate, antibody, or other polypeptide more frequently, more rapidly, or with greater duration than it does to alternative substances. An antibody is referred to as "specific" or "selective" if it binds via at least one antigen recognition site to the intended target more frequently, more rapidly, or with greater duration than it does to alternative substances.

General Techniques

Unless otherwise noted, the practice of this invention can be carried out by employing standard techniques of genetic engineering, protein manipulation, and cell culture. Textbooks that describe standard laboratory techniques include "*Molecular Cloning: A Laboratory Manual*", 2nd Ed. (Sambrook et al., 1989); "*Oligonucleotide Synthesis*" (M. J. Gait, ed., 1984); "*Animal Cell Culture*" (R. I. Freshney, ed., 1987); the series "*Methods in Enzymology*" (Academic Press, Inc.); "*Gene Transfer Vectors for Mammalian Cells*" (J. M. Miller & M. P. Calos, eds., 1987); "*Current Protocols in Molecular Biology*" and "*Short Protocols in Molecular Biology, 3rd Edition*" (F. M. Ausubel et al., eds., 1987 & 1995); and "*Recombinant DNA Methodology II*" (R. Wu ed., Academic Press 1995). Techniques used in raising, purifying and modifying antibodies, and the design and execution of immunoassays, are described in *Handbook of Experimental Immunology* (D. M. Weir & C. C. Blackwell, eds.); *The Immunoassay Handbook* (Stockton Press NY, 1994); and R. Masseyeff, W. H. Albert, and N. A. Staines, eds., *Methods of Immunological Analysis* (Weinheim: VCH Verlags GmbH, 1993).

Polynucleotides

The polynucleotides of this invention include those containing nucleotide sequences which are found within the Tankyrase II DNA sequence, shown in SEQ. ID NOs:1, 3, and 5. Further sequence for Tankyrase II gene can be obtained by employing standard sequencing techniques known in the art to the phage plasmids deposited in support of this application.

Also included in this invention are polynucleotides that are from naturally occurring allelic variants, synthetic variants, and homologs of Tankyrase II with a percentage of residues identical to the Tankyrase II cDNA or gene sequence, determined as described above. It is understood that substitutions, insertions, and deletions can be accommodated within a polynucleotide sequence without departing from the spirit of this invention. In certain embodiments, the polynucleotide sequences are at least about 80%, 90%, 95%, or 98% identical to a sequence or part of a sequence exemplified in this disclosure; in order if increasing preference. In other embodiments, the polynucleotide sequences are 100% identical to a reference sequence or a fragment thereof. The length of consecutive residues in the identical or homologous sequence compared with the exemplary sequence can be at least about 15, 30, 50, 75, 100, 200 or 500 residues in order of increasing preference, up to the length of the entire clone, gene, or sequence.

This invention includes polynucleotides that are uniquely related to the prototype polynucleotide sequences, in comparison with other sequences that may be present in a sample or reaction mixture of interest. By way of example, probes of at least about 100 consecutive nucleotides that are at least 90% or 80% identical to a reference sequence may be specific, and a probe of at least about 500 or 2000 consecutive nucleotides may be specific if at least 90%, 80%, 70%, or even 60% identical with the reference sequence, depending on hybridization conditions, as explained below. On occasion, such nucleotides can be divided into halves (about nucleotides 1–2137 and 2138–4275), or quarters (about 1–1068; 1069–2137; 2138–3206; 3207–4275), and still retain their specificity. Nucleic acid molecules comprising specified lengths of consecutive nucleotides can be selected from any of these regions. It will also be recognized that for some purposes such as hybridization reactions, a specific polynucleotide sequence will readily accommodate deletions from the 5' or 3' end of either strand of say, 15, 25, or even 50 nucleotides without compromising function. Internal deletions may also be tolerated.

Of particular interest are polynucleotides that are distinct from polynucleotides encoding Tankyrase I, and other proteins containing ANK, PARP, or SAM domains. In certain embodiments of the invention, polynucleotides are distinct from one or more previously known EST sequences, such as those in GenBank Accession Nos. R64714, AA244138 (SEQ. ID NO:9), A244137, AA307492, H11865, H17748, N57467, R06946, AI247608 R06902, AI247608, H11505, H17635, N29528, AA088990 AI426537, and AW157349 (SEQ. ID NO:10), and those listed elsewhere in this disclosure. A polynucleotide of this invention can be "distinct" from other polynucleotides because of an internal sequence difference (a substitution, deletion, or insertion), or because it is defined to encompass additional sequence at either end. Also included in the invention are recombinant or synthetic polynucleotides in which a Tankyrase II-like sequence is linked to a heterologous sequence to form: for example, a heterologous promoter in an expression vector, or a selectable marker such as neo in a targeting vector.

The polynucleotides of this invention can be in the form of an expression vector, in which the encoding sequence is operatively linked to control elements for transcription and translation in a prokaryotic or eukaryotic host cell of interest. A variety of suitable vectors and their design and manufacture are known in the art. Vector systems of interest include but are not limited to those based on retroviruses, adenoviruses, adenoassociated viruses, herpes viruses, SV40, papilloma virus, Epstein Barr virus, vaccinia virus, lenti virus, and Semliki Forest virus.

Particular polynucleotides of this invention are useful for producing polypeptides of interest, as nucleotide probes and primers, and as targeting vectors for genetic knockouts. Further description of the characteristics of such constructs are provided elsewhere in this disclosure.

Preparation

The polynucleotides of this invention can be prepared by any suitable technique in the art. Using the data provided in this disclosure or deduced from the deposited plasmids, sequences of less than ~50 base pairs are conveniently prepared by chemical synthesis, either through a commercial service or by a known synthetic method, such as the triester method or the phosphite method. A suitable method is solid phase synthesis using mononucleoside phosphoramidite coupling units (Hirose et al., *Tetra. Lett.* 19:2449–2452, 1978; U.S. Pat. No. 4,415,732).

For use in antisense therapy, polynucleotides can be prepared synthetically that are more stable for the pharmaceutical preparation for which they are intended. Non-limiting examples include thiol-derivatized nucleosides (U.S. Pat. No. 5,578,718), oligonucleotides with modified backbones (U.S. Pat. Nos. 5,541,307 and 5,378,825). Also of interest in the context of antisense constructs are peptide nucleic acids. Prototype PNA have an achiral polyamide backbone consisting of N-(2-aminoethyl)glycine units, to which purine and pyrimidine bases are linked, for example, by way of a methylene carbonyl linker. PNAs are nuclease and protease resistant, and the uncharged nature of the PNA oligomers enhances the stability of PNA-nucleotide duplexes, thereby blocking transcription or translation. Uptake into cells can be enhanced by conjugating to lipophilic groups incorporating into liposomes, and introducing an amino acid side chain into the PNA backbone. See Soomets et al., Front. Biosci. 4:D782, 1999; U.S. Pat. Nos. 5,539,082, 5,766,855, 5,786,461, and International Patent Application WO 8/53801.

Polynucleotides of this invention can also be obtained by PCR amplification of a template with the desired sequence. Oligonucleotide primers spanning the desired sequence are annealed to the template, elongated by a DNA polymerase, and then melted at higher temperature so that the template and elongated oligonucleotides dissociate. The cycle is repeated until the desired amount of amplified polynucleotide is obtained (U.S. Pat. Nos. 4,683,195 and 4,683,202). Exemplary primers are shown in Table 1. Suitable templates include the plasmids deposited in support of this application, and cDNA libraries for cells expressing Tankyrase II. Encoding sequences, intron sequences, and upstream or downstream sequences for Tankyrase II can be obtained from a human genomic DNA library.

TABLE 1

Exemplary primers for amplifying Tankyrase II sequences

| Forward & Reverse Primers | | | Function |
|---|---|---|---|
| UTANKII-32: | 5'-TCCAGAGGCTGGTGACCCCTGA-3' | SEQ. ID NO:11 | Amplifies entire |
| LTANKII-37: | 5'-TTGAACTAACTACTGAAGA-3' | SEQ. ID NO:12 | ANK domain |
| UTANKII-38: | 5'-CTGTCTTCAGTAGTTAGTTCA-3' | SEQ. ID NO:13 | Amplifies entire |
| LTANKII-39: | 5'-GTTACAAACCTTCTGAATCT-3' | SEQ. ID NO:14 | SAM domain |
| UTANKII-40: | 5'-GAAAGATACACTCACCGGA-3' | SEQ. ID NO:15 | Amplifies entire |
| LTANKII-41: | 5'-TAGGGTTCAGTGGGAATTAG-3' | SEQ. ID NO:16 | PARP domain |
| gt11-5': | 5'GACTCCTGGAGCCCGTCA-3' | SEQ. ID NO:17 | Amplifies λ 11L-1-1 |
| gt11-3': | 5'-GGTAGCGACCGGGCGTCA-3' | SEQ. ID NO:18 | cDNA insert |

Production scale amounts of large polynucleotides are most conveniently obtained by inserting the desired sequence into a suitable cloning vector and reproducing the clone. Techniques for nucleotide cloning are given in Sambrook, Fritsch & Maniatis (supra) and in U.S. Pat. No. 5,552,524. Exemplary cloning and expression methods are illustrated in Examples 1 and 2, below. Polynucleotides can be purified by standard techniques in nucleic acid chemistry, such as phenol-chloroform extraction, agarose gel electrophoresis, and other techniques known in the art, adapted according to the source of the polynucleotide.

Assessment and use of the Polynucleotides

Polynucleotides of this invention can be used to identify Tankyrase II nucleotide sequences in a sample of interest for research, diagnostic evaluation, or any other purpose. Generally, this will involve preparing a reaction mixture in which a sample suspected of containing an Tankyrase II-related sequence is contacted with a polynucleotide of this invention under conditions that permit the polynucleotide to hybridize specifically with the compound being tested for, detecting any stable hybrids that form, and correlating the hybrids with the presence of a Tankyrase II related sequence in the sample. The formation of stable hybrids can be detected by any suitable method known in the art. For example, the probe sequence with a detectable label such as a radioisotope, a chromophore, or a hapten such as avidin to which an signaling reagent can be attached. Alternatively, the reagent polynucleotide can be a primer for an amplification reaction in which the amount of product produced correlates with the formation of specific hybrids.

The specificity of the probe or primer, and the stringency of hybridization conditions are both chosen with a view to facilitating detection of sequences of interest, while diminishing false positive reactions. Thus, when it is important to distinguish between Tankyrase II sequences from Tankyrase I sequences, particularly when using sequence outside the GC domain, then stringency conditions should be high, and the reagent polynucleotide should be nearly identical to the sequence being tested for. Conditions can be determined empirically so that the reagent polynucleotide will hybridize with the Tankyrase II sequence being tested for but not with other sequences that might be present in the sample of interest. In other instances, assays for Tankyrase II are conducted on samples where Tankyrase I is not present, or where it is desirable to test for Tankyrase I and Tankyrase II together. In these instances, the capability of the probe to cross-hybridize with Tankyrase I is not a hindrance, and may provide certain advantages.

Polynucleotides of this invention can also be used to inhibit the transcription or translation of Tankyrase II in target cells. Such polynucleotides can be in the form of antisense constructs, which in some embodiments binds to Tankyrase II mRNA and prevent translation. Other polynucleotides of this invention are ribozymes having a substrate (Tankyrase II mRNA) binding portion, and an enzymatic portion with endonuclease activity that cleaves the substrate. Design and use of ribozymes is described generally in U.S. Pat. Nos. 4,987,071, 5,766,942, 5,998,193, and 6,025,167. The modulation of Tankyrase II expression using ribozyme constructs is embodied in this invention.

This invention also includes interfering RNA (RNAi) complexes. The structure and activity of RNAi is reviewed by Bosher et al. (Nature Cell Biol. 2:E31, 2000) and C. P. Hunter (Curr. Biol. 9:R440, 1999). The RNAi complexs of this invention comprise double-stranded RNA comprising Tankyrase II sense and antisense polynucleotides (optionally in a hairpin configuration) that specifically inhibits translation of mRNA encoding Tankyrase II and Tankyrase II-like proteins. Also contemplated are polynucleotides that bind to duplex Tankyrase II sequences to form a triple helix-containing nucleic acid, blocking expression at the transcription level (Gee et al., in Huber and Carr, 1994, Molecular and Immunologic Approaches, Futura Publishing Co.; Rininsland et al., 1997, Proc. Natl. Acad. Sci. USA 94:5854, 1997).

This invention also encompasses polynucleotides that encode polypeptides of interest. Characteristics of the polypeptides of this invention are described in the section that follows. For polypeptides that are fragments of naturally occurring Tankyrase II, there will be a corresponding naturally occurring polynucleotide encoding sequence. Those skilled in the art will recognize that because of redundancies in the amino acid code, any polynucleotide that encodes a peptide of interest can be used in a translation system to produce the peptide. Except where otherwise required, all possible codon combinations that translate into the peptide sequence of interest are included in the scope of the invention.

Polypeptides

The polypeptides of this invention include those that comprise amino acid sequences encoded within any of the polynucleotides of this invention, exemplified by SEQ. ID NO:6 and its subfragments. Also included in this invention are polypeptides containing Tankyrase II like sequence that is from naturally occurring allelic variants, synthetic variants, and homologs of Tankyrase II with a percentage of residues identical to the Tankyrase II protein, calculated as described elsewhere in this disclosure.

It is understood that substitutions, insertions, and deletions can be accommodated within a protein sequence without departing from the spirit of this invention. Conservative substitutions are typically more tolerable, such as the substitution of charged amino acids with amino acids having the same charge, or substituting aromatic or lipophylic amino acids with others having similar features. Certain peptides of this invention are 60%, 80%, 90%, 95%, or 100% identical to one of the sequences exemplified in this disclosure; in order of increasing preference. The length of the identical or homologous sequence compared with the prototype polypeptide can be about 7, 10, 15, 25, 50 or 100 residues in order of increasing preference, up to the length of the entire protein.

This invention includes polypeptides that are uniquely related to the prototype sequences, in comparison with other sequences that may be present in a sample or reaction mixture of interest. By way of example, peptides of at least about 10 consecutive amino acids that are at least 90% or 80% identical to a reference sequence, or wherein the rest of the peptide contains only conservative substitutions, may uniquely identify the peptide in terms of functional or antigenic characteristics. A peptide of at least about 25, 100, or 300 consecutive amino acids may be specific if at least 90%, 70%, 60%, or even 50% identical with the reference sequence. Longer peptides can be divided into halves (amino acids 1–584 and 585–1166 of SEQ. ID NO:6), or quarters (amino acids 1–292; 293–584; 585–876; 877–1166) and still retain one or more of their functional activities—such as ribosylation of target proteins, and the binding to conjugate peptides through the Tankyrase II ANK and SAM domains. Peptides from the region encoded by nucleotides 1–283 of SEQ. ID NO:5 are also of interest. It will be recognized that for some purposes such as reactions with antibody or the contact region on an opposing protein, a specific polypeptide sequence will readily accommodate deletions from the N- or C-end, say, of 3, 5, or even 10 amino acid residues.

Certain peptides of this invention are distinct from peptides previously known: These include human Tankyrase I proteins, and other proteins comprising PARP, SAM, and ANK domains. In certain embodiments, polypeptides of the invention are distinct from predicted amino acid sequences encoded in one or more previously known polynucleotide sequences, such as those cited at other places in this disclosure. A polypeptide of this invention can be "distinct" from other polypeptides because of an internal sequence difference (a substitution, deletion, or insertion), or because it is defined to encompass additional sequence at either end. Also included in the invention are artificially engineered fusion proteins in which a Tankyrase II like sequence is linked to a heterologous sequence which modulates Tankyrase II activity, provides a complementary function, acts as a tag for purposes of labeling or affinity purification, or has any other desirable purpose.

Preparation

Short polypeptides of this invention can be prepared by solid-phase chemical synthesis. The principles of solid phase chemical synthesis can be found in Dugas & Penney, Bioorganic Chemistry, Springer-Verlag NY pp 54–92 (1981), and U.S. Pat. No. 4,493,795. Automated solid-phase peptide synthesis can be performed using devices such as a PE-Applied Biosystems 430A peptide synthesizer (commercially available from Applied Biosystems, Foster City Calif.).

Longer polypeptides are conveniently obtained by translation in an in vitro translation system, or by expression in a suitable host cell. To produce an expression vector, a polynucleotide encoding the desired polypeptide is operably linked to control elements for transcription and translation, and then transfected into a suitable host cell. Expression may be effected in prokaryotes such as *E. coli,* eukaryotic microorganisms such as the yeast *Saccharomyces cerevisiae,* or higher eukaryotes, such as insect or mammalian cells. Control elements such as the promoter are chosen to permit translation at an acceptable rate under desired conditions. A number of expression systems suitable for producing the peptides of this invention are described in U.S. Pat. No. 5,552,524. Expression cloning is available from such commercial services as Lark Technologies, Houston Tex.

Following production, the protein is typically purified from the producing host cell by standard methods in protein chemistry in an appropriate combination, which may include ion exchange chromatography, affinity chromatography, and HPLC. Expression products are optionally produced with a sequence tag to facilitate affinity purification, which can subsequently be removed by proteolytic cleavage.

Also contemplated are Tankyrase II protein isolated from human biological samples, including tissue samples and cultured cell lines, tracking activity on the basis of functional assays and/or immunoassays provided below. Antibody to Tankyrase II described in the following section can be used in immunoaffinity or immunoprecipitation techniques to enrich Tankyrase II from biological samples. If desired, fragments can be made from whole Tankyrase II by chemical cleavage (e.g., using CNBr), or enzymatic cleavage (using trypsin, pepsin, dispase, V8 protease, or any other suitable endopeptidase or exopeptidase). Enrichment of peptides and proteins of this invention from natural or synthetic sources provides a purity of 10-fold, 100-fold, 1000-fold, or 10,000-fold higher than what is found in nature, in terms of a weight to weight ratio of Tankyrase II peptide to other proteins in the sample mass.

Assessment and use of the Polypeptides

Polypeptides of this invention can be used for a number of purposes, including but not limited to the characterization of telomerase function and how it is regulated, assays for proteins and nucleotide sequences to which Tankyrase II binds, the identification of new proteins with Tankyrase II binding activity that may play a role in maintaining telomere length, replicative capacity, apoptosis, chromosome packing, or gene expression, and the obtaining of antibody specific for Tankyrase II.

Subregions of Tankyrase II and homologs can be assessed for function based on the known domain structure of Tankyrase II, and employed according to the role they play in the activity of the whole molecule.

A putative PARP domain in a Tankyrase II homolog can be identified on the basis of sequence similarity, since a high degree of conservation with Tankyrase II PARP and other proteins with PARP domains (e.g., Tankyrase I, PARP-1 and PARP-2), especially over critical conserved residues, correlates with ribosylation activity. Residues of Tankyrase II thought to play an important role in the enzymatic activity are shown in Table 2. Functional assays for poly(ADP-ribose) polymerase can be conducted by incubating the putative PARP-containing peptide with a target protein (such as the Tankyrase II ANK and domains), or TRF1, in the presence of nicotinamide adenine dinucleotide ($NAD^+$), or an analog labeled with a radioisotope such as $^{32}P$ or $^{33}P$, biotin, or a fluorescent group. ADP-ribosylation can be monitored by incorporation of the label into the protein phase, by a change of size of the target protein (measurable, for example on a protein gel), or by detection of ADP ribose polymers on the target (for example, using commercially available antibody specific for ADP-ribose polymers, by digestion with glycohydrolases, or by physical-chemical mechanisms, such as mass spectrometry). Known PARP inhibitors like 3 amino-benzamide (3AB) can be used to verify the specificity of the assay. A number of other assays for rapid detection of poly(ADP-ribose) polymerase activity have been described. See Sallmann et al., Mol. Cell Biochem. 185:199, 1998; Simonin et al., Anal. Biochem. 195:226, 1991; Shah et al., Anal. Biochem 232:251, 1995. Peptides with confirmed PARP activity can then be used as a reagent to ADP-ribosylate protein targets of interest.

A putative SAM domain can also be identified on the basis of sequence similarity with the sterile alpha motif domain in other proteins (Tankyrase II, Tankyrase I, EphB2 receptor, and others reviewed by Stapleton et al., Nature Struct. Biol. 6:44, 1999). The SAM domain has been implicated in forming homodimers and heterodimers with other SAM-containing proteins (Stapleton et al., op. cit.; and Kyba et al., Dev. Genet. 22:74, 1998; Thanos et al., Science 283:833, 1999). Thus, putative SAM domains can be screened functionally in dimerization reactions: either with themselves, or with SAM domains from other proteins with known heterodimerization activity. Dimerization can be detected in an equilibrium system (e.g., using a biosensor), or in a separation system (e.g., by gel filtration chromatography or in a gel shift experiment). Dimerization can also be detected in a reporter gene assembly—for example, where a conjugate binding site on another protein is fused to a DNA-binding peptide, and the putative SAM domain is fused to a trans-activator. These constructs are then transfected into a cell comprising a reporter gene (such as Lac Z), which signals proximity of the trans-activator, indicating binding between the two peptides. Peptides with confirmed SAM activity according to any of these assays can then be used in turn as reagents in a dimerization assay to detect or quantitate Tankyrase II or other proteins with a SAM domain They can also be used to inhibit Tankyrase II activity by competition at the SAM binding site.

Putative ANK and GC domains can also be identified on the basis of sequence similarity to corresponding domains in Tankyrase II. In addition, ANK domains characteristically have a number of tandem repeats about 33 amino acids long. Dozens of proteins containing anywhere from one to dozens of ANK repeats are known. Michaely et al. (Trends Cell Biol. 2:127, 1992) report the consensus sequence as

```
-XGXTPLHLAARXGHVEVVKLLLDXGADVNAXTK-  SEQ ID NO:19
   A  I SQ NNLDIAEV  K    NPD  D
      V  K    T M R  Q    SI   N
                     E
```

ANK repeats generally are implicated in protein—protein binding, and the ANK domain in Tankyrase I is responsible for the binding of TRF1. Tankyrase II is believed to have binding activity for several proteins involved in telomere regulation and other aspects of chromosome management. Such proteins include TRF1, TRF2, TIN2, and Tankyrase I, which are all proteins known to interact in the management of telomeres. Peptide fragments and homologs of Tankyrase II can be tested for binding to such proteins, and those showing activity can in turn be used to assay TRF1, TRF2, TIN2, or Tankyrase I. The general format of such an assay comprises incubating a sample suspected of containing the protein with Tankyrase II binding activity with a peptide of this invention under conditions where the protein can bind the peptide to form a complex, and correlating any complex formed with the presence or amount of Tankyrase II binding activity in the sample. In a similar fashion, fragments and homologs of Tankyrase II can be tested for binding to polynucleotides having particular sequences, such as the tandem repeats that are characteristic of telomeres. Since Tankyrase II binds and ribosylates telomere-associated proteins, fragments and homologs of Tankyrase II can also be tested for modulation of telomere length. Cells are transfected with an expression vector for the fragment or homolog, and the effect on telomere length is measured by a suitable method, such as the assays described in U.S. Pat. Nos. 5,707,795, 5,741,677, and 5,834,193.

A systematic approach can be used to determine functional regions and homologs of Tankyrase II according to any of these assays. For example, the viability of an assay system is confirmed on the intact Tankyrase II protein; then a series of nested fragments is tested to determine the minimum fragment that provides the same activity. Similarly, amino acid substitutions can be introduced into the sequence until the activity is ablated, thereby determining what residues are critical for functional activity.

Peptides of this invention can also be used for the preparation and testing of antibodies against Tankyrase II, for the testing of other compounds for Tankyrase II binding activity, and for the screening of potential Tankyrase II modulators. These procedures are detailed further on in this disclosure.

Dominant Negative Mutants

Based on the sequence data provided in this disclosure, someone skilled in the art will be able to develop dominant negative polypeptide mutants of Tankyrase II, and polynucleotides that encode them. These mutants may be used to inhibit the function of Tankyrase II in a cell or reaction mixture. The production of dominant negative mutants entails deleting or mutating an important functional element of the native Tankyrase II. For example, functional mutation or deletion of the ANK domain may produce peptides that do not bind to TRF1 or TRF2, but retain SAM binding activity. Conversely, a functional mutation or deletion of the SAM domain may produce peptides are deficient in binding to proteins such as TRF1 or TRF2, but still have the ribosylation activity of PARP. A functional mutation or deletion of the PARP domain (for example, mutation of all or a subset of the residues from the Tankyrase II C-terminus to alanine), may result in a peptide that binds Tankyrase II associated proteins, but does not have any ribosylation activity.

Muteins with point mutations can also be obtained. Specifically, amino acids thought to be critical for the activity of the domain could be changed to a neutral amino acid such as alanine, and then reassayed for functional activity. For Tankyrase II, mutations that may abolish ribosylation activity are changes to His (position 1031), Gly (1032), Gly (1058), Tyr (1060), Tyr (1071), and Glu (1138).

TABLE 2

Critical Residues for PARP Activity in Tankyrase II

ERYTHRRKEV SEENHNHANE RMLF<u>HG</u>SPFV NAIIHKGFDE RHAYIGGMFG  SEQ. ID NO:20

A<u>GIY</u>FAENSS KSNQ<u>Y</u>VYGIG GGTGCPVHKD RSCYICHRQL LFCRVTLGKS

FLQFSAMKMA HSPPGHHSVT GRPSVNGLAL A<u>E</u>YVIYRGEQ AYPEYLITYQ

IMRPEGMVDG

Screening for Other Tankyrase II Binding Proteins

Those skilled in the art will readily appreciate that the assays described earlier in this section can be adapted to screen for other proteins that may be involved in telomere regulation, cell proliferative capacity, senescence, and apoptosis. The Tankyrase II domains ANK and SAM have characteristic features of protein binding molecules, and can be used to identify binding partners for Tankyrase II by incubating with a candidate compound under conditions suitable for binding, typically a physiological isotonic buffer containing any necessary cofactors that may promote transmolecular interaction. The formation of binding complexes with a candidate binding partner that is demonstrably specific (by virtue of being higher affinity than the binding of other candidate compounds) correlates with binding activity for Tankyrase II. Positive controls include peptides or proteins which have binding activity for Tankyrase II, while negative controls include ubiquitous and generally unreactive compounds, such as albumin. Candidates likely to screen positive for Tankyrase II binding include fragments and homologs related to telomere-associated proteins such as TRF1.

This type of conjugate binding assay can be conducted in several different formats. For example, Tankyrase II containing protein complexes can be isolated from human tissues or cell lines, for example, by tracking Tankyrase II through standard protein purification regimens by way of ribosylation activity or Tankyrase II antibody binding. In a similar approach, natural sources of Tankyrase II are solubilized in a suitable buffer, and Tankyrase II complexes are immunoprecipitated. The conjugate binding partner is then recovered from the complex, and characterized by physical and chemical criteria (such as apparent molecular weight determined by SDS gel electrophoresis), amino acid sequencing, or binding assays with Tankyrase II domains. In another example, Tankyrase II is labeled with a traceable substituent, such as biotin, a fluorescent group, an enzyme, a radioisotope, or a peptide group (e.g., FLG, HA, myc, or an immunoreactive peptide sequence), and then combined in a reaction solution with an isolated candidate binding partner, or with a mixture of components (such as a cell extract) in which compounds with Tankyrase II binding activity may be found. Formation of complexes with the labeled Tankyrase II is then detected (for example, by gel shift techniques or immunoprecipitation), and correlated with binding activity for Tankyrase II.

Another format is a coexpression system, using Tankyrase II, a Tankyrase II fragment, or a Tankyrase II homolog as bait. For example, a yeast two-hybrid screen system is employed, in which a Tankyrase II encoding sequence is fused to one part of the expression system, and a library of candidate binding partners is fused to the complementary component needed for expression of the marker. Cloned cells that express the activity of the marker contain an insert that comprises the encoding sequence for a Tankyrase II binding partner. Yeast two-hybrid screen systems are described generally in Bianchi et al., EMBO J., 16:1785, 1997. Reagents and suitable libraries (e.g., human fetal liver cDNA transformants) are commercially available from Clontech, Palo Alto Calif.

Antibodies

Antibody molecules of this invention include those that are specific for any novel peptide encompassed in this disclosure. These antibodies are useful for a number of purposes, including assaying for the expression of Tankyrase-II, and purification of Tankyrase-II peptides by affinity purification.

Polyclonal antibodies can be prepared by injecting a vertebrate with a polypeptide of this invention in an immunogenic form. If needed, immunogenicity of a polypeptide can be enhanced by linking to a carrier such as KLH, or combining with an adjuvant, such as Freund's adjuvant. Typically, a priming injection is followed by a booster injection is after about 4 weeks, and antiserum is harvested a week later. If desired, the specific antibody activity can be further purified by a combination of techniques, which may include Protein-A chromatography, ammonium sulfate precipitation, ion exchange chromatography, HPLC, and immunoaffinity chromatography using the immunizing polypeptide coupled to a solid support. Antibody fragments and other derivatives can be prepared by standard immunochemical methods, such as subjecting the antibody to cleavage with enzymes such as papain, pepsin, or trypsin.

Any unwanted cross-reactivity can be removed by treating the polyclonal antibody mixture with adsorbants made of those antigens attached to a solid phase, and collecting the unbound fraction. Contaminating activity against other proteins containing ANK, SAM, or PARP domains, or against Tankyrase I, or against Tankyrase-II from other species, can all be removed by adsorption if such cross-reactivity would interfere with the intended use of the antibody. Specificity of the original antisera can be improved to start with, by immunizing with peptide fragments of Tankyrase-II that are substantially distinct from the equivalent region of the homologous protein. Alternatively, antibodies that cross-react with Tankyrase I can be enriched by immunizing with peptide sequences that are shared between the two proteins. This is illustrated in Example 11.

Production of monoclonal antibodies is described in such standard references as Harrow & Lane (1988), U.S. Pat. Nos. 4,491,632, 4,472,500 and 4,444,887, and Methods in Enzymology 73B:3 (1981). Briefly, a mammal is immunized as described above, and antibody-producing cells (usually splenocytes) are harvested. Cells are immortalized, for example, by fusion with a non-producing myeloma, transfecting with Epstein Barr Virus, or transforming with oncogenic DNA. The treated cells are cloned and cultured, and the clones are selected that produce antibody of the desired specificity.

Other methods of obtaining specific antibody molecules (optimally in the form of single-chain variable regions) involve contacting a library of immunocompetent cells or viral particles with the target antigen, and growing out positively selected clones. Immunocompetent phage can be constructed to express immunoglobulin variable region segments on their surface. See Marks et al., New Eng. J. Med. 335:730, 1996, International Patent Applications WO 94/13804, WO 92/01047, WO 90/02809, and McGuiness et al., Nature Biotechnol. 14:1449,1996.

Antibodies can be raised that distinguish between Tankyrase II and Tankyrase I by selecting an immunogenic peptide from a region unshared by the ANK, SAM, or PARP domains of Tankyrase I, or other proteins having one of these domains. Suitable subregions of Tankyrase II are shown in Table 3.

TABLE 3

Immunogen Sequences for Tankyrase II Specific Antibody

| Amino Acid Sequence | Location | SEQ. ID NO: |
|---|---|---|
| MSGRRCAGGGAACASAAAEAVE | Beyond N-terminal of ANK domain (GC region) | 21 |
| TAAMPPSALPSCYKPQVLNGVRSPG ATADALSSGPSSPSSLSAASSLDNLS GSFSELSSVVSSSGTEGASSLEKKEV PGVDFSITQFVRN | Sequence between ANK and SAM domains | 22 |
| RPEGMVDG | Beyond C-terminal of PARP domain | 23 |

Antibody molecules in a polyclonal antiserum against intact Tankyrase II can be screened to map immunogenic portions of the amino acid sequence. Sequential peptides about 12 residues long are synthesized that cover the entire protein (SEQ. ID NO:6), and overlapping by about 8 residues. The peptides can be prepared on a nylon membrane support by standard F-Moc chemistry, using a SPOTS™ kit from Genosys according to manufacturer's directions. Prepared membranes are overlaid with the antiserum, washed, and overlaid with β-galactosidase conjugated anti-immunoglobulin. Positive staining identifies antigenic regions, which, in an appropriate context, may themselves be immunogenic. There will also be antibodies that span different parts of the primary structure, or which rely on a conformational component not displayed in smaller peptides.

The antibodies of this invention can be used in immunoassays to detect or quantitate any of the polypeptides of this invention, including the natural form of Tankyrase II present in biological fluid or tissue samples. For example, it may be desirable to measure Tankyrase II in a clinical sample to determine whether the level of Tankyrase II expression is abnormal, and then correlating the finding with the presence or status of a disease associated with increased or decreased Tankyrase II activity or abundance.

General techniques of immunoassay can be found in "The Immunoassay Handbook", Stockton Press NY, 1994; and "Methods of Immunological Analysis", Weinheim: VCH Verlags gesellschaft mbH, 1993). The antibody is combined with a test sample under conditions where the antibody will bind specifically to any modulator that might be present, but not any other proteins liable to be in the sample. The complex formed can be measured in situ (U.S. Pat. Nos. 4,208,479 and 4,708,929), or by physically separating it from unreacted reagents (U.S. Pat. No. 3,646,346). Separation assays typically involve labeled Tankyrase-II reagent (competition assay), or labeled antibody (sandwich assay) to facilitate detection and quantitation of the complex. Assays of this nature can also be used in a competitive format to identify antibodies that bind to the same epitope on a target compound. In one such format, the reference antibody is labeled, and tested for binding to Tankyrase II in competition with a test antibody. Antibodies can also be screened to identify those with inhibitory capacity for the binding and catalytic activities of Tankyrase II.

Modulating Tankyrase II Activity

This invention provides a number of different approaches to modulate Tankyrase II activity in a live cell. In one embodiment, the cell is genetically altered using a polynucleotide that affects expression of Tankyrase II at the transcription or translation level. Suitable polynucleotides include antisense sequences, ribozymes, or polynucleotides that form triplexes with the chromosomal gene for Tankyrase II, all of which were described in more detail earlier in this disclosure. In another embodiment, activity of Tankyrase II within the cell is inhibited by a peptide inside the cell that prevents Tankyrase II from exercising its usual function. Suitable peptides include intracellular antibody constructs that bind to regions of Tankyrase II necessary for catalytic or molecular binding activity, and dominant negative homologs that compete for the binding between Tankyrase II and a Tankyrase II binding partner. Proteins of this nature can be introduced into a cell by contacting the cell with a polynucleotide expression vector for the intracellular antibody or the mutant homolog.

Also contemplated are small molecule drugs that have the capability of modulating either Tankyrase II catalytic activity, or with its binding to conjugate partners. The ability to inhibit association between Tankyrase II and accessory proteins can be determined by introducing candidate inhibitors into any of the peptide binding assays described earlier, and correlating a decrease in protein complex formation with inhibitory capacity of the candidate.

Compounds can be screened for an ability to modulate ribosylation by preparing a reaction mixture comprising the test compound, either Tankyrase II or the Tankyrase II PARP domain (or a functional equivalent), the $NAD^+$ substrate, and a ribosylation target (Tankyrase II itself, or a Tankyrase II associated protein). Ribosylation is monitored by incorporation of $^{32}P$ or $^{33}P$ from labeled $NAD^+$ substrate into the solid phase, by a change of size of the target protein, or by any of the other techniques described earlier. An increase in ribosylation of the target correlates with an ability of the compound to enhance Tankyrase II ribosylation activity, while a decrease in ribosylation of the target correlates with inhibitory capacity of the test compound. The compound can also be screened in one or more parallel assays to determine whether it has the capacity to modulate the ribosylation activity of other enzymes—such as Tankyrase I, and other proteins containing PARP domains (reviewed recently by Still et al., Genomics 62:533, 1999).

Compounds that modulate the activity of Tankyrase II but not other ribosylation enzymes can be selected when it is desirable to obtain compounds that are specific for Tankyrase II. These assays can be used to screen random combinatorial libraries of small molecule compounds, or as part of rational drug design, based on known PARP inhibitors such as 3-amino-benzamide. Other potential Tankyrase II inhibitors include 4-amino-1,8-naphthalimide (Schlicker et al., Int. J. Radiat. Biol. 75:91, 1999), thiophenecaroxamides (Shinkwin et al., Bioorg. Med. Chem. 7:297, 1999), and 2-nitroimidazol-5-ylmethyl (Bioorg. Med. Chem. Lett. 9:2031, 1999).

It is potentially beneficial to modulate Tankyrase II activity in conditions associated with overexpression or underexpression of Tankyrase II. Peptides, expression systems, and small molecule drugs can also be screened according to the effect on cell biology. Cells expressing Tankyrase II treated with the test system can thereafter be monitored for an effect on telomere length as described earlier, or on replicative capacity in proliferation culture.

The following examples are provided as further non-limiting illustrations of particular embodiments of the invention.

EXAMPLES

Example 1

Identification of Expressed Sequence Tags for Tankyrase II

A BLAST search against the GenBank dbEST database using the Tankyrase I sequence identified several expressed sequence tags (ESTs). Many of the ESTs were identical in DNA sequence to the Tankyrase I gene. However, several ESTs coded peptides distinct from Tankyrase I. Further evaluation of these ESTs revealed they represented a distinct gene, termed Tankyrase II, since the DNA sequence identity to Tankyrase I was significantly lower than the amino acid identity, with a preponderance of silent third position codon changes.

The ESTs R64714, AA244138, and AA244137 contain sequences of the ankyrin domain of Tankyrase II; the EST AA307492 contain sequences of the SAM domain; ESTs H11865, H17748, N57467, R06946, AI247608, and R06902 contain sequences of the PARP domain. Additional 5' sequence of the 3' EST AI247608 clone revealed it diverges from the tankyrase gene and does not overlap with the SAM domain. It may contain an unprocessed intron. The 3' ESTs H11505, H17635, and N29528 were identified in GenBank as partners for the 5' ESTs H11865, H17748, and N57467, respectively. These 9 ESTs along with additional sequence obtained from the H11865, H17748, N57467, R06946 clones formed a contig containing the PARP domain and ~1 kbp of the 3' UTR, including a poly-A tail. These ESTs formed 3 contigs that contained 3 of the Tankyrase II domains and approximately 40% of the coding region.

Additionally, AA088990 and AI426537 are ESTs containing the ankyrin and PARP domains of a putative mouse Tankyrase II, respectively.

Example 2

Cloning of the N-Terminus of Tankyrase II

To extend the ANK EST contig, Rapid Amplification of cDNA Ends (RACE™) (Gibco-BRL, #18374-058) was performed using the primers tankII-2 and tankII-3 and (i) poly A+RNA from BJ fibroblasts transduced with a a retroviral vector expressing the human TERT gene (pBABE-TERT) and (ii) the Marathon-Ready testis cDNA (Clontech, #7414-1). This was followed by nested amplification using primers LtankII-1 and LtankII-2, respectively.

The products from these amplifications were cloned into pCR2.1-TOPO (InVitrogen, #45-0641). Four clones were identified by PCR with primers (AAP [Gibco] or AP-1 [Clonetech]) to the vector and the ANK EST contig (LtankII-1 or LtankII-2), termed inside-out PCR, to contain additional DNA 5' to the EST contig. Custom primers were designed based on the evolving sequence data. Subsequent sequence analysis indicated that only two, designated MP9 and MP12, contained authentic Tankyrase II sequences. "Inside-out" PCR is the term used to describe amplification using a primer pair in which one primer is from the target gene (e.g., Tankyrase II) and the second primer is specific for the vector.

Additional N-terminally extended clones were isolated by the GeneTrapper (Gibco-BRL, #10356-020) cDNA clone enrichment procedure using the oligonucleotides LtankII-4B, LtankII-5B, and LtankII-6B and plasmid cDNA libraries from liver and spleen (Gibco-BRL, #10422-012 and 10425-015, respectively). Approximately 100 GeneTrapper clones were screened by colony hybridization with a PCR probe (described infra) from the ANK clone AA244138 and by inside-out PCR (primers: SP6/tankII-2 and SP6/tankII-3) to identify four clones (S10, S25, S34, and L11) that contained additional DNA 5' to the EST contig.

Sequence analysis of the 2 RACE and 4 GeneTrapper clones formed a contig that extended approximately 200 bp downstream and approximately 1100 bp upstream of the original ANK EST contig. The 5' most sequence terminated in DNA homologous to the most N-terminal tankyrase ANK repeat just after the HPS domain.

Example 3

Identification of λ Bacteriophace Clones of Tankyrase II

Three λ bacteriophage human cDNA libraries, λgt10 thymus (Clontech, HL1074a), λgt11 293 human embryonic kidney cancer cell line, and λTriplx Testis (Clontech, cat # HL5033t), were screened by plaque hybridization with a probe from the ANK clone AA244138. The probe was generated by PCR using the primers UtankII-5 and LtankII-7. Twenty-six phage were positively identified through secondary and tertiary plaque hybridizations. Using PCR the presence of the ANK EST contig was confirmed in all 26 phage. Additional PCR was used to identify one phage (λ11L-1-1) from the 293 library that contained the most N-terminal ankyrin repeat and the ANK, SAM, and PARP contigs. The λ11L-1-1 insert is believed to contain the entire Tankyrase II coding sequence. Two other phage λ11-L-1-3, λ11L-1-4 (293) from the 293 library were identified that contained the most N-terminal ankyrin repeats and the original ANK contig. Inside-out PCR (primers gt10-5'/LtankII-31 or gt11-5'/LtankII-31), showed these clones contained up to 800 bp of additional Tankyrase II sequence upstream of the most N-terminal ankyrin repeat. These vector/N-terminal insert PCR products and PCR products from these four phage that linked the SAM and ANK contigs and the SAM and PARP contigs were sequenced directly.

The λ11L-1-1, λ11L-1-3, or λ11L-1-4 can be individually characterized by the following tests. Page λ11L-1-1 contains DNA that can be amplified with the primer pairs UtankII-5/LtankII-16, UtankII-5/LtankII-9, and UtankII-3/LtankII-10 (Table 4). Phage λ11L-1-3 contains DNA that can be amplified with the primer pair UtankII-5/LtankII-16, but not with the primer pairs UtankII-5/LtankII-9 and UtankII-3/LtankII-10 (Table 4). Phage λ11L-1-4 contain DNA that can be amplified with the primer pairs UtankII-5/LtankII-16, UtankII-5/LtankII-9, but not with the primer pair UtankII-3/LtankII-10 (Table 4). Additional sequence was obtained by amplifying phage λ11L-1-4 DNA using UTankII-3 and LTankII-11 primers (PARP/SAM spanning sequence).

Example 4

Tankyrase II Amino-Terminal Domain Sequence

More than 200 GeneTrapper clones obtained using UTankII-4B, UTankII-5B and UTankII-6B oligonucleotides were probed by colony hybridization with a $^{32}$P-labeled PCR fragment from clone MP9 (supra) using primers UTank2-30 and LTank2-1. Of the positive clones identified, sequence was obtained from 5 independent clones from two different cDNA libraries (SuperScript human liver cDNA and SuperScript human spleen cDNA libraries [Clonetech]). The clones are: S4.66, S4.21, S6.7, S6.91, L5.4. Of these L5.4 had longest 5' sequence. L5.4 was deposited with the ATCC (American Type Culture Collection, 10801 University Boulevard, Manassas, Va.) and assigned Accession No. 203919. The DNA encoding the amino-terminal region of the Tankyrase II polypeptide is extremely GC-rich (>80% in the sequence).

FIGS. 2 and 3 show cDNA and protein sequence data obtained for Tankyrase II.

TABLE 4

Primers for amplifying Tankyrase II sequences

| Forward & Reverse Primer Designation | Nucleotide Sequence | SEQ. ID NO: |
|---|---|---|
| UTANKII-1 | GTT ACA TTT GCC ACA GGC AG | 24 |
| UTANKII-2 | GTC TTT CTT GCA GTT CAG TG | 25 |
| UTANKII-3 | GAG TCG AGA GAC TTA TCT CC | 26 |
| UTANKII-4A | GAG CAC AGA GAT GGA GGT C | 27 |
| UTANKII-4B | ATG TAC AGC AAC TCC TCC AAG A | 28 |

TABLE 4-continued

Primers for amplifying Tankyrase II sequences

| Forward & Reverse Primer Designation | Nucleotide Sequence | SEQ. ID NO: |
|---|---|---|
| UTANKII-5A | CAG ACA ATT GCT GGA AGC TG | 29 |
| UTANKII-5B | CAG ACA ATT GCT GGA AGC TGC A | 30 |
| UTANKII-6A | CTA CTC CTG AGC TAT GGG TG | 31 |
| UTANKII-6B | GTG TAC TGT TCA GAG TGT CAA C | 32 |
| LTANKII-7 | CCA TGC TGG AGC AGA AGT TTG | 33 |
| LTANKII-8 | GCT AAA ATC TCT CCT GGA ACC | 34 |
| LTANKII-9 | GTT TGT GCC TAT GTC CAT AAG C | 35 |
| LTANKII-10 | CAA AAG AGC AGC TGC CTG TG | 36 |
| LTANKII-11 | CTG CAG GAA AGA CTT TCC CAA G | 37 |
| UTANKII-12 | GCA GCC AGT GGC CCT CTA CG | 38 |
| UTANKII-13 | GCC CCA CAG GCC TGT GGC C | 39 |
| UTANKII-14 | GAA ACT AAT TCC CAC TAA CC | 40 |
| LTANKII-15 | AAT AAA TAC TGG GCT AGT AC | 41 |
| LTANKII-16 | AGG GTC TGC ACC ATG CTG GAG C | 42 |
| LTANKII-17 | ATA AAT CAG CTA CAT TAA CTA C | 43 |
| LTANKII-18 | CCC AGC TGC AAA ATG AAG T | 44 |
| LTANKII-19 | AAT GAC TCT GCA GTT GAC AC | 45 |
| UTANKII-20 | GAT ACA CTC ACC GGA GAA AAG | 46 |
| LTANKII-21 | GTG AAC TGG ACA CCC AGT ACC | 47 |
| UTANKII-22 | GGT ATG GTC GAT GGA TAA ATA G | 48 |
| LTANKII-23 | GAA CAC AGT ATT GTA TTA G | 49 |
| UTANK2-30 | CGG CGG GCA GGA AAT CCA CC | 50 |
| LTANK2-31 | TTG GGG TCT GCA CCA TGT CG | 51 |
| UTANK2-32 | TCC AGA GGC TGG TGA CCC CTG A | 52 |
| LTANKII-33 | TCT GCT AAA TCC AAT GCT GTC C | 53 |
| LTANKII-34 | TGC AGC GGG GTG GAT TTC CT | 54 |
| LTANKII-35 | CAT TTT GAA GCA AAT ATT TA | 55 |
| LTANKII-36 | GGA ATA AGG CCC CCA TTA TA | 56 |
| LTANKII-35 | CAT TTT GAA GCA AAT ATT TA | 57 |
| LTANKII-36 | GGA ATA AGG CCC CCA TTA TA | 58 |

Example 5

Northern Hybridization of Tankyrase II mRNA

A Northern blot (Human Multiple Tissue Northern (MTN) TM Blot™ (obtained from Clontech, Cat #7780-1) was hybridized with a 3'UTR probe at $2\times10^6$ cpm/ml hybridization solution. The 3' UTR fragment was amplified by PCR with UTank2-14 and LTank2-15 primers using the Est clone n57467 as a template.

The Northern analysis showed that the Tankyrase II transcript is about 6 to 7.5 kb in length, and is expressed in most tissues, including brain, heart, colon, thymus, spleen, kidney, liver, small intestine, lung, and peripheral blood leukocytes. It appears to be particularly abundant in skeletal muscle and placenta. "BJ RNA" is polyadenylated RNA isolated from a human fibroblast cell line designated BJ.

Example 6

Plasmid Clones of the Tankyrase II cDNA

The isolated Tankyrase II cDNA bacteriophage clones were transferred to plasmid vectors as follows:

1. The Tankyrase II cDNA contained in bacteriophage λ11L-1 was removed as a BsiW1 fragment and inserted into the Acc65 I site of pBluescript II SK+ (Stratagene) (designated pGRN509).
2. The Tankyrase II cDNA contained in bacteriophage λ11L-3 was removed as a BsiW1 fragment and inserted into the Acc65 I site of pBluescript II SK+ (Stratagene) (pGRN510).
3. The Tankyrase II cDNA contained in bacteriophage λ11L-4 was removed as a BsiW1 fragment and inserted into the Acc65 I site of pBluescript II SK+ (Stratagene) (pGRN511).

The PARP domain from pGRN509 was amplified with the primer hParp1 (5'-CC ATCGAT GCCAGCCATG GAG GTT CCA GGA GTA GAT-3'; SEQ. ID NO:59) and primer hParp2 (5'-GCTCT AGA TCA GGC CTC ATA ATC TGG-3'; SEQ. ID NO:60) using PFU/Taq polymerase mixture. The resulting fragment was TA cloned into the InVitrogen TA cloning vector pCR2.1-TOPO®. A clone (pGRN513) was selected with the sense strand downstream of the T7 promoter. The primer hparp1 introduces an ATG and kozak consensus sequence at the 5' end of the PARP To assemble a full length cDNA containing the Tankyrase II ORF fragments from pGRN511 and pGRN509 were combined as follows: The Not I fragment of pGRN511 was inserted into the Not I site of pBluescript II KS+ (Stratagene) (pGRN512). pGRN512 was digested with Nhe I and Cla I and the larger vector/Tankyrase II cDNA fragment was isolated, the ~2.1 Kbp Nhe I-Cla I fragment of pGRN509 was ligated to this fragment to generate a clone containing the full length Tankyrase II cDNA ORF (pGRN514).

Example 7

Further Sequence Data for the Tankyrase II cDNA

The plasmids pGRN509 and pGRN511 were sequenced with an ABI 377 automated DNA sequencer by standard techniques using primers complementary to the insert sequences.

FIG. 4 shows the revised cDNA sequence (SEQ. ID NO:5), and the revised amino acid translation (SEQ. ID NO:6). The translated protein product is presumed to begin at the Met encoded at position 224 of the cDNA sequence, and ending at position 3721. The Met is assigned position No. 1 for purposes of numbering the amino acid translation. However, the upstream polynucleotide sequence shown contains no stop codon, and the translation starting Met may be further upstream from the insert shown in the figure.

The number of amino acids in Tankyrase II corresponding to nucleotides 284 to 3721 is 1166 amino acids long. The calculated molecular weight is 126.8 kDa, and the calculated isoelectric point is 6.78.

FIG. 1 shows the location of the functional domains in the Tankyrase II sequence. The position of each domain within the sequence is shown in Table 5.

TABLE 5

Location of Functional Domains in Tankyrase II

| Domain | Position |
|---|---|
| GC | 1 to 22 |
| ANK | 23 to 859 |
| SAM | 870 to 935 |
| PARP | 1023 to 1161 |

FIG. 5 and FIG. 6 compare Tankyrase II (SEQ. ID NO:6) with its closest known intraspecies homolog, Tankyrase I (SEQ. ID NOs:8), at the protein level, and at the cDNA level.

The degree of sequence identity of Tankyrase II relative Tankyrase I was determined in this example by dividing the two proteins into their functional domains. Identity was then calculated by dividing the number of matched residues by the number of matched and mismatched residues over each area, scoring half a point for each unmatched residue occurring in a gap or overhang on either side. Results were as follows:

N-terminus: 7 matches/7 matches+20 mismatches+(79 gaps/2)=7%

Ankyrin repeats: 720/720+104+(7/2)=87%

Inter domain 1: 7/7+6+(2/2)=50%

SAM domain: 54/54+12=82%

Inter domain #2: 82/82+15=83%

PARP domain: 132/132+7=95%

C-terminus: 0/5+(8/2)=0%

Overall: 992/1241.5=79.9%

Overall (discounting N- and C-termini): 985/1133.5=86.9%

Example 8

Testing for PARP Activity

To produce a Tankyrase II peptide comprising the PARP domain, pGRN513 was transcribed and translated in a 20 fold scale up in vitro coupled transcription/translation (TnT) reaction. Full-length Tankyrase II peptides can be obtained by similar procedures, using plasmids designated pGRN514 or pGRN323.

Each plasmid was set up as follows, paired with a reaction in which the plasmid DNA was omitted as an unprogrammed control. The reaction mixture contained 20 μg of circular plasmid pGRN513 or pGRN514 or pGRN523; 500 μl rabbit reticulocyte lysate; 1×TnT Buffer; 20 μl T7 RNA polymerase; 20 μl 1 mM complete amino acids; 20 μl RNAguard™; and $dH_2O$ to 1 ml total volume. The reactions were incubated for 90 minutes at 30° C., then pooled and made 50% with ammonium sulfate. The resulting pellets were washed with 50% ammonium sulfate and resuspended in either 400 μl PARP buffer A (50 mM Tris-HCL pH 8, 4 mM $MgCl_2$, 0.2 mM DTT, 50 mM NaCl, 10 mM β-mercaptoethanol, 1 mM PMSF) for the Tankyrase II reactions, or in 100 μl PARP buffer A for the unprogrammed control. The TnT resuspended lysate was then dialysed overnight against two changes of PARP buffer A to remove traces of ammonium sulfate.

The following assays were performed to determine PARP activity:

1. $^{35}S$-labelled Tankyrase without $NAD^+$
2. ~150 ng Tankyrase II PARP domain, with $NAD^+$
3. ~150 ng Tankyrase II PARP domain, with $NAD^+$, 1.5 μg TRF1, 5 μg Histones
4. ~150 ng Tankyrase II PARP domain, with $NAD^+$, 1.5 μg TRF1, 5 μg Histones
5. ~150 ng Tankyrase II PARP domain, with $NAD^+$, 1.5 μg TRF1, 5 μg Histones and 1.6 mM 3-aminobenzamide
6. Unprogrammed lysate with NAD, 1.5 μg TRF1, 5 μg Histones
7. PARP control enzyme (Trevigen cat#4667-50-01), with $NAD^+$, TRF1, Histones For Reaction 1, Tankyrase II was biosynthetically labeled using [$^{35}S$]methionine as a molecular weight marker of the non-ribosylated form. The reaction mixture comprised 1 μg of circular plasmid pGRN513 or pGRN514 or pGRN523; 25 μl rabbit reticulocyte lysate; 1×TnT Buffer; 1 μl T7 RNA polymerase; 1 μl 1 mM methionine; 2 μl [$^{35}S$] Met (1000 Ci/mmol); 1 μl RNAguard™; and dH20 to 50 μl total volume. The product was precicipitated with 50% ammonium sulfate but not dialysed.

Reactions 2 to 6 were conducted under the following assay conditions: 1×PARP enzyme buffer (Trevigen Cat#4667-50-02), 40 μM [$^{32}P$]$NAD^+$ (50 μCi). Reactions 2, 3 5–7 with TCA were precipitated in 20% TCA, pellets were washed sequentially with 5% TCA, 90% acetone/1 N HCl and 100% acetone. Pellets were then resuspended in 40 μL protein loading buffer and heated for 10 minutes at 80° C.

Reaction 4 was immunoprecipitated with 10 μL Anti-poly (ADP-ribose) monoclonal antibody (Trevigen Cat#4335-MC-100) and 10 μL Anti-poly (ADP-ribose) polyclonal antibody (Biomol Cat# SA-276). Reaction v was incubated on ice for 30 minutes in the presence of the antibodies. 40 μL Protein A slurry was incubated by rotating at room temperature for 2 hours. Beads were washed twice with PARP buffer A containing 50 mM NaCl, and once in PARP buffer A containing 450 mM NaCl. Beads were boiled in 40 μL protein loading buffer. Reaction 7 was performed according to manufacturer's directions (Trevigen). Samples from these reaction mixtures were then analysed on a 12% SDS-PAGE gel. The gel was dried and exposed to a phosphorimager screen and imaged. Preliminary results of these assays have been inconclusive.

Example 9

Chromosomal Location of the Tankyrase II Gene

The Tankyrase II gene was localized to chromosome 10q by radiation hybrid mapping (Boehnke et al., Am J. Hum Genet 49:1174, 1991; Walter et al., Nature Genet 7:22) using the medium resolution Stanford G3 panel of 83 RH clones of the whole genome (created at the Stanford Human Genome Center). A human lymphoblastoid cell line (donor; rM) was exposed to 10,000 rad of X-rays and was then fused with non-irradiated hamster recipient cells (A3). Eighty-three independent somatic cell hybrid clones were isolated, and each represents a fusion event between an irradiated donor cell and a recipient hamster cell. The panel of G3 DNA was used for ordering markers in the region of interest as well as establishing the distance between these markers.

The primers used for RH mapping were UTANKII-20 and LTANKII-21 (Table 4). The 83 pools were amplified independently and 13 (16%) scored positive for Tankyrase II. The amplification results were submitted to the Stanford RH server, which then provided the map location, 10q23.3, and the closest marker, STS D10S536.

Example 10

Transcription and Translation of Tankyrase II PARP Domain pGRN513 was tested by in vitro transcription/translation (TnT) to confirm it encoded the appropriate sized protein. The PARP domain is expected to run at approximately 35 kDa, as determined by SDS polyacrylamide gel electrophoresis. TnT reactions were set up for pGRN513 and pGRN125 (hTERT as a positive control for the TnT reaction) with the following components:

1 μg of circular plasmid

25 μl rabbit reticulocyte lysate

1×TNT Buffer (Promega Cat # L4610)

1 μl T7 RNA polymerase

1 μl 1 mM methionine

2 μl [$^{35}S$] methionine (1000 Ci/mmol) (Amersham Cat #SJ 1015, 1000 Ci/mmol)

1 μl RNAguard (Pharmacia Cat #27-0815-01)

dH20 to 50 μl total volume

The reaction was incubated for 90 minutes at 30° C. 40 μl of the TnT reactions were precipitated with 50% ammonium sulfate and resuspended in 40 μl of buffer (20 mM HEPES-KOH pH 7.9, 2 mM $MgCl_2$, 1 mM EGTA, 10% glycerol, 0.1% Nonidet P-40, 0.1 mM phenylmethylsulphonyl fluoride)/100 mM NaCl. 5 μL of TnT reaction, 5 μl of ammonium sulfate cut TnT reaction and 5 μL of the ammonium sulfate cut was analyzed on a 12% SDS-PAGE. pGRN513 generated the expected size fragment.

Example 11

Antibodies to Tankyrase II

Peptides are prepared on a synthesizer for use as immunogens based on the sequence data shown in

TABLE 6

Peptide Immunogens

| Laboratory Designation | Sequence | Specificity | SEQ. ID NO: |
|---|---|---|---|
| GCJT-1 | MAASRRSQC | residues 1–8 of Tankyrase I | 61 |
| GCJT-2 | MSGRRCAGK | residues 1–8 of Tankyrase II | 62 |
| GCJT-3 | QEGISLGNSEADRQC | residues 481–494 of Tankyrase II | 63 |
| QCJT-4 | GEYKKDELLEC | residues 269–276 of Tankyrase II; common to both proteins | 64 |

Underlined residues do not belong to the native sequence of the proteins but are added to the peptides in order to couple them to carriers for antibody production.

Biological Deposit

Phage λ11L-1-1, λ11L-1-3, λ11L-1-4 were deposited as a mixture with the ATCC (American Type Culture Collection, 10801 University Boulevard, Manassas, Va.) on Apr. 12, 1999, under Accession No. 203919.

Phage are stored in a buffer of 5.8 g NaCl, 2 g $MgSO_4$.&$H_2O$, 50 mL 1 M Tris-HCl pH 7.5, and 0.01% gelatin (Difco). To isolate each phage, test individual phage are separated by plaque purification by standard PCR amplification. Tankyrase II sequence in phage λ11L-1-1 can be amplified with the primer pairs UtankII-5/LtankII-16, UtankII-5/LtankII-9, and UtankII-3/LtankII-10 (Table 4, supra). Tankyrase II sequence in phage λ11L-3 can be amplified with the primer pair UtankII-5/LtankII-16, but not with the primer pairs UtankII-5/LtankII-9 and UtankII-3/LtankII-10. Tankyrase II sequence in phage λ11L-1-4 contains DNA that can be amplified with the primer pairs UtankII-5/LtankII-16, UtankII-5/LtankII-9, but not with the primer pair UtankII-3/LtankII-10.

TABLE 7

Sequences Listed in this Disclosure

| SEQ. ID NO: | Subject | Reference |
|---|---|---|
| 1 | Human Tankyrase II DNA sequence | FIG. 2, this Invention. (60/128,577) |
| 2 | Human Tankyrase II protein sequence | FIG. 2, this Invention. (60/128,577) |
| 3 | Human Tankyrase II DNA sequence | FIG. 3, this Invention. (60/129,123) |
| 4 | Human Tankyrase II protein sequence | FIG. 3, this Invention. (60/129,123) |
| 5 | Human Tankyrase II DNA sequence | FIG. 4, this Invention. |
| 6 | Human Tankyrase II protein sequence | FIG. 4, this Invention. |
| 7 | Human Tankyrase I DNA sequence | GenBank Accession No. AF082556 Smith et al. Science 282:1484 (1998) |
| 8 | Human Tankyrase I protein sequence | GenBank Accession No. AF082556 Smith et al. Science 282:1484 (1998) |
| 9 | Human cDNA clone similar to Ankyrin G119 mRNA | GenBank Accession No. AA244138 R. Strausberg (unpublished) |
| 10 | Human cDNA clone similar to Ankyrin-related ADP-ribose polymerase mRNA | GenBank Accession No. AW157349 L. Hillier et al. (unpublished) |

TABLE 8

Additional Sequence Data

| GenBank Accession No. | Subject | Reference |
|---|---|---|
| U40705 | TRF1 sequence | Chong et al., Science 270:1663 (1995) |
| AF002999 | TRF2 sequence | Broccoli et al., Nature Genet. 17:231 (1997) |
| AF195512 | TIN2 sequence | Kim et al., Nat. Genet. 23:405 (1999) |

For purposes of prosecution in the U.S.A., the DNA and encoded amino acid sequences listed in this are hereby incorporated herein by reference.

What is claimed as the invention is:

1. A method for ribosylating a target protein, comprising incubating the target protein with a peptide in the presence of $NAD^+$;

wherein the peptide has ribosylation activity, and is encoded by a polynucleotide that hybridizes under stringent conditions to a polynucleotide with the sequence in SEQ. ID NO:5, but not to a polynucleotide with the sequence in SEQ. ID NO:7.

2. A method of screening a test compound for an ability to affect Tankyrase II activity, comprising incubating a reaction mixture containing a peptide, a target protein, a substrate, and the test compound, under conditions where the target protein would be ribosylated by the peptide in the absence of the test compound; and determining any effect of the test compound on the amount or rate of ribosylation;

wherein the peptide has ribosylation activity, and is encoded by a polynucleotide that hybridizes under stringent conditions to a polynucleotide with the sequence in SEQ. ID NO:5, but not to a polynucleotide with the sequence in SEQ. ID NO:7.

3. The method of claim 2, wherein the substrate is nicotinamide adenine dinucleotide ($NAD^+$).

4. The method of claim 2, wherein the target protein is selected from TRF1, TRF2, TIN2, Tankyrase I, and Tankyrase II, and fragments thereof.

5. The method of claim 2, wherein the peptide is expressed by a recombinant host cell in the reaction mixture.

6. The method of claim 2, wherein the peptide is isolated from a host cell before being added to the reaction mixture.

7. The method of claim 2, further comprising determining whether the compound affects the activity of ribosylation enzymes other than Tankyrase II.

8. The method of claim 2, wherein the compound enhances the amount or rate of ribosylation.

9. The method of claim 2, wherein the compound inhibits the amount or rate of ribosylation.

10. A method of screening a test compound for an ability to affect Tankyrase II activity, comprising expressing a polynucleotide in a host cell, combining the cell with the test compound, and determining any effect of the test compound on the cell, in comparison with a cell expressing the polynucleotide in the absence of the compound;

wherein the polynucleotide hybridizes under stringent conditions to a polynucleotide with the sequence in SEQ. ID NO:5, but not to a polynucleotide with the sequence in SEQ. ID NO:7, and which encodes a peptide that has ribosylation activity.

11. A method for ribosylating a target protein, comprising incubating the target protein with a peptide in the presence of $NAD^+$;

wherein the peptide comprises an amino acid sequence that is at least 90% identical to a sequence contained in SEQ. ID NO:6, and that has ribosylation activity.

12. The method of claim 11, wherein the peptide comprises SEQ. ID NO:6 or fragment thereof that has ribosylation activity.

13. A method of screening a test compound for an ability to affect Tankyrase II activity, comprising incubating a reaction mixture containing a peptide, a target protein, a substrate, and the test compound, under conditions where the target protein would be ribosylated by the peptide in the absence of the test compound; and determining any effect of the test compound on the amount or rate of ribosylation;

wherein the peptide comprises an amino acid sequence that is at least 90% identical to a sequence contained in SEQ. ID NO:6, and that has ribosylation activity.

14. The method of claim 13, wherein the peptide comprises SEQ. ID NO:6 or fragment thereof that has ribosylation activity.

15. The method of claim 13, wherein the peptide comprises at least 10 consecutive amino acids contained in SEQ. ID NO:6.

16. The method of claim 13, wherein the peptide comprises at least 25 consecutive amino acids contained in SEQ. ID NO:6.

17. The method of claim 13, wherein the peptide comprises at least 100 consecutive amino acids contained in SEQ. ID NO:6.

18. The method of claim 13, wherein the substrate is nicotinamide adenine dinucleotide ($NAD^+$).

19. A method of screening a test compound for an ability to affect Tankyrase II activity, comprising expressing a polynucleotide in a host cell, combining the cell with the test compound, and determining any effect of the test compound on the cell, in comparison with a cell expressing the polynucleotide in the absence of the compound;

wherein the polynucleotide encodes a peptide comprising an amino acid sequence that is at least 90% identical to a sequence contained in SEQ. ID NO:6, and that has ribosylation activity.

20. The method of claim 19, wherein the peptide comprises SEQ. ID NO:6 or fragment thereof that has ribosylation activity.

21. A method of screening a test compound for an ability to affect Tankyrase II activity, comprising expressing a polynucleotide in a host cell, combining the cell with the test compound, and determining any effect of the test compound on the cell, in comparison with a cell expressing the polynucleotide in the absence of the compound;

wherein the polynucleotide encodes a peptide comprising an amino acid sequence that is at least 90% identical to a sequence contained in SEQ. ID NO:6, and that further comprises a PARP domain, a SAM domain, and an ANK domain.

22. The method of claim 21, wherein the peptide ribosylates a target protein in the presence of $NAD^+$.

* * * * *

SEQUENCE LISTING

```
<160> NUMBER OF SEQ ID NOS: 64

<210> SEQ ID NO 1
<211> LENGTH: 4493
<212> TYPE: DNA
<213> ORGANISM: Homo sapiens
<220> FEATURE:
<221> NAME/KEY: CDS
<222> LOCATION: (1)..(3999)
<223> OTHER INFORMATION:
<221> NAME/KEY: misc_feature
<222> LOCATION: (1)..(586)
<223> OTHER INFORMATION: Sequences not determined at this position .
      Unknown residue put in to provide alignment.
<221> NAME/KEY: misc_feature
<222> LOCATION: (596)..(597)
<223> OTHER INFORMATION: Sequences not determined at this position .
      Unknown residue put in to provide alignment.
<221> NAME/KEY: misc_feature
<222> LOCATION: (621)..(621)
<223> OTHER INFORMATION: Sequences not determined at this position .
      Unknown residue put in to provide alignment.
<221> NAME/KEY: misc_feature
<222> LOCATION: (626)..(626)
<223> OTHER INFORMATION: Sequences not determined at this position .
      Unknown residue put in to provide alignment.
<221> NAME/KEY: misc_feature
<222> LOCATION: (629)..(629)
<223> OTHER INFORMATION: Sequences not determined at this position .
```

-continued

```
      Unknown residue put in to provide alignment.
<221> NAME/KEY: misc_feature
<222> LOCATION: (638)..(638)
<223> OTHER INFORMATION: Sequences not determined at this position .
      Unknown residue put in to provide alignment.
<221> NAME/KEY: misc_feature
<222> LOCATION: (693)..(694)
<223> OTHER INFORMATION: Sequences not determined at this position .
      Unknown residue put in to provide alignment.
<221> NAME/KEY: misc_feature
<222> LOCATION: (724)..(724)
<223> OTHER INFORMATION: Sequences not determined at this position .
      Unknown residue put in to provide alignment.
<221> NAME/KEY: misc_feature
<222> LOCATION: (730)..(730)
<223> OTHER INFORMATION: Sequences not determined at this position .
      Unknown residue put in to provide alignment.
<221> NAME/KEY: misc_feature
<222> LOCATION: (764)..(764)
<223> OTHER INFORMATION: Sequences not determined at this position .
      Unknown residue put in to provide alignment.
<221> NAME/KEY: misc_feature
<222> LOCATION: (791)..(791)
<223> OTHER INFORMATION: Sequences not determined at this position .
      Unknown residue put in to provide alignment.
<221> NAME/KEY: misc_feature
<222> LOCATION: (2148)..(2148)
<223> OTHER INFORMATION: Sequences not determined at this position .
      Unknown residue put in to provide alignment.
<221> NAME/KEY: misc_feature
<222> LOCATION: (2177)..(2177)
<223> OTHER INFORMATION: Sequences not determined at this position .
      Unknown residue put in to provide alignment.
<221> NAME/KEY: misc_feature
<222> LOCATION: (2382)..(2382)
<223> OTHER INFORMATION: Sequences not determined at this position .
      Unknown residue put in to provide alignment.
<221> NAME/KEY: misc_feature
<222> LOCATION: (2398)..(2398)
<223> OTHER INFORMATION: Sequences not determined at this position .
      Unknown residue put in to provide alignment.
<221> NAME/KEY: misc_feature
<222> LOCATION: (2466)..(2466)
<223> OTHER INFORMATION: Sequences not determined at this position .
      Unknown residue put in to provide alignment.
<221> NAME/KEY: misc_feature
<222> LOCATION: (2468)..(2468)
<223> OTHER INFORMATION: Sequences not determined at this position .
      Unknown residue put in to provide alignment.
<221> NAME/KEY: misc_feature
<222> LOCATION: (2493)..(2493)
<223> OTHER INFORMATION: Sequences not determined at this position .
      Unknown residue put in to provide alignment.
<221> NAME/KEY: misc_feature
<222> LOCATION: (2536)..(2860)
<223> OTHER INFORMATION: Sequences not determined at this position .
      Unknown residue put in to provide alignment.
<221> NAME/KEY: misc_feature
<222> LOCATION: (3163)..(3163)
<223> OTHER INFORMATION: Sequences not determined at this position .
      Unknown residue put in to provide alignment.
<221> NAME/KEY: misc_feature
<222> LOCATION: (3488)..(3499)
<223> OTHER INFORMATION: Sequences not determined at this position .
      Unknown residue put in to provide alignment.

<400> SEQUENCE: 1

nnn nnn nnn nnn nnn nnn nnn nnn nnn nnn nnn nnn nnn nnn nnn nnn       48
Xaa Xaa Xaa Xaa Xaa Xaa Xaa Xaa Xaa Xaa Xaa Xaa Xaa Xaa Xaa Xaa
1               5                   10                  15

nnn nnn nnn nnn nnn nnn nnn nnn nnn nnn nnn nnn nnn nnn nnn nnn       96
Xaa Xaa Xaa Xaa Xaa Xaa Xaa Xaa Xaa Xaa Xaa Xaa Xaa Xaa Xaa Xaa
            20                  25                  30

nnn nnn nnn nnn nnn nnn nnn nnn nnn nnn nnn nnn nnn nnn nnn nnn      144
Xaa Xaa Xaa Xaa Xaa Xaa Xaa Xaa Xaa Xaa Xaa Xaa Xaa Xaa Xaa Xaa
        35                  40                  45
```

-continued

```
nnn nnn nnn nnn nnn nnn nnn nnn nnn nnn nnn nnn nnn nnn nnn nnn      192
Xaa Xaa Xaa Xaa Xaa Xaa Xaa Xaa Xaa Xaa Xaa Xaa Xaa Xaa Xaa Xaa
    50                  55                  60

nnn nnn nnn nnn nnn nnn nnn nnn nnn nnn nnn nnn nnn nnn nnn nnn      240
Xaa Xaa Xaa Xaa Xaa Xaa Xaa Xaa Xaa Xaa Xaa Xaa Xaa Xaa Xaa Xaa
65                  70                  75                  80

nnn nnn nnn nnn nnn nnn nnn nnn nnn nnn nnn nnn nnn nnn nnn nnn      288
Xaa Xaa Xaa Xaa Xaa Xaa Xaa Xaa Xaa Xaa Xaa Xaa Xaa Xaa Xaa Xaa
                85                  90                  95

nnn nnn nnn nnn nnn nnn nnn nnn nnn nnn nnn nnn nnn nnn nnn nnn      336
Xaa Xaa Xaa Xaa Xaa Xaa Xaa Xaa Xaa Xaa Xaa Xaa Xaa Xaa Xaa Xaa
            100                 105                 110

nnn nnn nnn nnn nnn nnn nnn nnn nnn nnn nnn nnn nnn nnn nnn nnn      384
Xaa Xaa Xaa Xaa Xaa Xaa Xaa Xaa Xaa Xaa Xaa Xaa Xaa Xaa Xaa Xaa
        115                 120                 125

nnn nnn nnn nnn nnn nnn nnn nnn nnn nnn nnn nnn nnn nnn nnn nnn      432
Xaa Xaa Xaa Xaa Xaa Xaa Xaa Xaa Xaa Xaa Xaa Xaa Xaa Xaa Xaa Xaa
    130                 135                 140

nnn nnn nnn nnn nnn nnn nnn nnn nnn nnn nnn nnn nnn nnn nnn nnn      480
Xaa Xaa Xaa Xaa Xaa Xaa Xaa Xaa Xaa Xaa Xaa Xaa Xaa Xaa Xaa Xaa
145                 150                 155                 160

nnn nnn nnn nnn nnn nnn nnn nnn nnn nnn nnn nnn nnn nnn nnn nnn      528
Xaa Xaa Xaa Xaa Xaa Xaa Xaa Xaa Xaa Xaa Xaa Xaa Xaa Xaa Xaa Xaa
                165                 170                 175

nnn nnn nnn nnn nnn nnn nnn nnn nnn nnn nnn nnn nnn nnn nnn nnn      576
Xaa Xaa Xaa Xaa Xaa Xaa Xaa Xaa Xaa Xaa Xaa Xaa Xaa Xaa Xaa Xaa
            180                 185                 190

nnn nnn nnn naa cca ttc cnn agg ctg gtg acc cct gaa aag gtn aac      624
Xaa Xaa Xaa Xaa Pro Phe Xaa Arg Leu Val Thr Pro Glu Lys Val Asn
        195                 200                 205

anc cnc aac acg gng ggc agg aaa tcc acc ccg ctg cac ttc ccc gca      672
Xaa Xaa Asn Thr Xaa Gly Arg Lys Ser Thr Pro Leu His Phe Pro Ala
    210                 215                 220

ggt ttt ggg cgg aaa aac ctn ntt aaa tat ttg ctt caa aat ggt gca      720
Gly Phe Gly Arg Lys Asn Xaa Xaa Lys Tyr Leu Leu Gln Asn Gly Ala
225                 230                 235                 240

aat ntc caa nca ctt tat aat ggg ggc ctt att cct ctt cat ant gca      768
Asn Xaa Gln Xaa Leu Tyr Asn Gly Gly Leu Ile Pro Leu His Xaa Ala
                245                 250                 255

tgc tct ttt ggt cat gct aaa ant atc aat ctc ctt ttg cga cat ggt      816
Cys Ser Phe Gly His Ala Lys Xaa Ile Asn Leu Leu Leu Arg His Gly
            260                 265                 270

gca gac ccc aat gct cga gat aat tgg aat tat act cct ctc cat gaa      864
Ala Asp Pro Asn Ala Arg Asp Asn Trp Asn Tyr Thr Pro Leu His Glu
        275                 280                 285

gct gca att aaa gga aag att gat gtt tgc att gtg ctg tta cag cat      912
Ala Ala Ile Lys Gly Lys Ile Asp Val Cys Ile Val Leu Leu Gln His
    290                 295                 300

gga gct gag cca acc atc cga aat aca gat gga agg aca gca ttg gat      960
Gly Ala Glu Pro Thr Ile Arg Asn Thr Asp Gly Arg Thr Ala Leu Asp
305                 310                 315                 320

tta gca gat cca tct gcc aaa gca gtg ctt act ggt gaa tat aag aaa     1008
Leu Ala Asp Pro Ser Ala Lys Ala Val Leu Thr Gly Glu Tyr Lys Lys
                325                 330                 335

gat gaa ctc tta gaa agt gcc agg agt ggc aat gaa gaa aaa atg atg     1056
Asp Glu Leu Leu Glu Ser Ala Arg Ser Gly Asn Glu Glu Lys Met Met
            340                 345                 350

gct cta ctc aca cca tta aat gtc aac tgc cac gca agt gat ggc aga     1104
Ala Leu Leu Thr Pro Leu Asn Val Asn Cys His Ala Ser Asp Gly Arg
```

-continued

```
        355                 360                 365

aag tca act cca tta cat ttg gca gca gga tat aac aga gta aag att     1152
Lys Ser Thr Pro Leu His Leu Ala Ala Gly Tyr Asn Arg Val Lys Ile
    370                 375                 380

gta cag ctg tta ctg caa cat gga gct gat gtc cat gct aaa gat aaa     1200
Val Gln Leu Leu Leu Gln His Gly Ala Asp Val His Ala Lys Asp Lys
385                 390                 395                 400

ggt gat ctg gta cca tta cac aat gcc tgt tct tat ggt cat tat gaa     1248
Gly Asp Leu Val Pro Leu His Asn Ala Cys Ser Tyr Gly His Tyr Glu
                405                 410                 415

gta act gaa ctt ttg gtc aag cat ggt gcc tgt gta aat gca atg gac     1296
Val Thr Glu Leu Leu Val Lys His Gly Ala Cys Val Asn Ala Met Asp
            420                 425                 430

ttg tgg caa ttc act cct ctt cat gag gca gct tct aag aac agg gtt     1344
Leu Trp Gln Phe Thr Pro Leu His Glu Ala Ala Ser Lys Asn Arg Val
        435                 440                 445

gaa gta tgt tct ctt ctc tta agt tat ggt gca gac cca aca ctg ctc     1392
Glu Val Cys Ser Leu Leu Leu Ser Tyr Gly Ala Asp Pro Thr Leu Leu
    450                 455                 460

aat tgt cac aat aaa agt gct ata gac ttg gct ccc aca cca cag tta     1440
Asn Cys His Asn Lys Ser Ala Ile Asp Leu Ala Pro Thr Pro Gln Leu
465                 470                 475                 480

aaa gaa aga tta gca tat gaa ttt aaa ggc cac tcg ttg ctg caa gct     1488
Lys Glu Arg Leu Ala Tyr Glu Phe Lys Gly His Ser Leu Leu Gln Ala
                485                 490                 495

gca cga gaa gct gat gtt act cga atc aaa aaa cat ctc tct ctg gaa     1536
Ala Arg Glu Ala Asp Val Thr Arg Ile Lys Lys His Leu Ser Leu Glu
            500                 505                 510

atg gtg aat ttc aag cat cct caa aca cat gaa aca gca ttg cat tgt     1584
Met Val Asn Phe Lys His Pro Gln Thr His Glu Thr Ala Leu His Cys
        515                 520                 525

gct gct gca tct cca tat ccc aaa aga aag caa ata tgt gaa ctg ttg     1632
Ala Ala Ala Ser Pro Tyr Pro Lys Arg Lys Gln Ile Cys Glu Leu Leu
    530                 535                 540

cta aga aaa gga gca aac atc aat gaa aag act aaa gaa ttc ttg act     1680
Leu Arg Lys Gly Ala Asn Ile Asn Glu Lys Thr Lys Glu Phe Leu Thr
545                 550                 555                 560

cct ctg cac gtg gca tct gag aaa gct cat aat gat gtt gtt gaa gta     1728
Pro Leu His Val Ala Ser Glu Lys Ala His Asn Asp Val Val Glu Val
                565                 570                 575

gtg gtg aaa cat gaa gca aag gtt aat gct ctg gat aat ctt ggt cag     1776
Val Val Lys His Glu Ala Lys Val Asn Ala Leu Asp Asn Leu Gly Gln
            580                 585                 590

act tct cta cac aga gct gca tat tgt ggt cat cta caa acc tgc cgc     1824
Thr Ser Leu His Arg Ala Ala Tyr Cys Gly His Leu Gln Thr Cys Arg
        595                 600                 605

cta ctc ctg agc tat ggg tgt gat cct aac att ata tcc ctt cag ggc     1872
Leu Leu Leu Ser Tyr Gly Cys Asp Pro Asn Ile Ile Ser Leu Gln Gly
    610                 615                 620

ttt act gct tta cag atg gga aat gaa aat gta cag caa ctc ctc caa     1920
Phe Thr Ala Leu Gln Met Gly Asn Glu Asn Val Gln Gln Leu Leu Gln
625                 630                 635                 640

gag ggt atc tca tta ggt aat tca gag gca gac aga caa ttg ctg gaa     1968
Glu Gly Ile Ser Leu Gly Asn Ser Glu Ala Asp Arg Gln Leu Leu Glu
                645                 650                 655

gct gca aag gct gga gat gtc gaa act gta aaa aaa ctg tgt act gtt     2016
Ala Ala Lys Ala Gly Asp Val Glu Thr Val Lys Lys Leu Cys Thr Val
            660                 665                 670

cag agt gtc aac tgc aga gac att gaa ggg cgt cag tct aca cca ctt     2064
```

-continued

```
Gln Ser Val Asn Cys Arg Asp Ile Glu Gly Arg Gln Ser Thr Pro Leu
        675                 680                 685

cat ttt gca gct ggg tat aac aga gtg tcc gtg gtg gaa tat ctg cta      2112
His Phe Ala Ala Gly Tyr Asn Arg Val Ser Val Val Glu Tyr Leu Leu
    690                 695                 700

cag cat gga gct gat gtg cat gct aaa gat aaa ggn ggc ctt gta cct      2160
Gln His Gly Ala Asp Val His Ala Lys Asp Lys Gly Gly Leu Val Pro
705                 710                 715                 720

ttg cac aat gca tgt tnt tat gga cat tat gaa gtt gca gaa ctt ctt      2208
Leu His Asn Ala Cys Xaa Tyr Gly His Tyr Glu Val Ala Glu Leu Leu
                725                 730                 735

gtt aaa cat gga gca gta gtt aat gta gct gat tta tgg aaa ttt aca      2256
Val Lys His Gly Ala Val Val Asn Val Ala Asp Leu Trp Lys Phe Thr
            740                 745                 750

cct tta cat gaa gca gca gca aaa gga aaa tat gaa att tgc aaa ctt      2304
Pro Leu His Glu Ala Ala Ala Lys Gly Lys Tyr Glu Ile Cys Lys Leu
        755                 760                 765

ctg ctc cag cat ggt gca gac cct aca aaa aaa aac agg gat gga aat      2352
Leu Leu Gln His Gly Ala Asp Pro Thr Lys Lys Asn Arg Asp Gly Asn
    770                 775                 780

act ctt ttg gat ctt gtt aaa gat gga gan aca gat att caa gat ntg      2400
Thr Leu Leu Asp Leu Val Lys Asp Gly Xaa Thr Asp Ile Gln Asp Xaa
785                 790                 795                 800

ctt agg gga gat gca gtt ttg tta gat gct gcc aag aag ggt tgt tta      2448
Leu Arg Gly Asp Ala Val Leu Leu Asp Ala Ala Lys Lys Gly Cys Leu
                805                 810                 815

gcc aga gtg aag aag ttn tnt ttt cct gat aat gta aat tgc cgn gat      2496
Ala Arg Val Lys Lys Xaa Xaa Phe Pro Asp Asn Val Asn Cys Arg Asp
            820                 825                 830

acc caa ggc aga cat tca aca cct tta cat tta gca ggt nnn nnn nnn      2544
Thr Gln Gly Arg His Ser Thr Pro Leu His Leu Ala Gly Xaa Xaa Xaa
        835                 840                 845

nnn nnn nnn nnn nnn nnn nnn nnn nnn nnn nnn nnn nnn nnn nnn nnn      2592
Xaa Xaa Xaa Xaa Xaa Xaa Xaa Xaa Xaa Xaa Xaa Xaa Xaa Xaa Xaa Xaa
    850                 855                 860

nnn nnn nnn nnn nnn nnn nnn nnn nnn nnn nnn nnn nnn nnn nnn nnn      2640
Xaa Xaa Xaa Xaa Xaa Xaa Xaa Xaa Xaa Xaa Xaa Xaa Xaa Xaa Xaa Xaa
865                 870                 875                 880

nnn nnn nnn nnn nnn nnn nnn nnn nnn nnn nnn nnn nnn nnn nnn nnn      2688
Xaa Xaa Xaa Xaa Xaa Xaa Xaa Xaa Xaa Xaa Xaa Xaa Xaa Xaa Xaa Xaa
                885                 890                 895

nnn nnn nnn nnn nnn nnn nnn nnn nnn nnn nnn nnn nnn nnn nnn nnn      2736
Xaa Xaa Xaa Xaa Xaa Xaa Xaa Xaa Xaa Xaa Xaa Xaa Xaa Xaa Xaa Xaa
            900                 905                 910

nnn nnn nnn nnn nnn nnn nnn nnn nnn nnn nnn nnn nnn nnn nnn nnn      2784
Xaa Xaa Xaa Xaa Xaa Xaa Xaa Xaa Xaa Xaa Xaa Xaa Xaa Xaa Xaa Xaa
        915                 920                 925

nnn nnn nnn nnn nnn nnn nnn nnn nnn nnn nnn nnn nnn nnn nnn nnn      2832
Xaa Xaa Xaa Xaa Xaa Xaa Xaa Xaa Xaa Xaa Xaa Xaa Xaa Xaa Xaa Xaa
    930                 935                 940

nnn nnn nnn nnn nnn nnn nnn nnn nnn ntg aca gca gcc atg ccc cca      2880
Xaa Xaa Xaa Xaa Xaa Xaa Xaa Xaa Xaa Xaa Thr Ala Ala Met Pro Pro
945                 950                 955                 960

tct gtt ctg ccc tct tgt aac aag cct caa gtg ctc aat ggt gtg aga      2928
Ser Val Leu Pro Ser Cys Asn Lys Pro Gln Val Leu Asn Gly Val Arg
                965                 970                 975

agc cca gga gcc act gca gat gct ctc tct tca ggt cca tct agc cca      2976
Ser Pro Gly Ala Thr Ala Asp Ala Leu Ser Ser Gly Pro Ser Ser Pro
            980                 985                 990
```

-continued

```
tca agc ctt tct gca gcc agc agt  ctt gac aac tta tct  ggg agt ttt    3024
Ser Ser Leu Ser Ala Ala Ser Ser  Leu Asp Asn Leu Ser  Gly Ser Phe
        995                 1000                1005

tca gaa  ctg tct tca gta gtt  agt tca agt gga aca  gag ggt gct      3069
Ser Glu  Leu Ser Ser Val Val  Ser Ser Ser Gly Thr  Glu Gly Ala
    1010                 1015                1020

tcc agt  ttg gag aaa aag gag  gtt cca gga gta gat  ttt agc ata      3114
Ser Ser  Leu Glu Lys Lys Glu  Val Pro Gly Val Asp  Phe Ser Ile
    1025                 1030                1035

act caa  ttc gta agg aat ctt  gga ctt gag cac cta  atg gat ata      3159
Thr Gln  Phe Val Arg Asn Leu  Gly Leu Glu His Leu  Met Asp Ile
    1040                 1045                1050

ttt nag  aga gaa cag atc act  ttg gat gta tta gtt  gag atg ggg      3204
Phe Xaa  Arg Glu Gln Ile Thr  Leu Asp Val Leu Val  Glu Met Gly
    1055                 1060                1065

cac aag  gag ctg aag gag att  ggw atc aat gct tat  gga cat agg      3249
His Lys  Glu Leu Lys Glu Ile  Xaa Ile Asn Ala Tyr  Gly His Arg
    1070                 1075                1080

cac aaa  cta att aaa gga gtc  gag aga ctt atc tcc  gga caa caa      3294
His Lys  Leu Ile Lys Gly Val  Glu Arg Leu Ile Ser  Gly Gln Gln
    1085                 1090                1095

ggt ctt  aac cca tat tta act  ttg aac acc tct ggt  agt gga aca      3339
Gly Leu  Asn Pro Tyr Leu Thr  Leu Asn Thr Ser Gly  Ser Gly Thr
    1100                 1105                1110

att ctt  ata gat ctg tct cct  gat gat aaa gag ttt  cag tct gtg      3384
Ile Leu  Ile Asp Leu Ser Pro  Asp Asp Lys Glu Phe  Gln Ser Val
    1115                 1120                1125

gag gaa  gag atg caa agt aca  gtt cga gag cac aga  gat gga ggt      3429
Glu Glu  Glu Met Gln Ser Thr  Val Arg Glu His Arg  Asp Gly Gly
    1130                 1135                1140

cat gca  ggt gga atc ttc aac  aga tac aat att ctc  aag att cag      3474
His Ala  Gly Gly Ile Phe Asn  Arg Tyr Asn Ile Leu  Lys Ile Gln
    1145                 1150                1155

aag gtt  tgt aac ann nnn nnn  nnn nga gcc aag att  cgg cac gag      3519
Lys Val  Cys Asn Xaa Xaa Xaa  Xaa Xaa Ala Lys Ile  Arg His Glu
    1160                 1165                1170

gaa aga  tac act cac cgg aga  aaa gaa gtt tct gaa  gaa aac cac      3564
Glu Arg  Tyr Thr His Arg Arg  Lys Glu Val Ser Glu  Glu Asn His
    1175                 1180                1185

aac cat  gcc aat gaa cga atg  cta ttt cat ggg tct  cct ttt gtg      3609
Asn His  Ala Asn Glu Arg Met  Leu Phe His Gly Ser  Pro Phe Val
    1190                 1195                1200

aat gca  att atc cac aaa ggc  ttt gat gaa agg cat  gcg tac ata      3654
Asn Ala  Ile Ile His Lys Gly  Phe Asp Glu Arg His  Ala Tyr Ile
    1205                 1210                1215

ggt ggt  atg ttt gga gct ggc  att tat ttt gct gaa  aac tct tcc      3699
Gly Gly  Met Phe Gly Ala Gly  Ile Tyr Phe Ala Glu  Asn Ser Ser
    1220                 1225                1230

aaa agc  aat caa tat gta tat  gga att gga gga ggt  act ggg tgt      3744
Lys Ser  Asn Gln Tyr Val Tyr  Gly Ile Gly Gly Gly  Thr Gly Cys
    1235                 1240                1245

cca gtt  cac aaa gac aga tct  tgt tac att tgc cac  agg cag ctg      3789
Pro Val  His Lys Asp Arg Ser  Cys Tyr Ile Cys His  Arg Gln Leu
    1250                 1255                1260

ctc ttt  tgc cgg gta acc ttg  gga aag tct ttc ctg  cag ttc agt      3834
Leu Phe  Cys Arg Val Thr Leu  Gly Lys Ser Phe Leu  Gln Phe Ser
    1265                 1270                1275

gca atg  aaa atg gca cat tct  cct cca ggt cat cac  tca gtc act      3879
Ala Met  Lys Met Ala His Ser  Pro Pro Gly His His  Ser Val Thr
    1280                 1285                1290
```

-continued

```
ggt agg  ccc agt gta aat ggc  cta gca tta gct gaa  tat gtt att      3924
Gly Arg  Pro Ser Val Asn Gly  Leu Ala Leu Ala Glu  Tyr Val Ile
    1295                 1300                 1305

tac aga  gga gaa cag gct tat  cct gag tat tta att  act tac cag      3969
Tyr Arg  Gly Glu Gln Ala Tyr  Pro Glu Tyr Leu Ile  Thr Tyr Gln
    1310                 1315                 1320

att atg  agg cct gaa ggt atg  gtc gat gga taaatagtta ttttaagaaa     4019
Ile Met  Arg Pro Glu Gly Met  Val Asp Gly
    1325                 1330

ctaattccac tgaacctaaa atcatcaaag cagcagtggc ctctacgttt tactcctttg   4079

ctgaaaaaaa atcatcttgc ccacaggcct gtggcaaaag gataaaaatg tgaacgaagt   4139

ttaacattct gacttgataa agctttaata atgtacagtg ttttctaaat atttcctgtt   4199

ttttcagcac tttaacagat gccattccag gttaaactgg gttgtctgta ctaaattata   4259

aacagagtta acttgaacct tttatatgtt atgcattgat tctaacaaac tgtaatgccc   4319

tcaacagaac taattttact aatacaatac tgtgttcttt aaaacacagc atttacactg   4379

aatacaattt catttgtaaa actgtaaata agagcttttg tactagccca gtatttattt   4439

acattgcttt gtaatataaa tctgttttag aactgcaaaa aaaaaaaaaa aaaa         4493
```

<210> SEQ ID NO 2
<211> LENGTH: 1333
<212> TYPE: PRT
<213> ORGANISM: Homo sapiens
<220> FEATURE:
<221> NAME/KEY: misc_feature
<222> LOCATION: (1)..(1)
<223> OTHER INFORMATION: The 'Xaa' at location 1 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (2)..(2)
<223> OTHER INFORMATION: The 'Xaa' at location 2 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (3)..(3)
<223> OTHER INFORMATION: The 'Xaa' at location 3 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (4)..(4)
<223> OTHER INFORMATION: The 'Xaa' at location 4 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (5)..(5)
<223> OTHER INFORMATION: The 'Xaa' at location 5 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (6)..(6)
<223> OTHER INFORMATION: The 'Xaa' at location 6 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (7)..(7)
<223> OTHER INFORMATION: The 'Xaa' at location 7 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (8)..(8)
<223> OTHER INFORMATION: The 'Xaa' at location 8 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (9)..(9)
<223> OTHER INFORMATION: The 'Xaa' at location 9 stands for Lys, Asn, Arg, Ser, Thr, Ile, Met, Glu, Asp, Gly, Ala, Val, Gln, His, Pro, -continued

```
      Leu, a stop codon, Tyr, Trp, Cys, or Phe.
<221> NAME/KEY: misc_feature
<222> LOCATION: (10)..(10)
<223> OTHER INFORMATION: The 'Xaa' at location 10 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (11)..(11)
<223> OTHER INFORMATION: The 'Xaa' at location 11 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (12)..(12)
<223> OTHER INFORMATION: The 'Xaa' at location 12 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (13)..(13)
<223> OTHER INFORMATION: The 'Xaa' at location 13 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (14)..(14)
<223> OTHER INFORMATION: The 'Xaa' at location 14 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (15)..(15)
<223> OTHER INFORMATION: The 'Xaa' at location 15 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (16)..(16)
<223> OTHER INFORMATION: The 'Xaa' at location 16 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (17)..(17)
<223> OTHER INFORMATION: The 'Xaa' at location 17 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (18)..(18)
<223> OTHER INFORMATION: The 'Xaa' at location 18 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (19)..(19)
<223> OTHER INFORMATION: The 'Xaa' at location 19 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (20)..(20)
<223> OTHER INFORMATION: The 'Xaa' at location 20 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (21)..(21)
<223> OTHER INFORMATION: The 'Xaa' at location 21 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (22)..(22)
<223> OTHER INFORMATION: The 'Xaa' at location 22 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (23)..(23)
<223> OTHER INFORMATION: The 'Xaa' at location 23 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (24)..(24)
<223> OTHER INFORMATION: The 'Xaa' at location 24 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (25)..(25)
<223> OTHER INFORMATION: The 'Xaa' at location 25 stands for Lys, Asn,
```

-continued

Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (26)..(26)
<223> OTHER INFORMATION: The 'Xaa' at location 26 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (27)..(27)
<223> OTHER INFORMATION: The 'Xaa' at location 27 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (28)..(28)
<223> OTHER INFORMATION: The 'Xaa' at location 28 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (29)..(29)
<223> OTHER INFORMATION: The 'Xaa' at location 29 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (30)..(30)
<223> OTHER INFORMATION: The 'Xaa' at location 30 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (31)..(31)
<223> OTHER INFORMATION: The 'Xaa' at location 31 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (32)..(32)
<223> OTHER INFORMATION: The 'Xaa' at location 32 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (33)..(33)
<223> OTHER INFORMATION: The 'Xaa' at location 33 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (34)..(34)
<223> OTHER INFORMATION: The 'Xaa' at location 34 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (35)..(35)
<223> OTHER INFORMATION: The 'Xaa' at location 35 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (36)..(36)
<223> OTHER INFORMATION: The 'Xaa' at location 36 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (37)..(37)
<223> OTHER INFORMATION: The 'Xaa' at location 37 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (38)..(38)
<223> OTHER INFORMATION: The 'Xaa' at location 38 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (39)..(39)
<223> OTHER INFORMATION: The 'Xaa' at location 39 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (40)..(40)
<223> OTHER INFORMATION: The 'Xaa' at location 40 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (41)..(41)

-continued

<223> OTHER INFORMATION: The 'Xaa' at location 41 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (42)..(42)
<223> OTHER INFORMATION: The 'Xaa' at location 42 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (43)..(43)
<223> OTHER INFORMATION: The 'Xaa' at location 43 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (44)..(44)
<223> OTHER INFORMATION: The 'Xaa' at location 44 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (45)..(45)
<223> OTHER INFORMATION: The 'Xaa' at location 45 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (46)..(46)
<223> OTHER INFORMATION: The 'Xaa' at location 46 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (47)..(47)
<223> OTHER INFORMATION: The 'Xaa' at location 47 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (48)..(48)
<223> OTHER INFORMATION: The 'Xaa' at location 48 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (49)..(49)
<223> OTHER INFORMATION: The 'Xaa' at location 49 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (50)..(50)
<223> OTHER INFORMATION: The 'Xaa' at location 50 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (51)..(51)
<223> OTHER INFORMATION: The 'Xaa' at location 51 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (52)..(52)
<223> OTHER INFORMATION: The 'Xaa' at location 52 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (53)..(53)
<223> OTHER INFORMATION: The 'Xaa' at location 53 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (54)..(54)
<223> OTHER INFORMATION: The 'Xaa' at location 54 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (55)..(55)
<223> OTHER INFORMATION: The 'Xaa' at location 55 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (56)..(56)
<223> OTHER INFORMATION: The 'Xaa' at location 56 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature -continued
<222> LOCATION: (57)..(57)
<223> OTHER INFORMATION: The 'Xaa' at location 57 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (58)..(58)
<223> OTHER INFORMATION: The 'Xaa' at location 58 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (59)..(59)
<223> OTHER INFORMATION: The 'Xaa' at location 59 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (60)..(60)
<223> OTHER INFORMATION: The 'Xaa' at location 60 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (61)..(61)
<223> OTHER INFORMATION: The 'Xaa' at location 61 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (62)..(62)
<223> OTHER INFORMATION: The 'Xaa' at location 62 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (63)..(63)
<223> OTHER INFORMATION: The 'Xaa' at location 63 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (64)..(64)
<223> OTHER INFORMATION: The 'Xaa' at location 64 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (65)..(65)
<223> OTHER INFORMATION: The 'Xaa' at location 65 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (66)..(66)
<223> OTHER INFORMATION: The 'Xaa' at location 66 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (67)..(67)
<223> OTHER INFORMATION: The 'Xaa' at location 67 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (68)..(68)
<223> OTHER INFORMATION: The 'Xaa' at location 68 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (69)..(69)
<223> OTHER INFORMATION: The 'Xaa' at location 69 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (70)..(70)
<223> OTHER INFORMATION: The 'Xaa' at location 70 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (71)..(71)
<223> OTHER INFORMATION: The 'Xaa' at location 71 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (72)..(72)
<223> OTHER INFORMATION: The 'Xaa' at location 72 stands for Lys, Asn, Arg, Ser, Thr, Ile, Met, Glu, Asp, Gly, Ala, Val, Gln, His, Pro, Leu, a stop codon, Tyr, Trp, Cys, or Phe.

-continued

<221> NAME/KEY: misc_feature
<222> LOCATION: (73)..(73)
<223> OTHER INFORMATION: The 'Xaa' at location 73 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (74)..(74)
<223> OTHER INFORMATION: The 'Xaa' at location 74 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (75)..(75)
<223> OTHER INFORMATION: The 'Xaa' at location 75 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (76)..(76)
<223> OTHER INFORMATION: The 'Xaa' at location 76 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (77)..(77)
<223> OTHER INFORMATION: The 'Xaa' at location 77 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (78)..(78)
<223> OTHER INFORMATION: The 'Xaa' at location 78 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (79)..(79)
<223> OTHER INFORMATION: The 'Xaa' at location 79 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (80)..(80)
<223> OTHER INFORMATION: The 'Xaa' at location 80 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (81)..(81)
<223> OTHER INFORMATION: The 'Xaa' at location 81 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (82)..(82)
<223> OTHER INFORMATION: The 'Xaa' at location 82 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (83)..(83)
<223> OTHER INFORMATION: The 'Xaa' at location 83 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (84)..(84)
<223> OTHER INFORMATION: The 'Xaa' at location 84 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (85)..(85)
<223> OTHER INFORMATION: The 'Xaa' at location 85 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (86)..(86)
<223> OTHER INFORMATION: The 'Xaa' at location 86 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (87)..(87)
<223> OTHER INFORMATION: The 'Xaa' at location 87 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (88)..(88)
<223> OTHER INFORMATION: The 'Xaa' at location 88 stands for Lys, Asn, Arg, Ser, Thr, Ile, Met, Glu, Asp, Gly, Ala, Val, Gln, His, Pro, -continued Leu, a stop codon, Tyr, Trp, Cys, or Phe.
<221> NAME/KEY: misc_feature
<222> LOCATION: (89)..(89)
<223> OTHER INFORMATION: The 'Xaa' at location 89 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (90)..(90)
<223> OTHER INFORMATION: The 'Xaa' at location 90 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (91)..(91)
<223> OTHER INFORMATION: The 'Xaa' at location 91 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (92)..(92)
<223> OTHER INFORMATION: The 'Xaa' at location 92 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (93)..(93)
<223> OTHER INFORMATION: The 'Xaa' at location 93 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (94)..(94)
<223> OTHER INFORMATION: The 'Xaa' at location 94 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (95)..(95)
<223> OTHER INFORMATION: The 'Xaa' at location 95 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (96)..(96)
<223> OTHER INFORMATION: The 'Xaa' at location 96 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (97)..(97)
<223> OTHER INFORMATION: The 'Xaa' at location 97 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (98)..(98)
<223> OTHER INFORMATION: The 'Xaa' at location 98 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (99)..(99)
<223> OTHER INFORMATION: The 'Xaa' at location 99 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (100)..(100)
<223> OTHER INFORMATION: The 'Xaa' at location 100 stands for Lys, Asn Arg, Ser, Thr, Ile , Met, Glu, Asp, Gly, Ala, Val, Gln, His, Pro, Leu, a stop codon, Tyr, Trp, Cys, or Phe.
<221> NAME/KEY: misc_feature
<222> LOCATION: (101)..(101)
<223> OTHER INFORMATION: The 'Xaa' at location 101 stands for Lys, Asn Arg, Ser, Thr, Ile , Met, Glu, Asp, Gly, Ala, Val, Gln, His, Pro, Leu, a stop codon, Tyr, Trp, Cys, or Phe.
<221> NAME/KEY: misc_feature
<222> LOCATION: (102)..(102)
<223> OTHER INFORMATION: The 'Xaa' at location 102 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (103)..(103)
<223> OTHER INFORMATION: The 'Xaa' at location 103 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (104)..(104)
<223> OTHER INFORMATION: The 'Xaa' at location 104 stands for Lys, Asn, -continued

```
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (105)..(105)
<223> OTHER INFORMATION: The 'Xaa' at location 105 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (106)..(106)
<223> OTHER INFORMATION: The 'Xaa' at location 106 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (107)..(107)
<223> OTHER INFORMATION: The 'Xaa' at location 107 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (108)..(108)
<223> OTHER INFORMATION: The 'Xaa' at location 108 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (109)..(109)
<223> OTHER INFORMATION: The 'Xaa' at location 109 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (110)..(110)
<223> OTHER INFORMATION: The 'Xaa' at location 110 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (111)..(111)
<223> OTHER INFORMATION: The 'Xaa' at location 111 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (112)..(112)
<223> OTHER INFORMATION: The 'Xaa' at location 112 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (113)..(113)
<223> OTHER INFORMATION: The 'Xaa' at location 113 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (114)..(114)
<223> OTHER INFORMATION: The 'Xaa' at location 114 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (115)..(115)
<223> OTHER INFORMATION: The 'Xaa' at location 115 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (116)..(116)
<223> OTHER INFORMATION: The 'Xaa' at location 116 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (117)..(117)
<223> OTHER INFORMATION: The 'Xaa' at location 117 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (118)..(118)
<223> OTHER INFORMATION: The 'Xaa' at location 118 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (119)..(119)
<223> OTHER INFORMATION: The 'Xaa' at location 119 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (120)..(120)
```

-continued

<223> OTHER INFORMATION: The 'Xaa' at location 120 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (121)..(121)
<223> OTHER INFORMATION: The 'Xaa' at location 121 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (122)..(122)
<223> OTHER INFORMATION: The 'Xaa' at location 122 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (123)..(123)
<223> OTHER INFORMATION: The 'Xaa' at location 123 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (124)..(124)
<223> OTHER INFORMATION: The 'Xaa' at location 124 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (125)..(125)
<223> OTHER INFORMATION: The 'Xaa' at location 125 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (126)..(126)
<223> OTHER INFORMATION: The 'Xaa' at location 126 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (127)..(127)
<223> OTHER INFORMATION: The 'Xaa' at location 127 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (128)..(128)
<223> OTHER INFORMATION: The 'Xaa' at location 128 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (129)..(129)
<223> OTHER INFORMATION: The 'Xaa' at location 129 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (130)..(130)
<223> OTHER INFORMATION: The 'Xaa' at location 130 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (131)..(131)
<223> OTHER INFORMATION: The 'Xaa' at location 131 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (132)..(132)
<223> OTHER INFORMATION: The 'Xaa' at location 132 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (133)..(133)
<223> OTHER INFORMATION: The 'Xaa' at location 133 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (134)..(134)
<223> OTHER INFORMATION: The 'Xaa' at location 134 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (135)..(135)
<223> OTHER INFORMATION: The 'Xaa' at location 135 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature -continued
<222> LOCATION: (136)..(136)
<223> OTHER INFORMATION: The 'Xaa' at location 136 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (137)..(137)
<223> OTHER INFORMATION: The 'Xaa' at location 137 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (138)..(138)
<223> OTHER INFORMATION: The 'Xaa' at location 138 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (139)..(139)
<223> OTHER INFORMATION: The 'Xaa' at location 139 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (140)..(140)
<223> OTHER INFORMATION: The 'Xaa' at location 140 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (141)..(141)
<223> OTHER INFORMATION: The 'Xaa' at location 141 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (142)..(142)
<223> OTHER INFORMATION: The 'Xaa' at location 142 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (143)..(143)
<223> OTHER INFORMATION: The 'Xaa' at location 143 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (144)..(144)
<223> OTHER INFORMATION: The 'Xaa' at location 144 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (145)..(145)
<223> OTHER INFORMATION: The 'Xaa' at location 145 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (146)..(146)
<223> OTHER INFORMATION: The 'Xaa' at location 146 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (147)..(147)
<223> OTHER INFORMATION: The 'Xaa' at location 147 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (148)..(148)
<223> OTHER INFORMATION: The 'Xaa' at location 148 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (149)..(149)
<223> OTHER INFORMATION: The 'Xaa' at location 149 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (150)..(150)
<223> OTHER INFORMATION: The 'Xaa' at location 150 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (151)..(151)
<223> OTHER INFORMATION: The 'Xaa' at location 151 stands for Lys, Asn, Arg, Ser, Thr, Ile, Met, Glu, Asp, Gly, Ala, Val, Gln, His, Pro, Leu, a stop codon, Tyr, Trp, Cys, or Phe.

-continued

<221> NAME/KEY: misc_feature
<222> LOCATION: (152)..(152)
<223> OTHER INFORMATION: The 'Xaa' at location 152 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (153)..(153)
<223> OTHER INFORMATION: The 'Xaa' at location 153 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (154)..(154)
<223> OTHER INFORMATION: The 'Xaa' at location 154 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (155)..(155)
<223> OTHER INFORMATION: The 'Xaa' at location 155 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (156)..(156)
<223> OTHER INFORMATION: The 'Xaa' at location 156 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (157)..(157)
<223> OTHER INFORMATION: The 'Xaa' at location 157 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (158)..(158)
<223> OTHER INFORMATION: The 'Xaa' at location 158 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (159)..(159)
<223> OTHER INFORMATION: The 'Xaa' at location 159 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (160)..(160)
<223> OTHER INFORMATION: The 'Xaa' at location 160 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (161)..(161)
<223> OTHER INFORMATION: The 'Xaa' at location 161 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (162)..(162)
<223> OTHER INFORMATION: The 'Xaa' at location 162 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (163)..(163)
<223> OTHER INFORMATION: The 'Xaa' at location 163 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (164)..(164)
<223> OTHER INFORMATION: The 'Xaa' at location 164 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (165)..(165)
<223> OTHER INFORMATION: The 'Xaa' at location 165 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (166)..(166)
<223> OTHER INFORMATION: The 'Xaa' at location 166 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (167)..(167)
<223> OTHER INFORMATION: The 'Xaa' at location 167 stands for Lys, Asn, Arg, Ser, Thr, Ile, Met, Glu, Asp, Gly, Ala, Val, Gln, His, Pro, -continued

```
      Leu, a stop codon, Tyr, Trp, Cys, or Phe.
<221> NAME/KEY: misc_feature
<222> LOCATION: (168)..(168)
<223> OTHER INFORMATION: The 'Xaa' at location 168 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (169)..(169)
<223> OTHER INFORMATION: The 'Xaa' at location 169 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (170)..(170)
<223> OTHER INFORMATION: The 'Xaa' at location 170 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (171)..(171)
<223> OTHER INFORMATION: The 'Xaa' at location 171 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (172)..(172)
<223> OTHER INFORMATION: The 'Xaa' at location 172 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (173)..(173)
<223> OTHER INFORMATION: The 'Xaa' at location 173 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (174)..(174)
<223> OTHER INFORMATION: The 'Xaa' at location 174 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (175)..(175)
<223> OTHER INFORMATION: The 'Xaa' at location 175 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (176)..(176)
<223> OTHER INFORMATION: The 'Xaa' at location 176 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (177)..(177)
<223> OTHER INFORMATION: The 'Xaa' at location 177 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (178)..(178)
<223> OTHER INFORMATION: The 'Xaa' at location 178 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (179)..(179)
<223> OTHER INFORMATION: The 'Xaa' at location 179 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (180)..(180)
<223> OTHER INFORMATION: The 'Xaa' at location 180 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (181)..(181)
<223> OTHER INFORMATION: The 'Xaa' at location 181 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (182)..(182)
<223> OTHER INFORMATION: The 'Xaa' at location 182 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (183)..(183)
<223> OTHER INFORMATION: The 'Xaa' at location 183 stands for Lys, Asn,
```

-continued

```
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (184)..(184)
<223> OTHER INFORMATION: The 'Xaa' at location 184 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (185)..(185)
<223> OTHER INFORMATION: The 'Xaa' at location 185 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (186)..(186)
<223> OTHER INFORMATION: The 'Xaa' at location 186 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (187)..(187)
<223> OTHER INFORMATION: The 'Xaa' at location 187 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (188)..(188)
<223> OTHER INFORMATION: The 'Xaa' at location 188 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (189)..(189)
<223> OTHER INFORMATION: The 'Xaa' at location 189 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (190)..(190)
<223> OTHER INFORMATION: The 'Xaa' at location 190 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (191)..(191)
<223> OTHER INFORMATION: The 'Xaa' at location 191 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (192)..(192)
<223> OTHER INFORMATION: The 'Xaa' at location 192 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (193)..(193)
<223> OTHER INFORMATION: The 'Xaa' at location 193 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (194)..(194)
<223> OTHER INFORMATION: The 'Xaa' at location 194 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (195)..(195)
<223> OTHER INFORMATION: The 'Xaa' at location 195 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (196)..(196)
<223> OTHER INFORMATION: The 'Xaa' at location 196 stands for Lys, Glu,
      Gly, or a stop codon.
<221> NAME/KEY: misc_feature
<222> LOCATION: (199)..(199)
<223> OTHER INFORMATION: The 'Xaa' at location 199 stands for Gln, His,
      Arg, Pro, or Leu.
<221> NAME/KEY: misc_feature
      LOCATION: (209)..(209) OTHER INFORMATION: The 'Xaa' at location 209
      stands for Asn, Ser, Thr, or Ile.
<221> NAME/KEY: misc_feature
<222> LOCATION: (210)..(210)
<223> OTHER INFORMATION: The 'Xaa' at location 210 stands for His
      Arg, Pro, or Leu.
<221> NAME/KEY: misc_feature
<222> LOCATION: (213)..(213)
```

-continued

<223> OTHER INFORMATION: The 'Xaa' at location 213 stands for Glu, Gly, Ala, or Val.
<221> NAME/KEY: misc_feature
<222> LOCATION: (231)..(231)
<223> OTHER INFORMATION: The 'Xaa' at location 31 stands for Leu.
<221> NAME/KEY: misc_feature
<222> LOCATION: (232)..(232)
<223> OTHER INFORMATION: The 'Xaa' at location 232 stands for Ile, Val, Leu, or Phe.
<221> NAME/KEY: misc_feature
<222> LOCATION: (242)..(242)
<223> OTHER INFORMATION: The 'Xaa' at location 242 stands for Ile, Val, Leu, or Phe.
<221> NAME/KEY: misc_feature
<222> LOCATION: (244)..(244)
<223> OTHER INFORMATION: The 'Xaa' at location 244 stands for Thr, Ala, Pro, or Ser.
<221> NAME/KEY: misc_feature
<222> LOCATION: (255)..(255)
<223> OTHER INFORMATION: The 'Xaa' at location 255 stands for Asn, Ser, Thr, or Ile.
<221> NAME/KEY: misc_feature
<222> LOCATION: (264)..(264)
<223> OTHER INFORMATION: The 'Xaa' at location 264 stands for Asn, Ser, Thr, or Ile.
<221> NAME/KEY: misc_feature
<222> LOCATION: (726)..(726)
<223> OTHER INFORMATION: The 'Xaa' at location 726 stands for Tyr, Cys, Ser, or Phe.
<221> NAME/KEY: misc_feature
<222> LOCATION: (794)..(794)
<223> OTHER INFORMATION: The 'Xaa' at location 794 stands for Glu, or Asp.
<221> NAME/KEY: misc_feature
<222> LOCATION: (800)..(800)
<223> OTHER INFORMATION: The 'Xaa' at location 800 stands for Met, Val, or Leu.
<221> NAME/KEY: misc_feature
<222> LOCATION: (822)..(822)
<223> OTHER INFORMATION: The 'Xaa' at location 822 stands for Leu, or Phe.
<221> NAME/KEY: misc_feature
<222> LOCATION: (823)..(823)
<223> OTHER INFORMATION: The 'Xaa' at location 823 stands for Tyr, Cys, Ser, or Phe.
<221> NAME/KEY: misc_feature
<222> LOCATION: (846)..(846)
<223> OTHER INFORMATION: The 'Xaa' at location 846 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (847)..(847)
<223> OTHER INFORMATION: The 'Xaa' at location 847 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (848)..(848)
<223> OTHER INFORMATION: The 'Xaa' at location 848 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (849)..(849)
<223> OTHER INFORMATION: The 'Xaa' at location 849 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (850)..(850)
<223> OTHER INFORMATION: The 'Xaa' at location 850 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (851)..(851)
<223> OTHER INFORMATION: The 'Xaa' at location 851 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (852)..(852)
<223> OTHER INFORMATION: The 'Xaa' at location 852 stands for Lys, Asn, Arg, Ser, Thr, Ile, Met, Glu, Asp, Gly, Ala, Val, Gln, His, Pro, -continued Leu, a stop codon, Tyr, Trp, Cys, or Phe.
<221> NAME/KEY: misc_feature
<222> LOCATION: (853)..(853)
<223> OTHER INFORMATION: The 'Xaa' at location 853 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (854)..(854)
<223> OTHER INFORMATION: The 'Xaa' at location 854 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (855)..(855)
<223> OTHER INFORMATION: The 'Xaa' at location 855 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (856)..(856)
<223> OTHER INFORMATION: The 'Xaa' at location 856 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (857)..(857)
<223> OTHER INFORMATION: The 'Xaa' at location 857 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (858)..(858)
<223> OTHER INFORMATION: The 'Xaa' at location 858 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (859)..(859)
<223> OTHER INFORMATION: The 'Xaa' at location 859 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (860)..(860)
<223> OTHER INFORMATION: The 'Xaa' at location 860 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (861)..(861)
<223> OTHER INFORMATION: The 'Xaa' at location 861 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (862)..(862)
<223> OTHER INFORMATION: The 'Xaa' at location 862 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (863)..(863)
<223> OTHER INFORMATION: The 'Xaa' at location 863 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (864)..(864)
<223> OTHER INFORMATION: The 'Xaa' at location 864 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (865)..(865)
<223> OTHER INFORMATION: The 'Xaa' at location 865 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (866)..(866)
<223> OTHER INFORMATION: The 'Xaa' at location 866 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (867)..(867)
<223> OTHER INFORMATION: The 'Xaa' at location 867 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (868)..(868)
<223> OTHER INFORMATION: The 'Xaa' at location 868 stands for Lys, Asn, -continued

```
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (869)..(869)
<223> OTHER INFORMATION: The 'Xaa' at location 869 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (870)..(870)
<223> OTHER INFORMATION: The 'Xaa' at location 870 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (871)..(871)
<223> OTHER INFORMATION: The 'Xaa' at location 871 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (872)..(872)
<223> OTHER INFORMATION: The 'Xaa' at location 872 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (873)..(873)
<223> OTHER INFORMATION: The 'Xaa' at location 873 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (874)..(874)
<223> OTHER INFORMATION: The 'Xaa' at location 874 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (875)..(875)
<223> OTHER INFORMATION: The 'Xaa' at location 875 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (876)..(876)
<223> OTHER INFORMATION: The 'Xaa' at location 876 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (877)..(877)
<223> OTHER INFORMATION: The 'Xaa' at location 877 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (878)..(878)
<223> OTHER INFORMATION: The 'Xaa' at location 878 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (879)..(879)
<223> OTHER INFORMATION: The 'Xaa' at location 879 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (880)..(880)
<223> OTHER INFORMATION: The 'Xaa' at location 880 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (881)..(881)
<223> OTHER INFORMATION: The 'Xaa' at location 881 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (882)..(882)
<223> OTHER INFORMATION: The 'Xaa' at location 882 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (883)..(883)
<223> OTHER INFORMATION: The 'Xaa' at location 883 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (884)..(884)
```

-continued

<223> OTHER INFORMATION: The 'Xaa' at location 884 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (885)..(885)
<223> OTHER INFORMATION: The 'Xaa' at location 885 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (886)..(886)
<223> OTHER INFORMATION: The 'Xaa' at location 886 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (887)..(887)
<223> OTHER INFORMATION: The 'Xaa' at location 887 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (888)..(888)
<223> OTHER INFORMATION: The 'Xaa' at location 888 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (889)..(889)
<223> OTHER INFORMATION: The 'Xaa' at location 889 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (890)..(890)
<223> OTHER INFORMATION: The 'Xaa' at location 890 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (891)..(891)
<223> OTHER INFORMATION: The 'Xaa' at location 891 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (892)..(892)
<223> OTHER INFORMATION: The 'Xaa' at location 892 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (893)..(893)
<223> OTHER INFORMATION: The 'Xaa' at location 893 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (894)..(894)
<223> OTHER INFORMATION: The 'Xaa' at location 894 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (895)..(895)
<223> OTHER INFORMATION: The 'Xaa' at location 895 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (896)..(896)
<223> OTHER INFORMATION: The 'Xaa' at location 896 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (897)..(897)
<223> OTHER INFORMATION: The 'Xaa' at location 897 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (898)..(898)
<223> OTHER INFORMATION: The 'Xaa' at location 898 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (899)..(899)
<223> OTHER INFORMATION: The 'Xaa' at location 899 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature -continued
<222> LOCATION: (900)..(900)
<223> OTHER INFORMATION: The 'Xaa' at location 900 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (901)..(901)
<223> OTHER INFORMATION: The 'Xaa' at location 901 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (902)..(902)
<223> OTHER INFORMATION: The 'Xaa' at location 902 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (903)..(903)
<223> OTHER INFORMATION: The 'Xaa' at location 903 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (904)..(904)
<223> OTHER INFORMATION: The 'Xaa' at location 904 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (905)..(905)
<223> OTHER INFORMATION: The 'Xaa' at location 905 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (906)..(906)
<223> OTHER INFORMATION: The 'Xaa' at location 906 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (907)..(907)
<223> OTHER INFORMATION: The 'Xaa' at location 907 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (908)..(908)
<223> OTHER INFORMATION: The 'Xaa' at location 908 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (909)..(909)
<223> OTHER INFORMATION: The 'Xaa' at location 909 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (910)..(910)
<223> OTHER INFORMATION: The 'Xaa' at location 910 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (911)..(911)
<223> OTHER INFORMATION: The 'Xaa' at location 911 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (912)..(912)
<223> OTHER INFORMATION: The 'Xaa' at location 912 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (913)..(913)
<223> OTHER INFORMATION: The 'Xaa' at location 913 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (914)..(914)
<223> OTHER INFORMATION: The 'Xaa' at location 914 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (915)..(915)
<223> OTHER INFORMATION: The 'Xaa' at location 915 stands for Lys, Asn, Arg, Ser, Thr, Ile, Met, Glu, Asp, Gly, Ala, Val, Gln, His, Pro, Leu, a stop codon, Tyr, Trp, Cys, or Phe.

-continued

<221> NAME/KEY: misc_feature
<222> LOCATION: (916)..(916)
<223> OTHER INFORMATION: The 'Xaa' at location 916 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (917)..(917)
<223> OTHER INFORMATION: The 'Xaa' at location 917 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (918)..(918)
<223> OTHER INFORMATION: The 'Xaa' at location 918 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (919)..(919)
<223> OTHER INFORMATION: The 'Xaa' at location 919 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (920)..(920)
<223> OTHER INFORMATION: The 'Xaa' at location 920 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (921)..(921)
<223> OTHER INFORMATION: The 'Xaa' at location 921 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (922)..(922)
<223> OTHER INFORMATION: The 'Xaa' at location 922 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (923)..(923)
<223> OTHER INFORMATION: The 'Xaa' at location 923 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (924)..(924)
<223> OTHER INFORMATION: The 'Xaa' at location 924 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (925)..(925)
<223> OTHER INFORMATION: The 'Xaa' at location 925 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (926)..(926)
<223> OTHER INFORMATION: The 'Xaa' at location 926 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (927)..(927)
<223> OTHER INFORMATION: The 'Xaa' at location 927 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (928)..(928)
<223> OTHER INFORMATION: The 'Xaa' at location 928 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (929)..(929)
<223> OTHER INFORMATION: The 'Xaa' at location 929 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (930)..(930)
<223> OTHER INFORMATION: The 'Xaa' at location 930 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (931)..(931)
<223> OTHER INFORMATION: The 'Xaa' at location 931 stands for Lys, Asn, Arg, Ser, Thr, Ile, Met, Glu, Asp, Gly, Ala, Val, Gln, His, Pro, -continued

```
      Leu, a stop codon, Tyr, Trp, Cys, or Phe.
<221> NAME/KEY: misc_feature
<222> LOCATION: (932)..(932)
<223> OTHER INFORMATION: The 'Xaa' at location 932 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (933)..(933)
<223> OTHER INFORMATION: The 'Xaa' at location 933 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (934)..(934)
<223> OTHER INFORMATION: The 'Xaa' at location 934 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (935)..(935)
<223> OTHER INFORMATION: The 'Xaa' at location 935 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (936)..(936)
<223> OTHER INFORMATION: The 'Xaa' at location 936 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (937)..(937)
<223> OTHER INFORMATION: The 'Xaa' at location 937 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (938)..(938)
<223> OTHER INFORMATION: The 'Xaa' at location 938 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (939)..(939)
<223> OTHER INFORMATION: The 'Xaa' at location 939 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (940)..(940)
<223> OTHER INFORMATION: The 'Xaa' at location 940 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (941)..(941)
<223> OTHER INFORMATION: The 'Xaa' at location 941 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (942)..(942)
<223> OTHER INFORMATION: The 'Xaa' at location 942 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (943)..(943)
<223> OTHER INFORMATION: The 'Xaa' at location 943 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (944)..(944)
<223> OTHER INFORMATION: The 'Xaa' at location 944 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (945)..(945)
<223> OTHER INFORMATION: The 'Xaa' at location 945 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (946)..(946)
<223> OTHER INFORMATION: The 'Xaa' at location 946 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (947)..(947)
<223> OTHER INFORMATION: The 'Xaa' at location 947 stands for Lys, Asn,
```

-continued

Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (948)..(948)
<223> OTHER INFORMATION: The 'Xaa' at location 948 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (949)..(949)
<223> OTHER INFORMATION: The 'Xaa' at location 949 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (950)..(950)
<223> OTHER INFORMATION: The 'Xaa' at location 950 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (951)..(951)
<223> OTHER INFORMATION: The 'Xaa' at location 951 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (952)..(952)
<223> OTHER INFORMATION: The 'Xaa' at location 952 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (953)..(953)
<223> OTHER INFORMATION: The 'Xaa' at location 953 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (954)..(954)
<223> OTHER INFORMATION: The 'Xaa' at location 954 stands for
Met, Val, or Leu.
<221> NAME/KEY: misc_feature
<222> LOCATION: (1055)..(1055)
<223> OTHER INFORMATION: The 'Xaa' at location 1055 stands for Lys, Glu,
Gln, or a stop codon.
<221> NAME/KEY: misc_feature
<222> LOCATION: (1076)..(1076)
<223> OTHER INFORMATION: The 'Xaa' at location 1076 stands for Gly.
<221> NAME/KEY: misc_feature
<222> LOCATION: (1163)..(1163)
<223> OTHER INFORMATION: The 'Xaa' at location 1163 stands for Lys, Asn
Arg, Ser, Thr, Ile, or Met.
<221> NAME/KEY: misc_feature
<222> LOCATION: (1164)..(1164)
<223> OTHER INFORMATION: The 'Xaa' at location 1164 stands for Lys, Asn,
Arg, Ser, Thr, Ile, Met, Glu, Asp, Gly, Ala, Val, Gln, His, Pro
Leu, a stop codon, Tyr, Trp, Cys, or Phe.
<221> NAME/KEY: misc_feature
<222> LOCATION: (1165)..(1165)
<223> OTHER INFORMATION: The 'Xaa' at location 1165 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (1166)..(1166)
<223> OTHER INFORMATION: The 'Xaa' at location 1166 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (1167)..(1167)
<223> OTHER INFORMATION: The 'Xaa' at location 1167 stands for Arg, Gly,
or a stop codon.
<221> NAME/KEY: misc_feature
<222> LOCATION: (1)..(586)
<223> OTHER INFORMATION: Sequences not determined at this position .
Unknown residue put in to provide alignment.
<221> NAME/KEY: misc_feature
<222> LOCATION: (596)..(597)
<223> OTHER INFORMATION: Sequences not determined at this position .
Unknown residue put in to provide alignment.
<221> NAME/KEY: misc_feature
<222> LOCATION: (621)..(621)
<223> OTHER INFORMATION: Sequences not determined at this position .
Unknown residue put in to provide alignment.
<221> NAME/KEY: misc_feature -continued

```
<222> LOCATION: (626)..(626)
<223> OTHER INFORMATION: Sequences not determined at this position .
      Unknown residue put in to provide alignment.
<221> NAME/KEY: misc_feature
<222> LOCATION: (629)..(629)
<223> OTHER INFORMATION: Sequences not determined at this position .
      Unknown residue put in to provide alignment.
<221> NAME/KEY: misc_feature
<222> LOCATION: (638)..(638)
<223> OTHER INFORMATION: Sequences not determined at this position .
      Unknown residue put in to provide alignment.
<221> NAME/KEY: misc_feature
<222> LOCATION: (693)..(694)
<223> OTHER INFORMATION: Sequences not determined at this position .
      Unknown residue put in to provide alignment.
<221> NAME/KEY: misc_feature
<222> LOCATION: (724)..(724)
<223> OTHER INFORMATION: Sequences not determined at this position .
      Unknown residue put in to provide alignment.
<221> NAME/KEY: misc_feature
<222> LOCATION: (730)..(730)
<223> OTHER INFORMATION: Sequences not determined at this position .
      Unknown residue put in to provide alignment.
<221> NAME/KEY: misc_feature
<222> LOCATION: (764)..(764)
<223> OTHER INFORMATION: Sequences not determined at this position .
      Unknown residue put in to provide alignment.
<221> NAME/KEY: misc_feature
<222> LOCATION: (791)..(791)
<223> OTHER INFORMATION: Sequences not determined at this position .
      Unknown residue put in to provide alignment.
<221> NAME/KEY: misc_feature
<222> LOCATION: (2148)..(2148)
<223> OTHER INFORMATION: Sequences not determined at this position .
      Unknown residue put in to provide alignment.
<221> NAME/KEY: misc_feature
<222> LOCATION: (2177)..(2177)
<223> OTHER INFORMATION: Sequences not determined at this position .
      Unknown residue put in to provide alignment.
<221> NAME/KEY: misc_feature
<222> LOCATION: (2382)..(2382)
<223> OTHER INFORMATION: Sequences not determined at this position .
      Unknown residue put in to provide alignment.
<221> NAME/KEY: misc_feature
<222> LOCATION: (2398)..(2398)
<223> OTHER INFORMATION: Sequences not determined at this position .
      Unknown residue put in to provide alignment.
<221> NAME/KEY: misc_feature
<222> LOCATION: (2466)..(2466)
<223> OTHER INFORMATION: Sequences not determined at this position .
      Unknown residue put in to provide alignment.
<221> NAME/KEY: misc_feature
<222> LOCATION: (2468)..(2468)
<223> OTHER INFORMATION: Sequences not determined at this position .
      Unknown residue put in to provide alignment.
<221> NAME/KEY: misc_feature
<222> LOCATION: (2493)..(2493)
<223> OTHER INFORMATION: Sequences not determined at this position .
      Unknown residue put in to provide alignment.
<221> NAME/KEY: misc_feature
<222> LOCATION: (2536)..(2860)
<223> OTHER INFORMATION: Sequences not determined at this position .
      Unknown residue put in to provide alignment.
<221> NAME/KEY: misc_feature
<222> LOCATION: (3163)..(3163)
<223> OTHER INFORMATION: Sequences not determined at this position .
      Unknown residue put in to provide alignment.
<221> NAME/KEY: misc_feature
<222> LOCATION: (3488)..(3499)
<223> OTHER INFORMATION: Sequences not determined at this position .
      Unknown residue put in to provide alignment.

<400> SEQUENCE: 2

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30
```

-continued

```
Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Pro Phe Xaa Arg Leu Val Thr Pro Glu Lys Val Asn
        195                 200                 205

Xaa Xaa Asn Thr Xaa Gly Arg Lys Ser Thr Pro Leu His Phe Pro Ala
    210                 215                 220

Gly Phe Gly Arg Lys Asn Xaa Xaa Lys Tyr Leu Leu Gln Asn Gly Ala
225                 230                 235                 240

Asn Xaa Gln Xaa Leu Tyr Asn Gly Gly Leu Ile Pro Leu His Xaa Ala
                245                 250                 255

Cys Ser Phe Gly His Ala Lys Xaa Ile Asn Leu Leu Leu Arg His Gly
            260                 265                 270

Ala Asp Pro Asn Ala Arg Asp Asn Trp Asn Tyr Thr Pro Leu His Glu
        275                 280                 285

Ala Ala Ile Lys Gly Lys Ile Asp Val Cys Ile Val Leu Leu Gln His
    290                 295                 300

Gly Ala Glu Pro Thr Ile Arg Asn Thr Asp Gly Arg Thr Ala Leu Asp
305                 310                 315                 320

Leu Ala Asp Pro Ser Ala Lys Ala Val Leu Thr Gly Glu Tyr Lys Lys
                325                 330                 335

Asp Glu Leu Leu Glu Ser Ala Arg Ser Gly Asn Glu Glu Lys Met Met
            340                 345                 350

Ala Leu Leu Thr Pro Leu Asn Val Asn Cys His Ala Ser Asp Gly Arg
        355                 360                 365

Lys Ser Thr Pro Leu His Leu Ala Ala Gly Tyr Asn Arg Val Lys Ile
    370                 375                 380

Val Gln Leu Leu Leu Gln His Gly Ala Asp Val His Ala Lys Asp Lys
385                 390                 395                 400

Gly Asp Leu Val Pro Leu His Asn Ala Cys Ser Tyr Gly His Tyr Glu
                405                 410                 415

Val Thr Glu Leu Leu Val Lys His Gly Ala Cys Val Asn Ala Met Asp
            420                 425                 430

Leu Trp Gln Phe Thr Pro Leu His Glu Ala Ala Ser Lys Asn Arg Val
        435                 440                 445
```

-continued

```
Glu Val Cys Ser Leu Leu Leu Ser Tyr Gly Ala Asp Pro Thr Leu Leu
    450                 455                 460

Asn Cys His Asn Lys Ser Ala Ile Asp Leu Ala Pro Thr Pro Gln Leu
465                 470                 475                 480

Lys Glu Arg Leu Ala Tyr Glu Phe Lys Gly His Ser Leu Leu Gln Ala
                485                 490                 495

Ala Arg Glu Ala Asp Val Thr Arg Ile Lys Lys His Leu Ser Leu Glu
            500                 505                 510

Met Val Asn Phe Lys His Pro Gln Thr His Glu Thr Ala Leu His Cys
        515                 520                 525

Ala Ala Ala Ser Pro Tyr Pro Lys Arg Lys Gln Ile Cys Glu Leu Leu
    530                 535                 540

Leu Arg Lys Gly Ala Asn Ile Asn Glu Lys Thr Lys Glu Phe Leu Thr
545                 550                 555                 560

Pro Leu His Val Ala Ser Glu Lys Ala His Asn Asp Val Val Glu Val
                565                 570                 575

Val Val Lys His Glu Ala Lys Val Asn Ala Leu Asp Asn Leu Gly Gln
            580                 585                 590

Thr Ser Leu His Arg Ala Ala Tyr Cys Gly His Leu Gln Thr Cys Arg
        595                 600                 605

Leu Leu Leu Ser Tyr Gly Cys Asp Pro Asn Ile Ile Ser Leu Gln Gly
    610                 615                 620

Phe Thr Ala Leu Gln Met Gly Asn Glu Asn Val Gln Gln Leu Leu Gln
625                 630                 635                 640

Glu Gly Ile Ser Leu Gly Asn Ser Glu Ala Asp Arg Gln Leu Leu Glu
                645                 650                 655

Ala Ala Lys Ala Gly Asp Val Glu Thr Val Lys Lys Leu Cys Thr Val
            660                 665                 670

Gln Ser Val Asn Cys Arg Asp Ile Glu Gly Arg Gln Ser Thr Pro Leu
        675                 680                 685

His Phe Ala Ala Gly Tyr Asn Arg Val Ser Val Val Glu Tyr Leu Leu
    690                 695                 700

Gln His Gly Ala Asp Val His Ala Lys Asp Lys Gly Gly Leu Val Pro
705                 710                 715                 720

Leu His Asn Ala Cys Xaa Tyr Gly His Tyr Glu Val Ala Glu Leu Leu
                725                 730                 735

Val Lys His Gly Ala Val Val Asn Val Ala Asp Leu Trp Lys Phe Thr
            740                 745                 750

Pro Leu His Glu Ala Ala Ala Lys Gly Lys Tyr Glu Ile Cys Lys Leu
        755                 760                 765

Leu Leu Gln His Gly Ala Asp Pro Thr Lys Lys Asn Arg Asp Gly Asn
    770                 775                 780

Thr Leu Leu Asp Leu Val Lys Asp Gly Xaa Thr Asp Ile Gln Asp Xaa
785                 790                 795                 800

Leu Arg Gly Asp Ala Val Leu Leu Asp Ala Ala Lys Lys Gly Cys Leu
                805                 810                 815

Ala Arg Val Lys Lys Xaa Xaa Phe Pro Asp Asn Val Asn Cys Arg Asp
            820                 825                 830

Thr Gln Gly Arg His Ser Thr Pro Leu His Leu Ala Gly Xaa Xaa Xaa
        835                 840                 845

Xaa Xaa Xaa Xaa Xaa Xaa Xaa Xaa Xaa Xaa Xaa Xaa Xaa Xaa Xaa Xaa
    850                 855                 860

Xaa Xaa Xaa Xaa Xaa Xaa Xaa Xaa Xaa Xaa Xaa Xaa Xaa Xaa Xaa Xaa
```

-continued

```
865                 870                 875                 880

Xaa Xaa Xaa Xaa Xaa Xaa Xaa Xaa Xaa Xaa Xaa Xaa Xaa Xaa Xaa Xaa
                885                 890                 895

Xaa Xaa Xaa Xaa Xaa Xaa Xaa Xaa Xaa Xaa Xaa Xaa Xaa Xaa Xaa Xaa
            900                 905                 910

Xaa Xaa Xaa Xaa Xaa Xaa Xaa Xaa Xaa Xaa Xaa Xaa Xaa Xaa Xaa Xaa
        915                 920                 925

Xaa Xaa Xaa Xaa Xaa Xaa Xaa Xaa Xaa Xaa Xaa Xaa Xaa Xaa Xaa Xaa
    930                 935                 940

Xaa Xaa Xaa Xaa Xaa Xaa Xaa Xaa Xaa Xaa Thr Ala Ala Met Pro Pro
945                 950                 955                 960

Ser Val Leu Pro Ser Cys Asn Lys Pro Gln Val Leu Asn Gly Val Arg
                965                 970                 975

Ser Pro Gly Ala Thr Ala Asp Ala Leu Ser Ser Gly Pro Ser Ser Pro
            980                 985                 990

Ser Ser Leu Ser Ala Ala Ser Ser  Leu Asp Asn Leu Ser  Gly Ser Phe
        995                 1000                1005

Ser Glu  Leu Ser Ser Val Val  Ser Ser Ser Gly Thr  Glu Gly Ala
    1010                1015                1020

Ser Ser  Leu Glu Lys Lys Glu  Val Pro Gly Val Asp  Phe Ser Ile
    1025                1030                1035

Thr Gln  Phe Val Arg Asn Leu  Gly Leu Glu His Leu  Met Asp Ile
    1040                1045                1050

Phe Xaa  Arg Glu Gln Ile Thr  Leu Asp Val Leu Val  Glu Met Gly
    1055                1060                1065

His Lys  Glu Leu Lys Glu Ile  Xaa Ile Asn Ala Tyr  Gly His Arg
    1070                1075                1080

His Lys  Leu Ile Lys Gly Val  Glu Arg Leu Ile Ser  Gly Gln Gln
    1085                1090                1095

Gly Leu  Asn Pro Tyr Leu Thr  Leu Asn Thr Ser Gly  Ser Gly Thr
    1100                1105                1110

Ile Leu  Ile Asp Leu Ser Pro  Asp Asp Lys Glu Phe  Gln Ser Val
    1115                1120                1125

Glu Glu  Glu Met Gln Ser Thr  Val Arg Glu His Arg  Asp Gly Gly
    1130                1135                1140

His Ala  Gly Gly Ile Phe Asn  Arg Tyr Asn Ile Leu  Lys Ile Gln
    1145                1150                1155

Lys Val  Cys Asn Xaa Xaa Xaa  Xaa Xaa Ala Lys Ile  Arg His Glu
    1160                1165                1170

Glu Arg  Tyr Thr His Arg Arg  Lys Glu Val Ser Glu  Glu Asn His
    1175                1180                1185

Asn His  Ala Asn Glu Arg Met  Leu Phe His Gly Ser  Pro Phe Val
    1190                1195                1200

Asn Ala  Ile Ile His Lys Gly  Phe Asp Glu Arg His  Ala Tyr Ile
    1205                1210                1215

Gly Gly  Met Phe Gly Ala Gly  Ile Tyr Phe Ala Glu  Asn Ser Ser
    1220                1225                1230

Lys Ser  Asn Gln Tyr Val Tyr  Gly Ile Gly Gly Gly  Thr Gly Cys
    1235                1240                1245

Pro Val  His Lys Asp Arg Ser  Cys Tyr Ile Cys His  Arg Gln Leu
    1250                1255                1260

Leu Phe  Cys Arg Val Thr Leu  Gly Lys Ser Phe Leu  Gln Phe Ser
    1265                1270                1275
```

-continued

```
Ala Met  Lys Met Ala His Ser  Pro Pro Gly His His  Ser Val Thr
    1280                 1285                 1290

Gly Arg  Pro Ser Val Asn Gly  Leu Ala Leu Ala Glu  Tyr Val Ile
    1295                 1300                 1305

Tyr Arg  Gly Glu Gln Ala Tyr  Pro Glu Tyr Leu Ile  Thr Tyr Gln
    1310                 1315                 1320

Ile Met  Arg Pro Glu Gly Met  Val Asp Gly
    1325                 1330


<210> SEQ ID NO 3
<211> LENGTH: 4297
<212> TYPE: DNA
<213> ORGANISM: Homo sapiens
<220> FEATURE:
<221> NAME/KEY: CDS
<222> LOCATION: (1)..(3801)
<223> OTHER INFORMATION:
<221> NAME/KEY: misc_feature
<222> LOCATION: (1)..(1)
<223> OTHER INFORMATION: Sequences not determined at this position .
      Unknown residue put in to provide alignment.
<221> NAME/KEY: misc_feature
<222> LOCATION: (125)..(125)
<223> OTHER INFORMATION: Sequences not determined at this position .
      Unknown residue put in to provide alignment.
<221> NAME/KEY: misc_feature
<222> LOCATION: (293)..(293)
<223> OTHER INFORMATION: Sequences not determined at this position .
      Unknown residue put in to provide alignment.
<221> NAME/KEY: misc_feature
<222> LOCATION: (328)..(328)
<223> OTHER INFORMATION: Sequences not determined at this position .
      Unknown residue put in to provide alignment.
<221> NAME/KEY: misc_feature
<222> LOCATION: (341)..(341)
<223> OTHER INFORMATION: Sequences not determined at this position .
      Unknown residue put in to provide alignment.
<221> NAME/KEY: misc_feature
<222> LOCATION: (378)..(378)
<223> OTHER INFORMATION: Sequences not determined at this position .
      Unknown residue put in to provide alignment.
<221> NAME/KEY: misc_feature
<222> LOCATION: (415)..(415)
<223> OTHER INFORMATION: Sequences not determined at this position .
      Unknown residue put in to provide alignment.
<221> NAME/KEY: misc_feature
<222> LOCATION: (432)..(432)
<223> OTHER INFORMATION: Sequences not determined at this position .
      Unknown residue put in to provide alignment.
<221> NAME/KEY: misc_feature
<222> LOCATION: (459)..(459)
<223> OTHER INFORMATION: Sequences not determined at this position .
      Unknown residue put in to provide alignment.
<221> NAME/KEY: misc_feature
<222> LOCATION: (496)..(496)
<223> OTHER INFORMATION: Sequences not determined at this position .
      Unknown residue put in to provide alignment.
<221> NAME/KEY: misc_feature
<222> LOCATION: (517)..(517)
<223> OTHER INFORMATION: Sequences not determined at this position .
      Unknown residue put in to provide alignment.
<221> NAME/KEY: misc_feature
<222> LOCATION: (534)..(534)
<223> OTHER INFORMATION: Sequences not determined at this position .
      Unknown residue put in to provide alignment.
<221> NAME/KEY: misc_feature
<222> LOCATION: (553)..(553)
<223> OTHER INFORMATION: Sequences not determined at this position .
      Unknown residue put in to provide alignment.
<221> NAME/KEY: misc_feature
<222> LOCATION: (562)..(562)
<223> OTHER INFORMATION: Sequences not determined at this position .
      Unknown residue put in to provide alignment.
<221> NAME/KEY: misc_feature
```

-continued

<222> LOCATION: (614)..(614)
<223> OTHER INFORMATION: Sequences not determined at this position . Unknown residue put in to provide alignment.
<221> NAME/KEY: misc_feature
<222> LOCATION: (619)..(619)
<223> OTHER INFORMATION: Sequences not determined at this position . Unknown residue put in to provide alignment.
<221> NAME/KEY: misc_feature
<222> LOCATION: (632)..(632)
<223> OTHER INFORMATION: Sequences not determined at this position . Unknown residue put in to provide alignment.
<221> NAME/KEY: misc_feature
<222> LOCATION: (637)..(637)
<223> OTHER INFORMATION: Sequences not determined at this position . Unknown residue put in to provide alignment.
<221> NAME/KEY: misc_feature
<222> LOCATION: (643)..(643)
<223> OTHER INFORMATION: Sequences not determined at this position . Unknown residue put in to provide alignment.
<221> NAME/KEY: misc_feature
<222> LOCATION: (680)..(680)
<223> OTHER INFORMATION: Sequences not determined at this position . Unknown residue put in to provide alignment.
<221> NAME/KEY: misc_feature
<222> LOCATION: (682)..(682)
<223> OTHER INFORMATION: Sequences not determined at this position . Unknown residue put in to provide alignment.
<221> NAME/KEY: misc_feature
<222> LOCATION: (711)..(713)
<223> OTHER INFORMATION: Sequences not determined at this position . Unknown residue put in to provide alignment.
<221> NAME/KEY: misc_feature
<222> LOCATION: (1971)..(1971)
<223> OTHER INFORMATION: Sequences not determined at this position . Unknown residue put in to provide alignment.
<221> NAME/KEY: misc_feature
<222> LOCATION: (2000)..(2000)
<223> OTHER INFORMATION: Sequences not determined at this position . Unknown residue put in to provide alignment.
<221> NAME/KEY: misc_feature
<222> LOCATION: (2175)..(2175)
<223> OTHER INFORMATION: Sequences not determined at this position . Unknown residue put in to provide alignment.
<221> NAME/KEY: misc_feature
<222> LOCATION: (2180)..(2180)
<223> OTHER INFORMATION: Sequences not determined at this position . Unknown residue put in to provide alignment.
<221> NAME/KEY: misc_feature
<222> LOCATION: (2205)..(2205)
<223> OTHER INFORMATION: Sequences not determined at this position . Unknown residue put in to provide alignment.
<221> NAME/KEY: misc_feature
<222> LOCATION: (2221)..(2221)
<223> OTHER INFORMATION: Sequences not determined at this position . Unknown residue put in to provide alignment.
<221> NAME/KEY: misc_feature
<222> LOCATION: (2289)..(2289)
<223> OTHER INFORMATION: Sequences not determined at this position . Unknown residue put in to provide alignment.
<221> NAME/KEY: misc_feature
<222> LOCATION: (2316)..(2316)
<223> OTHER INFORMATION: Sequences not determined at this position . Unknown residue put in to provide alignment.
<221> NAME/KEY: misc_feature
<222> LOCATION: (2359)..(2674)
<223> OTHER INFORMATION: Sequences not determined at this position . Unknown residue put in to provide alignment.
<221> NAME/KEY: misc_feature
<222> LOCATION: (2977)..(2977)
<223> OTHER INFORMATION: Sequences not determined at this position . Unknown residue put in to provide alignment.
<221> NAME/KEY: misc_feature
<222> LOCATION: (2291)..(2291)
<223> OTHER INFORMATION: Sequences not determined at this position . Unknown residue put in to provide alignment.

<400> SEQUENCE: 3 ncc cac gcg tcc ggg cag gag ggg cct tgc cag ctt ccg ccg ccg cgt 48

-continued

```
Xaa His Ala Ser Gly Gln Glu Gly Pro Cys Gln Leu Pro Pro Pro Arg
1               5                   10                  15

cgt ttc agg acc cgg acg gcg gat tcg cgc tgc ctc cgc cgc cgc ggg       96
Arg Phe Arg Thr Arg Thr Ala Asp Ser Arg Cys Leu Arg Arg Arg Gly
            20                  25                  30

gca gcc ggg ggg cag gga gcc cat cga ang ggc gcg cgt ggg cgc ggc      144
Ala Ala Gly Gly Gln Gly Ala His Arg Xaa Gly Ala Arg Gly Arg Gly
        35                  40                  45

cat ggg act gcg ccg gat ccg gtg aca gca ggg agc caa gcg gcc cgg      192
His Gly Thr Ala Pro Asp Pro Val Thr Ala Gly Ser Gln Ala Ala Arg
    50                  55                  60

gcc ctg agc gcg tct tct ccg ggg ggc ctc gcc ctc ctg ctc gcg ggg      240
Ala Leu Ser Ala Ser Ser Pro Gly Gly Leu Ala Leu Leu Leu Ala Gly
65                  70                  75                  80

ccg ggg ctc ctg ctc cgg ttg ctg gcg ctg ttg ctg gct gtg gcg gcg      288
Pro Gly Leu Leu Leu Arg Leu Leu Ala Leu Leu Leu Ala Val Ala Ala
                85                  90                  95

gcc ang atc atg tcg ggt cgc cgc tgc gcc ggc ggg gga ncg gcc tgc      336
Ala Xaa Ile Met Ser Gly Arg Arg Cys Ala Gly Gly Gly Xaa Ala Cys
            100                 105                 110

gcg anc gcc gcg gcc gaa gcc gtg gaa ccg gcc gcc cga aan ctg ttc      384
Ala Xaa Ala Ala Ala Glu Ala Val Glu Pro Ala Ala Arg Xaa Leu Phe
        115                 120                 125

gaa gcg tgc cgc aac ggg gac gtg gaa cga ntc aag aag ctg gtg acn      432
Glu Ala Cys Arg Asn Gly Asp Val Glu Arg Xaa Lys Lys Leu Val Xaa
    130                 135                 140

cct gar aag gtg aac agc cgc gac acn gcg ggc agg aaa tcc acc ccg      480
Pro Glu Lys Val Asn Ser Arg Asp Xaa Ala Gly Arg Lys Ser Thr Pro
145                 150                 155                 160

ctg cac tty ccc gca ngt ttt ggg cgg aaa gac tta ntt raa tat ttg      528
Leu His Phe Pro Ala Xaa Phe Gly Arg Lys Asp Leu Xaa Xaa Tyr Leu
                165                 170                 175

ctt can aat ggt gca aat gty caa nca cgt gat nat ggg ggc ctt att      576
Leu Thr Asn Gly Ala Asn Xaa Gln Xaa Arg Asp Xaa Gly Gly Leu Ile
            180                 185                 190

cct ctt cat aat gca tgc tct ttt ggt cmt gct raa ant atc nat ctc      624
Pro Leu His Asn Ala Cys Ser Phe Gly Xaa Ala Xaa Xaa Ile Xaa Leu
        195                 200                 205

ctt ttg cna cat ngt gca nam ccc aat gct cga gat aat tgg aat tat      672
Leu Leu Xaa His Xaa Ala Xaa Pro Asn Ala Arg Asp Asn Trp Asn Tyr
    210                 215                 220

act cct cnc nat gaa gct gca att aaa gga aag att gan nnt tgc att      720
Thr Pro Xaa Xaa Glu Ala Ala Ile Lys Gly Lys Ile Xaa Xaa Cys Ile
225                 230                 235                 240

gtg ctg tta cag cat gga gct gag cca acc atc cga aat aca gat gga      768
Val Leu Leu Gln His Gly Ala Glu Pro Thr Ile Arg Asn Thr Asp Gly
                245                 250                 255

agg aca gca ttg gat tta gca gat cca tct gcc aaa gca gtg ctt act      816
Arg Thr Ala Leu Asp Leu Ala Asp Pro Ser Ala Lys Ala Val Leu Thr
            260                 265                 270

ggt gaa tat aag aaa gat gaa ctc tta gaa agt gcc agg agt ggc aat      864
Gly Glu Tyr Lys Lys Asp Glu Leu Leu Glu Ser Ala Arg Ser Gly Asn
        275                 280                 285

gaa gaa aaa atg atg gct cta ctc aca cca tta aat gtc aac tgc cac      912
Glu Glu Lys Met Met Ala Leu Leu Thr Pro Leu Asn Val Asn Cys His
    290                 295                 300

gca agt gat ggc aga aag tca act cca tta cat ttg gca gca gga tat      960
Ala Ser Asp Gly Arg Lys Ser Thr Pro Leu His Leu Ala Ala Gly Tyr
305                 310                 315                 320
```

-continued

```
aac aga gta aag att gta cag ctg tta ctg caa cat gga gct gat gtc      1008
Asn Arg Val Lys Ile Val Gln Leu Leu Leu Gln His Gly Ala Asp Val
            325                 330                 335

cat gct aaa gat aaa ggt gat ctg gta cca tta cac aat gcc tgt tct      1056
His Ala Lys Asp Lys Gly Asp Leu Val Pro Leu His Asn Ala Cys Ser
            340                 345                 350

tat ggt cat tat gaa gta act gaa ctt ttg gtc aag cat ggt gcc tgt      1104
Tyr Gly His Tyr Glu Val Thr Glu Leu Leu Val Lys His Gly Ala Cys
        355                 360                 365

gta aat gca atg gac ttg tgg caa ttc act cct ctt cat gag gca gct      1152
Val Asn Ala Met Asp Leu Trp Gln Phe Thr Pro Leu His Glu Ala Ala
    370                 375                 380

tct aag aac agg gtt gaa gta tgt tct ctt ctc tta agt tat ggt gca      1200
Ser Lys Asn Arg Val Glu Val Cys Ser Leu Leu Leu Ser Tyr Gly Ala
385                 390                 395                 400

gac cca aca ctg ctc aat tgt cac aat aaa agt gct ata gac ttg gct      1248
Asp Pro Thr Leu Leu Asn Cys His Asn Lys Ser Ala Ile Asp Leu Ala
            405                 410                 415

ccc aca cca cag tta aaa gaa aga tta gca tat gaa ttt aaa ggc cac      1296
Pro Thr Pro Gln Leu Lys Glu Arg Leu Ala Tyr Glu Phe Lys Gly His
            420                 425                 430

tcg ttg ctg caa gct gca cga gaa gct gat gtt act cga atc aaa aaa      1344
Ser Leu Leu Gln Ala Ala Arg Glu Ala Asp Val Thr Arg Ile Lys Lys
        435                 440                 445

cat ctc tct ctg gaa atg gtg aat ttc aag cat cct caa aca cat gaa      1392
His Leu Ser Leu Glu Met Val Asn Phe Lys His Pro Gln Thr His Glu
    450                 455                 460

aca gca ttg cat tgt gct gct gca tct cca tat ccc aaa aga aag caa      1440
Thr Ala Leu His Cys Ala Ala Ala Ser Pro Tyr Pro Lys Arg Lys Gln
465                 470                 475                 480

ata tgt gaa ctg ttg cta aga aaa gga gca aac atc aat gaa aag act      1488
Ile Cys Glu Leu Leu Leu Arg Lys Gly Ala Asn Ile Asn Glu Lys Thr
            485                 490                 495

aaa gaa ttc ttg act cct ctg cac gtg gca tct gag aaa gct cat aat      1536
Lys Glu Phe Leu Thr Pro Leu His Val Ala Ser Glu Lys Ala His Asn
            500                 505                 510

gat gtt gtt gaa gta gtg gtg aaa cat gaa gca aag gtt aat gct ctg      1584
Asp Val Val Glu Val Val Val Lys His Glu Ala Lys Val Asn Ala Leu
        515                 520                 525

gat aat ctt ggt cag act tct cta cac aga gct gca tat tgt ggt cat      1632
Asp Asn Leu Gly Gln Thr Ser Leu His Arg Ala Ala Tyr Cys Gly His
    530                 535                 540

cta caa acc tgc cgc cta ctc ctg agc tat ggg tgt gat cct aac att      1680
Leu Gln Thr Cys Arg Leu Leu Leu Ser Tyr Gly Cys Asp Pro Asn Ile
545                 550                 555                 560

ata tcc ctt cag ggc ttt act gct tta cag atg gga aat gaa aat gta      1728
Ile Ser Leu Gln Gly Phe Thr Ala Leu Gln Met Gly Asn Glu Asn Val
            565                 570                 575

cag caa ctc ctc caa gag ggt atc tca tta ggt aat tca gag gca gac      1776
Gln Gln Leu Leu Gln Glu Gly Ile Ser Leu Gly Asn Ser Glu Ala Asp
            580                 585                 590

aga caa ttg ctg gaa gct gca aag gct gga gat gtc gaa act gta aaa      1824
Arg Gln Leu Leu Glu Ala Ala Lys Ala Gly Asp Val Glu Thr Val Lys
        595                 600                 605

aaa ctg tgt act gtt cag agt gtc aac tgc aga gac att gaa ggg cgt      1872
Lys Leu Cys Thr Val Gln Ser Val Asn Cys Arg Asp Ile Glu Gly Arg
    610                 615                 620

cag tct aca cca ctt cat ttt gca gct ggg tat aac aga gtg tcc gtg      1920
Gln Ser Thr Pro Leu His Phe Ala Ala Gly Tyr Asn Arg Val Ser Val
625                 630                 635                 640
```

-continued

```
gtg gaa tat ctg cta cag cat gga gct gat gtg cat gct aaa gat aaa     1968
Val Glu Tyr Leu Leu Gln His Gly Ala Asp Val His Ala Lys Asp Lys
                645                 650                 655

ggn ggc ctt gta cct ttg cac aat gca tgt tnt tat gga cat tat gaa     2016
Gly Gly Leu Val Pro Leu His Asn Ala Cys Xaa Tyr Gly His Tyr Glu
            660                 665                 670

gtt gca gaa ctt ctt gtt aaa cat gga gca gta gtt aat gta gct gat     2064
Val Ala Glu Leu Leu Val Lys His Gly Ala Val Val Asn Val Ala Asp
        675                 680                 685

tta tgg aaa ttt aca cct tta cat gaa gca gca gca aaa gga aaa tat     2112
Leu Trp Lys Phe Thr Pro Leu His Glu Ala Ala Ala Lys Gly Lys Tyr
    690                 695                 700

gaa att tgc aaa ctt ctg ctc cag cat ggt gca gac cct aca aaa aaa     2160
Glu Ile Cys Lys Leu Leu Leu Gln His Gly Ala Asp Pro Thr Lys Lys
705                 710                 715                 720

aaa aaa aaa gga aan att cnt ttg gat ctt gtt aaa gat gga gan aca     2208
Lys Lys Lys Gly Xaa Ile Xaa Leu Asp Leu Val Lys Asp Gly Xaa Thr
                725                 730                 735

gat att caa gat ntg ctt agg gga gat gca gtt ttg tta gat gct gcc     2256
Asp Ile Gln Asp Xaa Leu Arg Gly Asp Ala Val Leu Leu Asp Ala Ala
            740                 745                 750

aag aag ggt tgt tta gcc aga gtg aag aag ttn tnt ttt cct gat aat     2304
Lys Lys Gly Cys Leu Ala Arg Val Lys Lys Xaa Xaa Phe Pro Asp Asn
        755                 760                 765

gta aat tgc cgn gat acc caa ggc aga cat tca aca cct tta cat tta     2352
Val Asn Cys Arg Asp Thr Gln Gly Arg His Ser Thr Pro Leu His Leu
    770                 775                 780

gca ggt nnn nnn nnn nnn nnn nnn nnn nnn nnn nnn nnn nnn nnn nnn     2400
Ala Gly Xaa Xaa Xaa Xaa Xaa Xaa Xaa Xaa Xaa Xaa Xaa Xaa Xaa Xaa
785                 790                 795                 800

nnn nnn nnn nnn nnn nnn nnn nnn nnn nnn nnn nnn nnn nnn nnn nnn     2448
Xaa Xaa Xaa Xaa Xaa Xaa Xaa Xaa Xaa Xaa Xaa Xaa Xaa Xaa Xaa Xaa
                805                 810                 815

nnn nnn nnn nnn nnn nnn nnn nnn nnn nnn nnn nnn nnn nnn nnn nnn     2496
Xaa Xaa Xaa Xaa Xaa Xaa Xaa Xaa Xaa Xaa Xaa Xaa Xaa Xaa Xaa Xaa
            820                 825                 830

nnn nnn nnn nnn nnn nnn nnn nnn nnn nnn nnn nnn nnn nnn nnn nnn     2544
Xaa Xaa Xaa Xaa Xaa Xaa Xaa Xaa Xaa Xaa Xaa Xaa Xaa Xaa Xaa Xaa
        835                 840                 845

nnn nnn nnn nnn nnn nnn nnn nnn nnn nnn nnn nnn nnn nnn nnn nnn     2592
Xaa Xaa Xaa Xaa Xaa Xaa Xaa Xaa Xaa Xaa Xaa Xaa Xaa Xaa Xaa Xaa
    850                 855                 860

nnn nnn nnn nnn nnn nnn nnn nnn nnn nnn nnn nnn nnn nnn nnn nnn     2640
Xaa Xaa Xaa Xaa Xaa Xaa Xaa Xaa Xaa Xaa Xaa Xaa Xaa Xaa Xaa Xaa
865                 870                 875                 880

nnn nnn nnn nnn nnn nnn nnn nnn nnn nnn nnn ntg aca gca gcc atg     2688
Xaa Xaa Xaa Xaa Xaa Xaa Xaa Xaa Xaa Xaa Xaa Xaa Thr Ala Ala Met
                885                 890                 895

ccc cca tct gtt ctg ccc tct tgt aac aag cct caa gtg ctc aat ggt     2736
Pro Pro Ser Val Leu Pro Ser Cys Asn Lys Pro Gln Val Leu Asn Gly
            900                 905                 910

gtg aga agc cca gga gcc act gca gat gct ctc tct tca ggt cca tct     2784
Val Arg Ser Pro Gly Ala Thr Ala Asp Ala Leu Ser Ser Gly Pro Ser
        915                 920                 925

agc cca tca agc ctt tct gca gcc agc agt ctt gac aac tta tct ggg     2832
Ser Pro Ser Ser Leu Ser Ala Ala Ser Ser Leu Asp Asn Leu Ser Gly
    930                 935                 940

agt ttt tca gaa ctg tct tca gta gtt agt tca agt gga aca gag ggt     2880
Ser Phe Ser Glu Leu Ser Ser Val Val Ser Ser Ser Gly Thr Glu Gly
```

-continued

```
945                 950                 955                 960

gct tcc agt ttg gag aaa aag gag gtt cca gga gta gat ttt agc ata     2928
Ala Ser Ser Leu Glu Lys Lys Glu Val Pro Gly Val Asp Phe Ser Ile
                965                 970                 975

act caa ttc gta agg aat ctt gga ctt gag cac cta atg gat ata ttt     2976
Thr Gln Phe Val Arg Asn Leu Gly Leu Glu His Leu Met Asp Ile Phe
            980                 985                 990

nag aga gaa cag atc act ttg gat  gta tta gtt gag atg  ggg cac aag   3024
Xaa Arg Glu Gln Ile Thr Leu Asp  Val Leu Val Glu Met  Gly His Lys
        995                 1000                1005

gag ctg  aag gag att ggw atc  aat gct tat gga cat  agg cac aaa     3069
Glu Leu  Lys Glu Ile Xaa Ile  Asn Ala Tyr Gly His  Arg His Lys
    1010                 1015                 1020

cta att  aaa agt ttc gag aga  ctt atc tcc gga caa  caa ggt ctt     3114
Leu Ile  Lys Ser Phe Glu Arg  Leu Ile Ser Gly Gln  Gln Gly Leu
    1025                 1030                 1035

aac cca  tat tta act ttg aac  acc tct ggt agt gga  aca att ctt     3159
Asn Pro  Tyr Leu Thr Leu Asn  Thr Ser Gly Ser Gly  Thr Ile Leu
    1040                 1045                 1050

ata gat  ctg tct cct gat gat  aaa gag ttt cag tct  gtg gag gaa     3204
Ile Asp  Leu Ser Pro Asp Asp  Lys Glu Phe Gln Ser  Val Glu Glu
    1055                 1060                 1065

gag atg  caa agt aca gtt cga  gag cac aga gat gga  ggt cat gca     3249
Glu Met  Gln Ser Thr Val Arg  Glu His Arg Asp Gly  Gly His Ala
    1070                 1075                 1080

ggt gga  atc ttc aac aga tac  aat att ctc aag att  cag aag gtt     3294
Gly Gly  Ile Phe Asn Arg Tyr  Asn Ile Leu Lys Ile  Gln Lys Val
    1085                 1090                 1095

tgt aac  aga gcc aag att cgg  cac gag gaa aga tac  act cac cgg     3339
Cys Asn  Arg Ala Lys Ile Arg  His Glu Glu Arg Tyr  Thr His Arg
    1100                 1105                 1110

aga aaa  gaa gtt tct gaa gaa  aac cac aac cat gcc  aat gaa cga     3384
Arg Lys  Glu Val Ser Glu Glu  Asn His Asn His Ala  Asn Glu Arg
    1115                 1120                 1125

atg cta  ttt cat ggg tct cct  ttt gtg aat gca att  atc cac aaa     3429
Met Leu  Phe His Gly Ser Pro  Phe Val Asn Ala Ile  Ile His Lys
    1130                 1135                 1140

ggc ttt  gat gaa agg cat gcg  tac ata ggt ggt atg  ttt gga gct     3474
Gly Phe  Asp Glu Arg His Ala  Tyr Ile Gly Gly Met  Phe Gly Ala
    1145                 1150                 1155

ggc att  tat ttt gct gaa aac  tct tcc aaa agc aat  caa tat gta     3519
Gly Ile  Tyr Phe Ala Glu Asn  Ser Ser Lys Ser Asn  Gln Tyr Val
    1160                 1165                 1170

tat gga  att gga gga ggt act  ggg tgt cca gtt cac  aaa gac aga     3564
Tyr Gly  Ile Gly Gly Gly Thr  Gly Cys Pro Val His  Lys Asp Arg
    1175                 1180                 1185

tct tgt  tac att tgc cac agg  cag ctg ctc ttt tgc  cgg gta acc     3609
Ser Cys  Tyr Ile Cys His Arg  Gln Leu Leu Phe Cys  Arg Val Thr
    1190                 1195                 1200

ttg gga  aag tct ttc ctg cag  ttc agt gca atg aaa  atg gca cat     3654
Leu Gly  Lys Ser Phe Leu Gln  Phe Ser Ala Met Lys  Met Ala His
    1205                 1210                 1215

tct cct  cca ggt cat cac tca  gtc act ggt agg ccc  agt gta aat     3699
Ser Pro  Pro Gly His His Ser  Val Thr Gly Arg Pro  Ser Val Asn
    1220                 1225                 1230

ggc cta  gca tta gct gaa tat  gtt att tac aga gga  gaa cag gct     3744
Gly Leu  Ala Leu Ala Glu Tyr  Val Ile Tyr Arg Gly  Glu Gln Ala
    1235                 1240                 1245

tat cct  gag tat tta att act  tac cag att atg agg  cct gaa ggt     3789
```

-continued

```
Tyr Pro  Glu Tyr Leu Ile Thr  Tyr Gln Ile Met Arg  Pro Glu Gly
    1250                 1255                 1260

atg gtc  gat gga taaatagtta ttttaagaaa ctaattccac tgaacctaaa        3841
Met Val  Asp Gly
    1265

atcatcaaag cagcagtggc ctctacgttt tactcctttg ctgaaaaaaa atcatcttgc   3901

ccacaggcct gtggcaaaag gataaaaatg tgaacgaagt ttaacattct gacttgataa   3961

agctttaata atgtacagtg ttttctaaat atttcctgtt ttttcagcac tttaacagat   4021

gccattccag gttaaactgg gttgtctgta ctaaattata aacagagtta acttgaacct   4081

tttatatgtt atgcattgat tctaacaaac tgtaatgccc tcaacagaac taattttact   4141

aatacaatac tgtgttcttt aaaacacagc atttacactg aatacaattt catttgtaaa   4201

actgtaaata agagcttttg tactagccca gtatttattt acattgcttt gtaatataaa   4261

tctgttttag aactgcaaaa aaaaaaaaaa aaaatc                              4297


<210> SEQ ID NO 4
<211> LENGTH: 1267
<212> TYPE: PRT
<213> ORGANISM: Homo sapiens
<220> FEATURE:
<221> NAME/KEY: misc_feature
<222> LOCATION: (1)..(1)
<223> OTHER INFORMATION: The 'Xaa' at location 1 stands for Thr, Ala,
      Pro, or Ser.
<221> NAME/KEY: misc_feature
<222> LOCATION: (42)..(42)
<223> OTHER INFORMATION: The 'Xaa' at location 42 stands for Lys, Arg,
      Thr, or Met.
<221> NAME/KEY: misc_feature
<222> LOCATION: (98)..(98)
<223> OTHER INFORMATION: The 'Xaa' at location 98 stands for Lys, Arg,
      Thr, or Met.
<221> NAME/KEY: misc_feature
<222> LOCATION: (110)..(110)
<223> OTHER INFORMATION: The 'Xaa' at location 110 stands for Thr, Ala,
      Pro, or Ser.
<221> NAME/KEY: misc_feature
<222> LOCATION: (114)..(114)
<223> OTHER INFORMATION: The 'Xaa' at location 114 stands for Asn, Ser,
      Thr, or Ile.
<221> NAME/KEY: misc_feature
<222> LOCATION: (126)..(126)
<223> OTHER INFORMATION: The 'Xaa' at location 126 stands for Lys, or
      Asn.
<221> NAME/KEY: misc_feature
<222> LOCATION: (139)..(139)
<223> OTHER INFORMATION: The 'Xaa' at location 139 stands for Ile, Val,
      Leu, or Phe.
<221> NAME/KEY: misc_feature
<222> LOCATION: (144)..(144)
<223> OTHER INFORMATION: The 'Xaa' at location 144 stands for Thr.
<221> NAME/KEY: misc_feature
<222> LOCATION: (153)..(153)
<223> OTHER INFORMATION: The 'Xaa' at location 153 stands for Thr.
<221> NAME/KEY: misc_feature
<222> LOCATION: (166)..(166)
<223> OTHER INFORMATION: The 'Xaa' at location 166 stands for Ser,
      Gly, Arg, or Cys.
<221> NAME/KEY: misc_feature
<222> LOCATION: (173)..(173)
<223> OTHER INFORMATION: The 'Xaa' at location 173 stands for Ile,
      Val, Leu, or Phe.
<221> NAME/KEY: misc_feature
<222> LOCATION: (174)..(174)
<223> OTHER INFORMATION: The 'Xaa' at location 174 stands for Glu,
      or Lys.
<221> NAME/KEY: misc_feature
<222> LOCATION: (183)..(183)
<223> OTHER INFORMATION: The 'Xaa' at location 183 stands for Val.
<221> NAME/KEY: misc_feature
```

-continued

```
<222> LOCATION: (185)..(185)
<223> OTHER INFORMATION: The 'Xaa' at location 185 stands for Thr, Ala,
      Pro, or Ser.
<221> NAME/KEY: misc_feature
<222> LOCATION: (188)..(188)
<223> OTHER INFORMATION: The 'Xaa' at location 188 stands for Asn, Asp,
      His, or Tyr.
<221> NAME/KEY: misc_feature
<222> LOCATION: (202)..(202)
<223> OTHER INFORMATION: The 'Xaa' at location 202 stands for His, or
      Pro.
<221> NAME/KEY: misc_feature
<222> LOCATION: (204)..(204)
<223> OTHER INFORMATION: The 'Xaa' at location 204 stands for Glu, or
      Lys.
<221> NAME/KEY: misc_feature
<222> LOCATION: (205)..(205)
<223> OTHER INFORMATION: The 'Xaa' at location 205 stands for Asn, Ser,
      Thr, or Ile.
<221> NAME/KEY: misc_feature
<222> LOCATION: (207)..(207)
<223> OTHER INFORMATION: The 'Xaa' at location 207 stands for Asn, Asp,
      His, or Tyr.
<221> NAME/KEY: misc_feature
<222> LOCATION: (211)..(211)
<223> OTHER INFORMATION: The 'Xaa' at location 211 stands for Gln, Arg,
      Pro, or Leu.
<221> NAME/KEY: misc_feature
<222> LOCATION: (213)..(213)
<223> OTHER INFORMATION: The 'Xaa' at location 213 stands for Ser, Gly,
      Arg, or Cys.
<221> NAME/KEY: misc_feature
<222> LOCATION: (215)..(215)
<223> OTHER INFORMATION: The 'Xaa' at location 215 stands for Lys, Asn,
      Glu, Asp, Gln, His, a stop codon, or Tyr.
<221> NAME/KEY: misc_feature
<222> LOCATION: (227)..(227)
<223> OTHER INFORMATION: The 'Xaa' at location 227 stands for His, Arg,
      Pro, or Leu.
<221> NAME/KEY: misc_feature
<222> LOCATION: (228)..(228)
<223> OTHER INFORMATION: The 'Xaa' at location 228 stands for Asn, Asp,
      His, or Tyr.
<221> NAME/KEY: misc_feature
<222> LOCATION: (237)..(237)
<223> OTHER INFORMATION: The 'Xaa' at location 237 stands for Glu, or
      Asp.
<221> NAME/KEY: misc_feature
<222> LOCATION: (238)..(238)
<223> OTHER INFORMATION: The 'Xaa' at location 238 stands for Asn, Ser,
      Thr, Ile, Asp, Gly, Ala, Val, His, Arg, Pro, Leu, Tyr, Cys, or Phe.
<221> NAME/KEY: misc_feature
<222> LOCATION: (667)..(667)
<223> OTHER INFORMATION: The 'Xaa' at location 667 stands for Tyr, Cys,
      Ser, or Phe.
<221> NAME/KEY: misc_feature
<222> LOCATION: (725)..(725)
<223> OTHER INFORMATION: The 'Xaa' at location 725 stands for Lys, or
      Asn.
<221> NAME/KEY: misc_feature
<222> LOCATION: (727)..(727)
<223> OTHER INFORMATION: The 'Xaa' at location 727 stands for His, Arg,
      Pro, or Leu.
<221> NAME/KEY: misc_feature
<222> LOCATION: (735)..(735)
<223> OTHER INFORMATION: The 'Xaa' at location 735 stands for Glu, or
      Asp.
<221> NAME/KEY: misc_feature
<222> LOCATION: (741)..(741)
<223> OTHER INFORMATION: The 'Xaa' at location 741 stands for Met, Val,
      or Leu.
<221> NAME/KEY: misc_feature
<222> LOCATION: (763)..(763)
<223> OTHER INFORMATION: The 'Xaa' at location 763 stands for Leu, or
      Phe.
<221> NAME/KEY: misc_feature
<222> LOCATION: (764)..(764)
<223> OTHER INFORMATION: The 'Xaa' at location 764 stands for Tyr, Cys,
      Ser, or Phe.
```

-continued

<221> NAME/KEY: misc_feature
<222> LOCATION: (787)..(787)
<223> OTHER INFORMATION: The 'Xaa' at location 787 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (788)..(788)
<223> OTHER INFORMATION: The 'Xaa' at location 788 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (789)..(789)
<223> OTHER INFORMATION: The 'Xaa' at location 789 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (790)..(790)
<223> OTHER INFORMATION: The 'Xaa' at location 790 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (791)..(791)
<223> OTHER INFORMATION: The 'Xaa' at location 791 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (792)..(792)
<223> OTHER INFORMATION: The 'Xaa' at location 792 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (793)..(793)
<223> OTHER INFORMATION: The 'Xaa' at location 793 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (794)..(794)
<223> OTHER INFORMATION: The 'Xaa' at location 794 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (795)..(795)
<223> OTHER INFORMATION: The 'Xaa' at location 795 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (796)..(796)
<223> OTHER INFORMATION: The 'Xaa' at location 796 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (797)..(797)
<223> OTHER INFORMATION: The 'Xaa' at location 797 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (798)..(798)
<223> OTHER INFORMATION: The 'Xaa' at location 798 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (799)..(799)
<223> OTHER INFORMATION: The 'Xaa' at location 799 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (800)..(800)
<223> OTHER INFORMATION: The 'Xaa' at location 800 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (801)..(801)
<223> OTHER INFORMATION: The 'Xaa' at location 801 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (802)..(802)
<223> OTHER INFORMATION: The 'Xaa' at location 802 stands for Lys, Asn, Arg, Ser, Thr, Ile, Met, Glu, Asp, Gly, Ala, Val, Gln, His, Pro, -continued Leu, a stop codon, Tyr, Trp, Cys, or Phe.
<221> NAME/KEY: misc_feature
<222> LOCATION: (803)..(803)
<223> OTHER INFORMATION: The 'Xaa' at location 803 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (804)..(804)
<223> OTHER INFORMATION: The 'Xaa' at location 804 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (805)..(805)
<223> OTHER INFORMATION: The 'Xaa' at location 805 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (806)..(806)
<223> OTHER INFORMATION: The 'Xaa' at location 806 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (807)..(807)
<223> OTHER INFORMATION: The 'Xaa' at location 807 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (808)..(808)
<223> OTHER INFORMATION: The 'Xaa' at location 808 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (809)..(809)
<223> OTHER INFORMATION: The 'Xaa' at location 809 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (810)..(810)
<223> OTHER INFORMATION: The 'Xaa' at location 810 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (811)..(811)
<223> OTHER INFORMATION: The 'Xaa' at location 811 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (812)..(812)
<223> OTHER INFORMATION: The 'Xaa' at location 812 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (813)..(813)
<223> OTHER INFORMATION: The 'Xaa' at location 813 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (814)..(814)
<223> OTHER INFORMATION: The 'Xaa' at location 814 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (815)..(815)
<223> OTHER INFORMATION: The 'Xaa' at location 815 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (816)..(816)
<223> OTHER INFORMATION: The 'Xaa' at location 816 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (817)..(817)
<223> OTHER INFORMATION: The 'Xaa' at location 817 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (818)..(818)
<223> OTHER INFORMATION: The 'Xaa' at location 818 stands for Lys, Asn, -continued Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (819)..(819)
<223> OTHER INFORMATION: The 'Xaa' at location 819 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (820)..(820)
<223> OTHER INFORMATION: The 'Xaa' at location 820 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (821)..(821)
<223> OTHER INFORMATION: The 'Xaa' at location 821 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (822)..(822)
<223> OTHER INFORMATION: The 'Xaa' at location 822 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (823)..(823)
<223> OTHER INFORMATION: The 'Xaa' at location 823 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (824)..(824)
<223> OTHER INFORMATION: The 'Xaa' at location 824 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (825)..(825)
<223> OTHER INFORMATION: The 'Xaa' at location 825 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (826)..(826)
<223> OTHER INFORMATION: The 'Xaa' at location 826 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (827)..(827)
<223> OTHER INFORMATION: The 'Xaa' at location 827 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (828)..(828)
<223> OTHER INFORMATION: The 'Xaa' at location 828 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (829)..(829)
<223> OTHER INFORMATION: The 'Xaa' at location 829 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (830)..(830)
<223> OTHER INFORMATION: The 'Xaa' at location 830 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (831)..(831)
<223> OTHER INFORMATION: The 'Xaa' at location 831 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (832)..(832)
<223> OTHER INFORMATION: The 'Xaa' at location 832 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (833)..(833)
<223> OTHER INFORMATION: The 'Xaa' at location 833 stands for Lys, Asn,
Arg, Ser, Thr, Ile, Met, Glu, Asp, Gly, Ala, Val, Gln, His, Pro,
Leu, a stop codon, Tyr, Trp, Cys, or Phe.
<221> NAME/KEY: misc_feature
<222> LOCATION: (834)..(834)

-continued

<223> OTHER INFORMATION: The 'Xaa' at location 834 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (835)..(835)
<223> OTHER INFORMATION: The 'Xaa' at location 835 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (836)..(836)
<223> OTHER INFORMATION: The 'Xaa' at location 836 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (837)..(837)
<223> OTHER INFORMATION: The 'Xaa' at location 837 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (838)..(838)
<223> OTHER INFORMATION: The 'Xaa' at location 838 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (839)..(839)
<223> OTHER INFORMATION: The 'Xaa' at location 839 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (840)..(840)
<223> OTHER INFORMATION: The 'Xaa' at location 840 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (841)..(841)
<223> OTHER INFORMATION: The 'Xaa' at location 841 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (842)..(842)
<223> OTHER INFORMATION: The 'Xaa' at location 842 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (843)..(843)
<223> OTHER INFORMATION: The 'Xaa' at location 843 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (844)..(844)
<223> OTHER INFORMATION: The 'Xaa' at location 844 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (845)..(845)
<223> OTHER INFORMATION: The 'Xaa' at location 845 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (846)..(846)
<223> OTHER INFORMATION: The 'Xaa' at location 846 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (847)..(847)
<223> OTHER INFORMATION: The 'Xaa' at location 847 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (848)..(848)
<223> OTHER INFORMATION: The 'Xaa' at location 848 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (849)..(849)
<223> OTHER INFORMATION: The 'Xaa' at location 849 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature -continued
<222> LOCATION: (850)..(850)
<223> OTHER INFORMATION: The 'Xaa' at location 850 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (851)..(851)
<223> OTHER INFORMATION: The 'Xaa' at location 851 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (852)..(852)
<223> OTHER INFORMATION: The 'Xaa' at location 852 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (853)..(853)
<223> OTHER INFORMATION: The 'Xaa' at location 853 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (854)..(854)
<223> OTHER INFORMATION: The 'Xaa' at location 854 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (855)..(855)
<223> OTHER INFORMATION: The 'Xaa' at location 855 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (856)..(856)
<223> OTHER INFORMATION: The 'Xaa' at location 856 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (857)..(857)
<223> OTHER INFORMATION: The 'Xaa' at location 857 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (858)..(858)
<223> OTHER INFORMATION: The 'Xaa' at location 858 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (859)..(859)
<223> OTHER INFORMATION: The 'Xaa' at location 859 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (860)..(860)
<223> OTHER INFORMATION: The 'Xaa' at location 860 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (861)..(861)
<223> OTHER INFORMATION: The 'Xaa' at location 861 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (862)..(862)
<223> OTHER INFORMATION: The 'Xaa' at location 862 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (863)..(863)
<223> OTHER INFORMATION: The 'Xaa' at location 863 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (864)..(864)
<223> OTHER INFORMATION: The 'Xaa' at location 864 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (865)..(865)
<223> OTHER INFORMATION: The 'Xaa' at location 865 stands for Lys, Asn, Arg, Ser, Thr, Ile, Met, Glu, Asp, Gly, Ala, Val, Gln, His, Pro, Leu, a stop codon, Tyr, Trp, Cys, or Phe.

-continued

<221> NAME/KEY: misc_feature
<222> LOCATION: (866)..(866)
<223> OTHER INFORMATION: The 'Xaa' at location 866 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (867)..(867)
<223> OTHER INFORMATION: The 'Xaa' at location 867 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (868)..(868)
<223> OTHER INFORMATION: The 'Xaa' at location 868 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (869)..(869)
<223> OTHER INFORMATION: The 'Xaa' at location 869 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (870)..(870)
<223> OTHER INFORMATION: The 'Xaa' at location 870 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (871)..(871)
<223> OTHER INFORMATION: The 'Xaa' at location 871 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (872)..(872)
<223> OTHER INFORMATION: The 'Xaa' at location 872 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (873)..(873)
<223> OTHER INFORMATION: The 'Xaa' at location 873 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (874)..(874)
<223> OTHER INFORMATION: The 'Xaa' at location 874 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (875)..(875)
<223> OTHER INFORMATION: The 'Xaa' at location 875 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (876)..(876)
<223> OTHER INFORMATION: The 'Xaa' at location 876 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (877)..(877)
<223> OTHER INFORMATION: The 'Xaa' at location 877 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (878)..(878)
<223> OTHER INFORMATION: The 'Xaa' at location 878 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (879)..(879)
<223> OTHER INFORMATION: The 'Xaa' at location 879 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (880)..(880)
<223> OTHER INFORMATION: The 'Xaa' at location 880 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<221> NAME/KEY: misc_feature
<222> LOCATION: (881)..(881)
<223> OTHER INFORMATION: The 'Xaa' at location 881 stands for Lys, Asn, Arg, Ser, Thr, Ile, Met, Glu, Asp, Gly, Ala, Val, Gln, His, Pro, -continued

```
      Leu, a stop codon, Tyr, Trp, Cys, or Phe.
<221> NAME/KEY: misc_feature
<222> LOCATION: (882)..(882)
<223> OTHER INFORMATION: The 'Xaa' at location 882 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (883)..(883)
<223> OTHER INFORMATION: The 'Xaa' at location 883 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (884)..(884)
<223> OTHER INFORMATION: The 'Xaa' at location 884 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (885)..(885)
<223> OTHER INFORMATION: The 'Xaa' at location 885 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (886)..(886)
<223> OTHER INFORMATION: The 'Xaa' at location 886 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (887)..(887)
<223> OTHER INFORMATION: The 'Xaa' at location 887 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (888)..(888)
<223> OTHER INFORMATION: The 'Xaa' at location 888 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (889)..(889)
<223> OTHER INFORMATION: The 'Xaa' at location 889 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (890)..(890)
<223> OTHER INFORMATION: The 'Xaa' at location 890 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (891)..(891)
<223> OTHER INFORMATION: The 'Xaa' at location 891 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<221> NAME/KEY: misc_feature
<222> LOCATION: (892)..(892)
<223> OTHER INFORMATION: The 'Xaa' at location 892 stands for Met, Val,
      or Leu.
<221> NAME/KEY: misc_feature
<222> LOCATION: (993)..(993)
<223> OTHER INFORMATION: The 'Xaa' at location 993 stands for Lys, Glu,
      Gln, or a stop cod on.
<221> NAME/KEY: misc_feature
<222> LOCATION: (1014)..(1014)
<223> OTHER INFORMATION: The 'Xaa' at location 1014 stands for Gly.
<221> NAME/KEY: misc_feature
<222> LOCATION: (1)..(1)
<223> OTHER INFORMATION: Sequences not determined at this position .
      Unknown residue put in to provide alignment.
<221> NAME/KEY: misc_feature
<222> LOCATION: (125)..(125)
<223> OTHER INFORMATION: Sequences not determined at this position .
      Unknown residue put in to provide alignment.
<221> NAME/KEY: misc_feature
<222> LOCATION: (293)..(293)
<223> OTHER INFORMATION: Sequences not determined at this position .
      Unknown residue put in to provide alignment.
<221> NAME/KEY: misc_feature
<222> LOCATION: (328)..(328)
<223> OTHER INFORMATION: Sequences not determined at this position .
      Unknown residue put in to provide alignment.
<221> NAME/KEY: misc_feature
```

-continued

<222> LOCATION: (341)..(341)
<223> OTHER INFORMATION: Sequences not determined at this position .
Unknown residue put in to provide alignment.
<221> NAME/KEY: misc_feature
<222> LOCATION: (378)..(378)
<223> OTHER INFORMATION: Sequences not determined at this position .
Unknown residue put in to provide alignment.
<221> NAME/KEY: misc_feature
<222> LOCATION: (415)..(415)
<223> OTHER INFORMATION: Sequences not determined at this position .
Unknown residue put in to provide alignment.
<221> NAME/KEY: misc_feature
<222> LOCATION: (432)..(432)
<223> OTHER INFORMATION: Sequences not determined at this position .
Unknown residue put in to provide alignment.
<221> NAME/KEY: misc_feature
<222> LOCATION: (459)..(459)
<223> OTHER INFORMATION: Sequences not determined at this position .
Unknown residue put in to provide alignment.
<221> NAME/KEY: misc_feature
<222> LOCATION: (496)..(496)
<223> OTHER INFORMATION: Sequences not determined at this position .
Unknown residue put in to provide alignment.
<221> NAME/KEY: misc_feature
<222> LOCATION: (517)..(517)
<223> OTHER INFORMATION: Sequences not determined at this position .
Unknown residue put in to provide alignment.
<221> NAME/KEY: misc_feature
<222> LOCATION: (534)..(534)
<223> OTHER INFORMATION: Sequences not determined at this position .
Unknown residue put in to provide alignment.
<221> NAME/KEY: misc_feature
<222> LOCATION: (553)..(553)
<223> OTHER INFORMATION: Sequences not determined at this position .
Unknown residue put in to provide alignment.
<221> NAME/KEY: misc_feature
<222> LOCATION: (562)..(562)
<223> OTHER INFORMATION: Sequences not determined at this position .
Unknown residue put in to provide alignment.
<221> NAME/KEY: misc_feature
<222> LOCATION: (614)..(614)
<223> OTHER INFORMATION: Sequences not determined at this position .
Unknown residue put in to provide alignment.
<221> NAME/KEY: misc_feature
<222> LOCATION: (619)..(619)
<223> OTHER INFORMATION: Sequences not determined at this position .
Unknown residue put in to provide alignment.
<221> NAME/KEY: misc_feature
<222> LOCATION: (632)..(632)
<223> OTHER INFORMATION: Sequences not determined at this position .
Unknown residue put in to provide alignment.
<221> NAME/KEY: misc_feature
<222> LOCATION: (637)..(637)
<223> OTHER INFORMATION: Sequences not determined at this position .
Unknown residue put in to provide alignment.
<221> NAME/KEY: misc_feature
<222> LOCATION: (643)..(643)
<223> OTHER INFORMATION: Sequences not determined at this position .
Unknown residue put in to provide alignment.
<221> NAME/KEY: misc_feature
<222> LOCATION: (680)..(680)
<223> OTHER INFORMATION: Sequences not determined at this position .
Unknown residue put in to provide alignment.
<221> NAME/KEY: misc_feature
<222> LOCATION: (682)..(682)
<223> OTHER INFORMATION: Sequences not determined at this position .
Unknown residue put in to provide alignment.
<221> NAME/KEY: misc_feature
<222> LOCATION: (711)..(713)
<223> OTHER INFORMATION: Sequences not determined at this position .
Unknown residue put in to provide alignment.
<221> NAME/KEY: misc_feature
<222> LOCATION: (1971)..(1971)
<223> OTHER INFORMATION: Sequences not determined at this position .
Unknown residue put in to provide alignment.
<221> NAME/KEY: misc_feature
<222> LOCATION: (2000)..(2000)
<223> OTHER INFORMATION: Sequences not determined at this position .
Unknown residue put in to provide alignment.

-continued

<221> NAME/KEY: misc_feature
<222> LOCATION: (2175)..(2175)
<223> OTHER INFORMATION: Sequences not determined at this position .
      Unknown residue put in to provide alignment.
<221> NAME/KEY: misc_feature
<222> LOCATION: (2180)..(2180)
<223> OTHER INFORMATION: Sequences not determined at this position .
      Unknown residue put in to provide alignment.
<221> NAME/KEY: misc_feature
<222> LOCATION: (2205)..(2205)
<223> OTHER INFORMATION: Sequences not determined at this position .
      Unknown residue put in to provide alignment.
<221> NAME/KEY: misc_feature
<222> LOCATION: (2221)..(2221)
<223> OTHER INFORMATION: Sequences not determined at this position .
      Unknown residue put in to provide alignment.
<221> NAME/KEY: misc_feature
<222> LOCATION: (2289)..(2289)
<223> OTHER INFORMATION: Sequences not determined at this position .
      Unknown residue put in to provide alignment.
<221> NAME/KEY: misc_feature
<222> LOCATION: (2316)..(2316)
<223> OTHER INFORMATION: Sequences not determined at this position .
      Unknown residue put in to provide alignment.
<221> NAME/KEY: misc_feature
<222> LOCATION: (2359)..(2674)
<223> OTHER INFORMATION: Sequences not determined at this position .
      Unknown residue put in to provide alignment.
<221> NAME/KEY: misc_feature
<222> LOCATION: (2977)..(2977)
<223> OTHER INFORMATION: Sequences not determined at this position .
      Unknown residue put in to provide alignment.
<221> NAME/KEY: misc_feature
<222> LOCATION: (2291)..(2291)
<223> OTHER INFORMATION: Sequences not determined at this position .
      Unknown residue put in to provide alignment.

<400> SEQUENCE: 4

```
Xaa His Ala Ser Gly Gln Glu Gly Pro Cys Gln Leu Pro Pro Pro Arg
1               5                   10                  15

Arg Phe Arg Thr Arg Thr Ala Asp Ser Arg Cys Leu Arg Arg Arg Gly
            20                  25                  30

Ala Ala Gly Gly Gln Gly Ala His Arg Xaa Gly Ala Arg Gly Arg Gly
        35                  40                  45

His Gly Thr Ala Pro Asp Pro Val Thr Ala Gly Ser Gln Ala Ala Arg
    50                  55                  60

Ala Leu Ser Ala Ser Ser Pro Gly Gly Leu Ala Leu Leu Leu Ala Gly
65                  70                  75                  80

Pro Gly Leu Leu Leu Arg Leu Leu Ala Leu Leu Leu Ala Val Ala Ala
                85                  90                  95

Ala Xaa Ile Met Ser Gly Arg Arg Cys Ala Gly Gly Gly Xaa Ala Cys
            100                 105                 110

Ala Xaa Ala Ala Ala Glu Ala Val Glu Pro Ala Ala Arg Xaa Leu Phe
        115                 120                 125

Glu Ala Cys Arg Asn Gly Asp Val Glu Arg Xaa Lys Lys Leu Val Xaa
    130                 135                 140

Pro Glu Lys Val Asn Ser Arg Asp Xaa Ala Gly Arg Lys Ser Thr Pro
145                 150                 155                 160

Leu His Phe Pro Ala Xaa Phe Gly Arg Lys Asp Leu Xaa Xaa Tyr Leu
                165                 170                 175

Leu Thr Asn Gly Ala Asn Xaa Gln Xaa Arg Asp Xaa Gly Gly Leu Ile
            180                 185                 190

Pro Leu His Asn Ala Cys Ser Phe Gly Xaa Ala Xaa Xaa Ile Xaa Leu
        195                 200                 205

Leu Leu Xaa His Xaa Ala Xaa Pro Asn Ala Arg Asp Asn Trp Asn Tyr
```

-continued

```
    210                 215                 220

Thr Pro Xaa Xaa Glu Ala Ala Ile Lys Gly Lys Ile Xaa Xaa Cys Ile
225                 230                 235                 240

Val Leu Leu Gln His Gly Ala Glu Pro Thr Ile Arg Asn Thr Asp Gly
                245                 250                 255

Arg Thr Ala Leu Asp Leu Ala Asp Pro Ser Ala Lys Ala Val Leu Thr
            260                 265                 270

Gly Glu Tyr Lys Lys Asp Glu Leu Leu Glu Ser Ala Arg Ser Gly Asn
        275                 280                 285

Glu Glu Lys Met Met Ala Leu Leu Thr Pro Leu Asn Val Asn Cys His
    290                 295                 300

Ala Ser Asp Gly Arg Lys Ser Thr Pro Leu His Leu Ala Ala Gly Tyr
305                 310                 315                 320

Asn Arg Val Lys Ile Val Gln Leu Leu Leu Gln His Gly Ala Asp Val
                325                 330                 335

His Ala Lys Asp Lys Gly Asp Leu Val Pro Leu His Asn Ala Cys Ser
            340                 345                 350

Tyr Gly His Tyr Glu Val Thr Glu Leu Leu Val Lys His Gly Ala Cys
        355                 360                 365

Val Asn Ala Met Asp Leu Trp Gln Phe Thr Pro Leu His Glu Ala Ala
    370                 375                 380

Ser Lys Asn Arg Val Glu Val Cys Ser Leu Leu Leu Ser Tyr Gly Ala
385                 390                 395                 400

Asp Pro Thr Leu Leu Asn Cys His Asn Lys Ser Ala Ile Asp Leu Ala
                405                 410                 415

Pro Thr Pro Gln Leu Lys Glu Arg Leu Ala Tyr Glu Phe Lys Gly His
            420                 425                 430

Ser Leu Leu Gln Ala Ala Arg Glu Ala Asp Val Thr Arg Ile Lys Lys
        435                 440                 445

His Leu Ser Leu Glu Met Val Asn Phe Lys His Pro Gln Thr His Glu
    450                 455                 460

Thr Ala Leu His Cys Ala Ala Ala Ser Pro Tyr Pro Lys Arg Lys Gln
465                 470                 475                 480

Ile Cys Glu Leu Leu Leu Arg Lys Gly Ala Asn Ile Asn Glu Lys Thr
                485                 490                 495

Lys Glu Phe Leu Thr Pro Leu His Val Ala Ser Glu Lys Ala His Asn
            500                 505                 510

Asp Val Val Glu Val Val Val Lys His Glu Ala Lys Val Asn Ala Leu
        515                 520                 525

Asp Asn Leu Gly Gln Thr Ser Leu His Arg Ala Ala Tyr Cys Gly His
    530                 535                 540

Leu Gln Thr Cys Arg Leu Leu Leu Ser Tyr Gly Cys Asp Pro Asn Ile
545                 550                 555                 560

Ile Ser Leu Gln Gly Phe Thr Ala Leu Gln Met Gly Asn Glu Asn Val
                565                 570                 575

Gln Gln Leu Leu Gln Glu Gly Ile Ser Leu Gly Asn Ser Glu Ala Asp
            580                 585                 590

Arg Gln Leu Leu Glu Ala Ala Lys Ala Gly Asp Val Glu Thr Val Lys
        595                 600                 605

Lys Leu Cys Thr Val Gln Ser Val Asn Cys Arg Asp Ile Glu Gly Arg
    610                 615                 620

Gln Ser Thr Pro Leu His Phe Ala Ala Gly Tyr Asn Arg Val Ser Val
625                 630                 635                 640
```

-continued

```
Val Glu Tyr Leu Leu Gln His Gly Ala Asp Val His Ala Lys Asp Lys
            645                 650                 655

Gly Gly Leu Val Pro Leu His Asn Ala Cys Xaa Tyr Gly His Tyr Glu
        660                 665                 670

Val Ala Glu Leu Leu Val Lys His Gly Ala Val Val Asn Val Ala Asp
    675                 680                 685

Leu Trp Lys Phe Thr Pro Leu His Glu Ala Ala Ala Lys Gly Lys Tyr
    690                 695                 700

Glu Ile Cys Lys Leu Leu Leu Gln His Gly Ala Asp Pro Thr Lys Lys
705                 710                 715                 720

Lys Lys Lys Gly Xaa Ile Xaa Leu Asp Leu Val Lys Asp Gly Xaa Thr
            725                 730                 735

Asp Ile Gln Asp Xaa Leu Arg Gly Asp Ala Val Leu Leu Asp Ala Ala
        740                 745                 750

Lys Lys Gly Cys Leu Ala Arg Val Lys Lys Xaa Xaa Phe Pro Asp Asn
    755                 760                 765

Val Asn Cys Arg Asp Thr Gln Gly Arg His Ser Thr Pro Leu His Leu
    770                 775                 780

Ala Gly Xaa Xaa Xaa Xaa Xaa Xaa Xaa Xaa Xaa Xaa Xaa Xaa Xaa Xaa
785                 790                 795                 800

Xaa Xaa Xaa Xaa Xaa Xaa Xaa Xaa Xaa Xaa Xaa Xaa Xaa Xaa Xaa Xaa
            805                 810                 815

Xaa Xaa Xaa Xaa Xaa Xaa Xaa Xaa Xaa Xaa Xaa Xaa Xaa Xaa Xaa Xaa
        820                 825                 830

Xaa Xaa Xaa Xaa Xaa Xaa Xaa Xaa Xaa Xaa Xaa Xaa Xaa Xaa Xaa
    835                 840                 845

Xaa Xaa Xaa Xaa Xaa Xaa Xaa Xaa Xaa Xaa Xaa Xaa Xaa Xaa Xaa Xaa
    850                 855                 860

Xaa Xaa Xaa Xaa Xaa Xaa Xaa Xaa Xaa Xaa Xaa Xaa Xaa Xaa Xaa Xaa
865                 870                 875                 880

Xaa Xaa Xaa Xaa Xaa Xaa Xaa Xaa Xaa Xaa Xaa Xaa Thr Ala Ala Met
            885                 890                 895

Pro Pro Ser Val Leu Pro Ser Cys Asn Lys Pro Gln Val Leu Asn Gly
        900                 905                 910

Val Arg Ser Pro Gly Ala Thr Ala Asp Ala Leu Ser Ser Gly Pro Ser
    915                 920                 925

Ser Pro Ser Ser Leu Ser Ala Ala Ser Ser Leu Asp Asn Leu Ser Gly
    930                 935                 940

Ser Phe Ser Glu Leu Ser Ser Val Val Ser Ser Ser Gly Thr Glu Gly
945                 950                 955                 960

Ala Ser Ser Leu Glu Lys Lys Glu Val Pro Gly Val Asp Phe Ser Ile
            965                 970                 975

Thr Gln Phe Val Arg Asn Leu Gly Leu Glu His Leu Met Asp Ile Phe
        980                 985                 990

Xaa Arg Glu Gln Ile Thr Leu Asp  Val Leu Val Glu Met  Gly His Lys
    995                 1000                 1005

Glu Leu  Lys Glu Ile Xaa Ile  Asn Ala Tyr Gly His  Arg His Lys
    1010                 1015                 1020

Leu Ile  Lys Ser Phe Glu Arg  Leu Ile Ser Gly Gln  Gln Gly Leu
    1025                 1030                 1035

Asn Pro  Tyr Leu Thr Leu Asn  Thr Ser Gly Ser Gly  Thr Ile Leu
    1040                 1045                 1050
```

-continued

```
Ile Asp  Leu Ser Pro Asp Asp  Lys Glu Phe Gln Ser  Val Glu Glu
    1055                1060                1065

Glu Met  Gln Ser Thr Val Arg  Glu His Arg Asp Gly  Gly His Ala
    1070                1075                1080

Gly Gly  Ile Phe Asn Arg Tyr  Asn Ile Leu Lys Ile  Gln Lys Val
    1085                1090                1095

Cys Asn  Arg Ala Lys Ile Arg  His Glu Glu Arg Tyr  Thr His Arg
    1100                1105                1110

Arg Lys  Glu Val Ser Glu Glu  Asn His Asn His Ala  Asn Glu Arg
    1115                1120                1125

Met Leu  Phe His Gly Ser Pro  Phe Val Asn Ala Ile  Ile His Lys
    1130                1135                1140

Gly Phe  Asp Glu Arg His Ala  Tyr Ile Gly Gly Met  Phe Gly Ala
    1145                1150                1155

Gly Ile  Tyr Phe Ala Glu Asn  Ser Ser Lys Ser Asn  Gln Tyr Val
    1160                1165                1170

Tyr Gly  Ile Gly Gly Gly Thr  Gly Cys Pro Val His  Lys Asp Arg
    1175                1180                1185

Ser Cys  Tyr Ile Cys His Arg  Gln Leu Leu Phe Cys  Arg Val Thr
    1190                1195                1200

Leu Gly  Lys Ser Phe Leu Gln  Phe Ser Ala Met Lys  Met Ala His
    1205                1210                1215

Ser Pro  Pro Gly His His Ser  Val Thr Gly Arg Pro  Ser Val Asn
    1220                1225                1230

Gly Leu  Ala Leu Ala Glu Tyr  Val Ile Tyr Arg Gly  Glu Gln Ala
    1235                1240                1245

Tyr Pro  Glu Tyr Leu Ile Thr  Tyr Gln Ile Met Arg  Pro Glu Gly
    1250                1255                1260

Met Val  Asp Gly
    1265


<210> SEQ ID NO 5
<211> LENGTH: 4275
<212> TYPE: DNA
<213> ORGANISM: Homo sapiens
<220> FEATURE:
<221> NAME/KEY: CDS
<222> LOCATION: (284)..(3781)
<223> OTHER INFORMATION:

<400> SEQUENCE: 5

ggcaggaggg gccttgccag cttccgccgc cgcgtcgttt caggacccgg acggcggatt      60

cgcgctgcct ccgccgccgc ggggcagccg gggggcaggg agcccatcga ggggcgcgcg     120

tgggcgcggc catgggactg cgccggatcc ggtgacagca gggagccaag cggcccgggc     180

cctgagcgcg tcttctccgg ggggcctcgc cctcctgctc gcggggccgg ggctcctgct     240

ccggttgctg gcgctgttgc tggctgtggc ggcggccagg atc atg tcg ggt cgc      295
                                                Met Ser Gly Arg
                                                1

cgc tgc gcc ggc ggg gga gcg gcc tgc gcg agc gcc gcg gcc gag gcc      343
Arg Cys Ala Gly Gly Gly Ala Ala Cys Ala Ser Ala Ala Ala Glu Ala
5                   10                  15                  20

gtg gag ccg gcc gcc cga gag ctg ttc gag gcg tgc cgc aac ggg gac      391
Val Glu Pro Ala Ala Arg Glu Leu Phe Glu Ala Cys Arg Asn Gly Asp
                25                  30                  35

gtg gaa cga gtc aag agg ctg gtg acg cct gag aag gtg aac agc cgc      439
Val Glu Arg Val Lys Arg Leu Val Thr Pro Glu Lys Val Asn Ser Arg
```

-continued

```
            40                  45                  50

gac acg gcg ggc agg aaa tcc acc ccg ctg cac ttc gcc gca ggt ttt      487
Asp Thr Ala Gly Arg Lys Ser Thr Pro Leu His Phe Ala Ala Gly Phe
        55                  60                  65

ggg cgg aaa gac gta gtt gaa tat ttg ctt cag aat ggt gca aat gtc      535
Gly Arg Lys Asp Val Val Glu Tyr Leu Leu Gln Asn Gly Ala Asn Val
    70                  75                  80

caa gca cgt gat gat ggg ggc ctt att cct ctt cat aat gca tgc tct      583
Gln Ala Arg Asp Asp Gly Gly Leu Ile Pro Leu His Asn Ala Cys Ser
85                  90                  95                  100

ttt ggt cat gct gaa gta gtc aat ctc ctt ttg cga cat ggt gca gac      631
Phe Gly His Ala Glu Val Val Asn Leu Leu Leu Arg His Gly Ala Asp
                105                 110                 115

ccc aat gct cga gat aat tgg aat tat act cct ctc cat gaa gct gca      679
Pro Asn Ala Arg Asp Asn Trp Asn Tyr Thr Pro Leu His Glu Ala Ala
            120                 125                 130

att aaa gga aag att gat gtt tgc att gtg ctg tta cag cat gga gct      727
Ile Lys Gly Lys Ile Asp Val Cys Ile Val Leu Leu Gln His Gly Ala
        135                 140                 145

gag cca acc atc cga aat aca gat gga agg aca gca ttg gat tta gca      775
Glu Pro Thr Ile Arg Asn Thr Asp Gly Arg Thr Ala Leu Asp Leu Ala
    150                 155                 160

gat cca tct gcc aaa gca gtg ctt act ggt gaa tat aag aaa gat gaa      823
Asp Pro Ser Ala Lys Ala Val Leu Thr Gly Glu Tyr Lys Lys Asp Glu
165                 170                 175                 180

ctc tta gaa agt gcc agg agt ggc aat gaa gaa aaa atg atg gct cta      871
Leu Leu Glu Ser Ala Arg Ser Gly Asn Glu Glu Lys Met Met Ala Leu
                185                 190                 195

ctc aca cca tta aat gtc aac tgc cac gca agt gat ggc aga aag tca      919
Leu Thr Pro Leu Asn Val Asn Cys His Ala Ser Asp Gly Arg Lys Ser
            200                 205                 210

act cca tta cat ttg gca gca gga tat aac aga gta aag att gta cag      967
Thr Pro Leu His Leu Ala Ala Gly Tyr Asn Arg Val Lys Ile Val Gln
        215                 220                 225

ctg tta ctg caa cat gga gct gat gtc cat gct aaa gat aaa ggt gat     1015
Leu Leu Leu Gln His Gly Ala Asp Val His Ala Lys Asp Lys Gly Asp
    230                 235                 240

ctg gta cca tta cac aat gcc tgt tct tat ggt cat tat gaa gta act     1063
Leu Val Pro Leu His Asn Ala Cys Ser Tyr Gly His Tyr Glu Val Thr
245                 250                 255                 260

gaa ctt ttg gtc aag cat ggt gcc tgt gta aat gca atg gac ttg tgg     1111
Glu Leu Leu Val Lys His Gly Ala Cys Val Asn Ala Met Asp Leu Trp
                265                 270                 275

caa ttc act cct ctt cat gag gca gct tct aag aac agg gtt gaa gta     1159
Gln Phe Thr Pro Leu His Glu Ala Ala Ser Lys Asn Arg Val Glu Val
            280                 285                 290

tgt tct ctt ctc tta agt tat ggt gca gac cca aca ctg ctc aat tgt     1207
Cys Ser Leu Leu Leu Ser Tyr Gly Ala Asp Pro Thr Leu Leu Asn Cys
        295                 300                 305

cac aat aaa agt gct ata gac ttg gct ccc aca cca cag tta aaa gaa     1255
His Asn Lys Ser Ala Ile Asp Leu Ala Pro Thr Pro Gln Leu Lys Glu
    310                 315                 320

aga tta gca tat gaa ttt aaa ggc cac tcg ttg ctg caa gct gca cga     1303
Arg Leu Ala Tyr Glu Phe Lys Gly His Ser Leu Leu Gln Ala Ala Arg
325                 330                 335                 340

gaa gct gat gtt act cga atc aaa aaa cat ctc tct ctg gaa atg gtg     1351
Glu Ala Asp Val Thr Arg Ile Lys Lys His Leu Ser Leu Glu Met Val
                345                 350                 355

aat ttc aag cat cct caa aca cat gaa aca gca ttg cat tgt gct gct     1399
```

-continued

```
Asn Phe Lys His Pro Gln Thr His Glu Thr Ala Leu His Cys Ala Ala
            360                 365                 370

gca tct cca tat ccc aaa aga aag caa ata tgt gaa ctg ttg cta aga     1447
Ala Ser Pro Tyr Pro Lys Arg Lys Gln Ile Cys Glu Leu Leu Leu Arg
        375                 380                 385

aaa gga gca aac atc aat gaa aag act aaa gaa ttc ttg act cct ctg     1495
Lys Gly Ala Asn Ile Asn Glu Lys Thr Lys Glu Phe Leu Thr Pro Leu
    390                 395                 400

cac gtg gca tct gag aaa gct cat aat gat gtt gtt gaa gta gtg gtg     1543
His Val Ala Ser Glu Lys Ala His Asn Asp Val Val Glu Val Val Val
405                 410                 415                 420

aaa cat gaa gca aag gtt aat gct ctg gat aat ctt ggt cag act tct     1591
Lys His Glu Ala Lys Val Asn Ala Leu Asp Asn Leu Gly Gln Thr Ser
                425                 430                 435

cta cac aga gct gca tat tgt ggt cat cta caa acc tgc cgc cta ctc     1639
Leu His Arg Ala Ala Tyr Cys Gly His Leu Gln Thr Cys Arg Leu Leu
            440                 445                 450

ctg agc tat ggg tgt gat cct aac att ata tcc ctt cag ggc ttt act     1687
Leu Ser Tyr Gly Cys Asp Pro Asn Ile Ile Ser Leu Gln Gly Phe Thr
        455                 460                 465

gct tta cag atg gga aat gaa aat gta cag caa ctc ctc caa gag ggt     1735
Ala Leu Gln Met Gly Asn Glu Asn Val Gln Gln Leu Leu Gln Glu Gly
    470                 475                 480

atc tca tta ggt aat tca gag gca gac aga caa ttg ctg gaa gct gca     1783
Ile Ser Leu Gly Asn Ser Glu Ala Asp Arg Gln Leu Leu Glu Ala Ala
485                 490                 495                 500

aag gct gga gat gtc gaa act gta aaa aaa ctg tgt act gtt cag agt     1831
Lys Ala Gly Asp Val Glu Thr Val Lys Lys Leu Cys Thr Val Gln Ser
                505                 510                 515

gtc aac tgc aga gac att gaa ggg cgt cag tct aca cca ctt cat ttt     1879
Val Asn Cys Arg Asp Ile Glu Gly Arg Gln Ser Thr Pro Leu His Phe
            520                 525                 530

gca gct ggg tat aac aga gtg tcc gtg gtg gaa tat ctg cta cag cat     1927
Ala Ala Gly Tyr Asn Arg Val Ser Val Val Glu Tyr Leu Leu Gln His
        535                 540                 545

gga gct gat gtg cat gct aaa gat aaa gga ggc ctt gta cct ttg cac     1975
Gly Ala Asp Val His Ala Lys Asp Lys Gly Gly Leu Val Pro Leu His
    550                 555                 560

aat gca tgt tct tat gga cat tat gaa gtt gca gaa ctt ctt gtt aaa     2023
Asn Ala Cys Ser Tyr Gly His Tyr Glu Val Ala Glu Leu Leu Val Lys
565                 570                 575                 580

cat gga gca gta gtt aat gta gct gat tta tgg aaa ttt aca cct tta     2071
His Gly Ala Val Val Asn Val Ala Asp Leu Trp Lys Phe Thr Pro Leu
                585                 590                 595

cat gaa gca gca gca aaa gga aaa tat gaa att tgc aaa ctt ctg ctc     2119
His Glu Ala Ala Ala Lys Gly Lys Tyr Glu Ile Cys Lys Leu Leu Leu
            600                 605                 610

cag cat ggt gca gac cct aca aaa aaa aac agg gat gga aat act cct     2167
Gln His Gly Ala Asp Pro Thr Lys Lys Asn Arg Asp Gly Asn Thr Pro
        615                 620                 625

ttg gat ctt gtt aaa gat gga gat aca gat att caa gat ctg ctt agg     2215
Leu Asp Leu Val Lys Asp Gly Asp Thr Asp Ile Gln Asp Leu Leu Arg
    630                 635                 640

gga gat gca gct ttg cta gat gct gcc aag aag ggt tgt tta gcc aga     2263
Gly Asp Ala Ala Leu Leu Asp Ala Ala Lys Lys Gly Cys Leu Ala Arg
645                 650                 655                 660

gtg aag aag ttg tct tct cct gat aat gta aat tgc cgc gat acc caa     2311
Val Lys Lys Leu Ser Ser Pro Asp Asn Val Asn Cys Arg Asp Thr Gln
                665                 670                 675
```

-continued

```
ggc aga cat tca aca cct tta cat tta gca gct ggt tat aat aat tta      2359
Gly Arg His Ser Thr Pro Leu His Leu Ala Ala Gly Tyr Asn Asn Leu
            680                 685                 690

gaa gtt gca gag tat ttg tta caa cac gga gct gat gtg aat gcc caa      2407
Glu Val Ala Glu Tyr Leu Leu Gln His Gly Ala Asp Val Asn Ala Gln
        695                 700                 705

gac aaa gga gga ctt att cct tta cat aat gca gca tct tac ggg cat      2455
Asp Lys Gly Gly Leu Ile Pro Leu His Asn Ala Ala Ser Tyr Gly His
    710                 715                 720

gta gat gta gca gct cta cta ata aag tat aat gca tgt gtc aat gcc      2503
Val Asp Val Ala Ala Leu Leu Ile Lys Tyr Asn Ala Cys Val Asn Ala
725                 730                 735                 740

acg gac aaa tgg gct ttc aca cct ttg cac gaa gca gcc caa aag gga      2551
Thr Asp Lys Trp Ala Phe Thr Pro Leu His Glu Ala Ala Gln Lys Gly
                745                 750                 755

cga aca cag ctt tgt gct ttg ttg cta gcc cat gga gct gac ccg act      2599
Arg Thr Gln Leu Cys Ala Leu Leu Leu Ala His Gly Ala Asp Pro Thr
            760                 765                 770

ctt aaa aat cag gaa gga caa aca cct tta gat tta gtt tca gcg gat      2647
Leu Lys Asn Gln Glu Gly Gln Thr Pro Leu Asp Leu Val Ser Ala Asp
        775                 780                 785

gat gtc agc gct ctt ctg aca gca gcc atg ccc cca tct gct ctg ccc      2695
Asp Val Ser Ala Leu Leu Thr Ala Ala Met Pro Pro Ser Ala Leu Pro
    790                 795                 800

tct tgt tac aag cct caa gtg ctc aat ggt gtg aga agc cca gga gcc      2743
Ser Cys Tyr Lys Pro Gln Val Leu Asn Gly Val Arg Ser Pro Gly Ala
805                 810                 815                 820

act gca gat gct ctc tct tca ggt cca tct agc cca tca agc ctt tct      2791
Thr Ala Asp Ala Leu Ser Ser Gly Pro Ser Ser Pro Ser Ser Leu Ser
                825                 830                 835

gca gcc agc agt ctt gac aac tta tct ggg agt ttt tca gaa ctg tct      2839
Ala Ala Ser Ser Leu Asp Asn Leu Ser Gly Ser Phe Ser Glu Leu Ser
            840                 845                 850

tca gta gtt agt tca agt gga aca gag ggt gct tcc agt ttg gag aaa      2887
Ser Val Val Ser Ser Ser Gly Thr Glu Gly Ala Ser Ser Leu Glu Lys
        855                 860                 865

aag gag gtt cca gga gta gat ttt agc ata act caa ttc gta agg aat      2935
Lys Glu Val Pro Gly Val Asp Phe Ser Ile Thr Gln Phe Val Arg Asn
    870                 875                 880

ctt gga ctt gag cac cta atg gat ata ttt gag aga gaa cag atc act      2983
Leu Gly Leu Glu His Leu Met Asp Ile Phe Glu Arg Glu Gln Ile Thr
885                 890                 895                 900

ttg gat gta tta gtt gag atg ggg cac aag gag ctg aag gag att gga      3031
Leu Asp Val Leu Val Glu Met Gly His Lys Glu Leu Lys Glu Ile Gly
                905                 910                 915

atc aat gct tat gga cat agg cac aaa cta att aaa gga gtc gag aga      3079
Ile Asn Ala Tyr Gly His Arg His Lys Leu Ile Lys Gly Val Glu Arg
            920                 925                 930

ctt atc tcc gga caa caa ggt ctt aac cca tat tta act ttg aac acc      3127
Leu Ile Ser Gly Gln Gln Gly Leu Asn Pro Tyr Leu Thr Leu Asn Thr
        935                 940                 945

tct ggt agt gga aca att ctt ata gat ctg tct cct gat gat aaa gag      3175
Ser Gly Ser Gly Thr Ile Leu Ile Asp Leu Ser Pro Asp Asp Lys Glu
    950                 955                 960

ttt cag tct gtg gag gaa gag atg caa agt aca gtt cga gag cac aga      3223
Phe Gln Ser Val Glu Glu Glu Met Gln Ser Thr Val Arg Glu His Arg
965                 970                 975                 980

gat gga ggt cat gca ggt gga atc ttc aac aga tac aat att ctc aag      3271
Asp Gly Gly His Ala Gly Gly Ile Phe Asn Arg Tyr Asn Ile Leu Lys
                985                 990                 995
```

-continued

```
att cag aag gtt  tgt aac aag aaa cta  tgg gaa aga tac act  cac      3316
Ile Gln Lys Val  Cys Asn Lys Lys Leu  Trp Glu Arg Tyr Thr  His
            1000                 1005                 1010

cgg aga aaa gaa  gtt tct gaa gaa aac  cac aac cat gcc aat  gaa      3361
Arg Arg Lys Glu  Val Ser Glu Glu Asn  His Asn His Ala Asn  Glu
            1015                 1020                 1025

cga atg cta ttt  cat ggg tct cct ttt  gtg aat gca att atc  cac      3406
Arg Met Leu Phe  His Gly Ser Pro Phe  Val Asn Ala Ile Ile  His
            1030                 1035                 1040

aaa ggc ttt gat  gaa agg cat gcg tac  ata ggt ggt atg ttt  gga      3451
Lys Gly Phe Asp  Glu Arg His Ala Tyr  Ile Gly Gly Met Phe  Gly
            1045                 1050                 1055

gct ggc att tat  ttt gct gaa aac tct  tcc aaa agc aat caa  tat      3496
Ala Gly Ile Tyr  Phe Ala Glu Asn Ser  Ser Lys Ser Asn Gln  Tyr
            1060                 1065                 1070

gta tat gga att  gga gga ggt act ggg  tgt cca gtt cac aaa  gac      3541
Val Tyr Gly Ile  Gly Gly Gly Thr Gly  Cys Pro Val His Lys  Asp
            1075                 1080                 1085

aga tct tgt tac  att tgc cac agg cag  ctg ctc ttt tgc cgg  gta      3586
Arg Ser Cys Tyr  Ile Cys His Arg Gln  Leu Leu Phe Cys Arg  Val
            1090                 1095                 1100

acc ttg gga aag  tct ttc ctg cag ttc  agt gca atg aaa atg  gca      3631
Thr Leu Gly Lys  Ser Phe Leu Gln Phe  Ser Ala Met Lys Met  Ala
            1105                 1110                 1115

cat tct cct cca  ggt cat cac tca gtc  act ggt agg ccc agt  gta      3676
His Ser Pro Pro  Gly His His Ser Val  Thr Gly Arg Pro Ser  Val
            1120                 1125                 1130

aat ggc cta gca  tta gct gaa tat gtt  att tac aga gga gaa  cag      3721
Asn Gly Leu Ala  Leu Ala Glu Tyr Val  Ile Tyr Arg Gly Glu  Gln
            1135                 1140                 1145

gct tat cct gag  tat tta att act tac  cag att atg agg cct  gaa      3766
Ala Tyr Pro Glu  Tyr Leu Ile Thr Tyr  Gln Ile Met Arg Pro  Glu
            1150                 1155                 1160

ggt atg gtc gat  gga taaatagtta ttttaagaaa ctaattccac tgaacctaaa    3821
Gly Met Val Asp  Gly
            1165

atcatcaaag cagcagtggc ctctacgttt tactcctttg ctgaaaaaaa atcatcttgc   3881

ccacaggcct gtggcaaaag gataaaaatg tgaacgaagt ttaacattct gacttgataa   3941

agctttaata atgtacagtg ttttctaaat atttcctgtt ttttcagcac tttaacagat   4001

gccattccag gttaaactgg gttgtctgta ctaaattata aacagagtta acttgaacct   4061

tttatatgtt atgcattgat tctaacaaac tgtaatgccc tcaacagaac taattttact   4121

aatacaatac tgtgttcttt aaaacacagc atttacactg aatacaattt catttgtaaa   4181

actgtaaata agagcttttg tactagccca gtatttattt acattgcttt gtaatataaa   4241

tctgttttag aactgcaaaa aaaaaaaaaa aaaa                               4275

<210> SEQ ID NO 6
<211> LENGTH: 1166
<212> TYPE: PRT
<213> ORGANISM: Homo sapiens

<400> SEQUENCE: 6

Met Ser Gly Arg Arg Cys Ala Gly Gly Gly Ala Ala Cys Ala Ser Ala
1               5                   10                  15

Ala Ala Glu Ala Val Glu Pro Ala Ala Arg Glu Leu Phe Glu Ala Cys
            20                  25                  30
```

-continued

```
Arg Asn Gly Asp Val Glu Arg Val Lys Arg Leu Val Thr Pro Glu Lys
        35                  40                  45

Val Asn Ser Arg Asp Thr Ala Gly Arg Lys Ser Thr Pro Leu His Phe
    50                  55                  60

Ala Ala Gly Phe Gly Arg Lys Asp Val Val Glu Tyr Leu Leu Gln Asn
65                  70                  75                  80

Gly Ala Asn Val Gln Ala Arg Asp Asp Gly Gly Leu Ile Pro Leu His
                85                  90                  95

Asn Ala Cys Ser Phe Gly His Ala Glu Val Val Asn Leu Leu Leu Arg
            100                 105                 110

His Gly Ala Asp Pro Asn Ala Arg Asp Asn Trp Asn Tyr Thr Pro Leu
        115                 120                 125

His Glu Ala Ala Ile Lys Gly Lys Ile Asp Val Cys Ile Val Leu Leu
    130                 135                 140

Gln His Gly Ala Glu Pro Thr Ile Arg Asn Thr Asp Gly Arg Thr Ala
145                 150                 155                 160

Leu Asp Leu Ala Asp Pro Ser Ala Lys Ala Val Leu Thr Gly Glu Tyr
                165                 170                 175

Lys Lys Asp Glu Leu Leu Glu Ser Ala Arg Ser Gly Asn Glu Glu Lys
            180                 185                 190

Met Met Ala Leu Leu Thr Pro Leu Asn Val Asn Cys His Ala Ser Asp
        195                 200                 205

Gly Arg Lys Ser Thr Pro Leu His Leu Ala Ala Gly Tyr Asn Arg Val
    210                 215                 220

Lys Ile Val Gln Leu Leu Leu Gln His Gly Ala Asp Val His Ala Lys
225                 230                 235                 240

Asp Lys Gly Asp Leu Val Pro Leu His Asn Ala Cys Ser Tyr Gly His
                245                 250                 255

Tyr Glu Val Thr Glu Leu Leu Val Lys His Gly Ala Cys Val Asn Ala
            260                 265                 270

Met Asp Leu Trp Gln Phe Thr Pro Leu His Glu Ala Ala Ser Lys Asn
        275                 280                 285

Arg Val Glu Val Cys Ser Leu Leu Leu Ser Tyr Gly Ala Asp Pro Thr
    290                 295                 300

Leu Leu Asn Cys His Asn Lys Ser Ala Ile Asp Leu Ala Pro Thr Pro
305                 310                 315                 320

Gln Leu Lys Glu Arg Leu Ala Tyr Glu Phe Lys Gly His Ser Leu Leu
                325                 330                 335

Gln Ala Ala Arg Glu Ala Asp Val Thr Arg Ile Lys Lys His Leu Ser
            340                 345                 350

Leu Glu Met Val Asn Phe Lys His Pro Gln Thr His Glu Thr Ala Leu
        355                 360                 365

His Cys Ala Ala Ala Ser Pro Tyr Pro Lys Arg Lys Gln Ile Cys Glu
    370                 375                 380

Leu Leu Leu Arg Lys Gly Ala Asn Ile Asn Glu Lys Thr Lys Glu Phe
385                 390                 395                 400

Leu Thr Pro Leu His Val Ala Ser Glu Lys Ala His Asn Asp Val Val
                405                 410                 415

Glu Val Val Val Lys His Glu Ala Lys Val Asn Ala Leu Asp Asn Leu
            420                 425                 430

Gly Gln Thr Ser Leu His Arg Ala Ala Tyr Cys Gly His Leu Gln Thr
        435                 440                 445

Cys Arg Leu Leu Leu Ser Tyr Gly Cys Asp Pro Asn Ile Ile Ser Leu
```

-continued

```
    450                 455                 460

Gln Gly Phe Thr Ala Leu Gln Met Gly Asn Glu Asn Val Gln Gln Leu
465                 470                 475                 480

Leu Gln Glu Gly Ile Ser Leu Gly Asn Ser Glu Ala Asp Arg Gln Leu
                485                 490                 495

Leu Glu Ala Ala Lys Ala Gly Asp Val Glu Thr Val Lys Lys Leu Cys
            500                 505                 510

Thr Val Gln Ser Val Asn Cys Arg Asp Ile Glu Gly Arg Gln Ser Thr
        515                 520                 525

Pro Leu His Phe Ala Ala Gly Tyr Asn Arg Val Ser Val Val Glu Tyr
    530                 535                 540

Leu Leu Gln His Gly Ala Asp Val His Ala Lys Asp Lys Gly Gly Leu
545                 550                 555                 560

Val Pro Leu His Asn Ala Cys Ser Tyr Gly His Tyr Glu Val Ala Glu
                565                 570                 575

Leu Leu Val Lys His Gly Ala Val Val Asn Val Ala Asp Leu Trp Lys
            580                 585                 590

Phe Thr Pro Leu His Glu Ala Ala Ala Lys Gly Lys Tyr Glu Ile Cys
        595                 600                 605

Lys Leu Leu Leu Gln His Gly Ala Asp Pro Thr Lys Lys Asn Arg Asp
    610                 615                 620

Gly Asn Thr Pro Leu Asp Leu Val Lys Asp Gly Asp Thr Asp Ile Gln
625                 630                 635                 640

Asp Leu Leu Arg Gly Asp Ala Ala Leu Leu Asp Ala Ala Lys Lys Gly
                645                 650                 655

Cys Leu Ala Arg Val Lys Lys Leu Ser Ser Pro Asp Asn Val Asn Cys
            660                 665                 670

Arg Asp Thr Gln Gly Arg His Ser Thr Pro Leu His Leu Ala Ala Gly
        675                 680                 685

Tyr Asn Asn Leu Glu Val Ala Glu Tyr Leu Leu Gln His Gly Ala Asp
    690                 695                 700

Val Asn Ala Gln Asp Lys Gly Gly Leu Ile Pro Leu His Asn Ala Ala
705                 710                 715                 720

Ser Tyr Gly His Val Asp Val Ala Ala Leu Leu Ile Lys Tyr Asn Ala
                725                 730                 735

Cys Val Asn Ala Thr Asp Lys Trp Ala Phe Thr Pro Leu His Glu Ala
            740                 745                 750

Ala Gln Lys Gly Arg Thr Gln Leu Cys Ala Leu Leu Leu Ala His Gly
        755                 760                 765

Ala Asp Pro Thr Leu Lys Asn Gln Glu Gly Gln Thr Pro Leu Asp Leu
    770                 775                 780

Val Ser Ala Asp Asp Val Ser Ala Leu Leu Thr Ala Ala Met Pro Pro
785                 790                 795                 800

Ser Ala Leu Pro Ser Cys Tyr Lys Pro Gln Val Leu Asn Gly Val Arg
                805                 810                 815

Ser Pro Gly Ala Thr Ala Asp Ala Leu Ser Ser Gly Pro Ser Ser Pro
            820                 825                 830

Ser Ser Leu Ser Ala Ala Ser Ser Leu Asp Asn Leu Ser Gly Ser Phe
        835                 840                 845

Ser Glu Leu Ser Ser Val Val Ser Ser Ser Gly Thr Glu Gly Ala Ser
    850                 855                 860

Ser Leu Glu Lys Lys Glu Val Pro Gly Val Asp Phe Ser Ile Thr Gln
865                 870                 875                 880
```

-continued

```
Phe Val Arg Asn Leu Gly Leu Glu His Leu Met Asp Ile Phe Glu Arg
                885                 890                 895

Glu Gln Ile Thr Leu Asp Val Leu Val Glu Met Gly His Lys Glu Leu
            900                 905                 910

Lys Glu Ile Gly Ile Asn Ala Tyr Gly His Arg His Lys Leu Ile Lys
        915                 920                 925

Gly Val Glu Arg Leu Ile Ser Gly Gln Gln Gly Leu Asn Pro Tyr Leu
    930                 935                 940

Thr Leu Asn Thr Ser Gly Ser Gly Thr Ile Leu Ile Asp Leu Ser Pro
945                 950                 955                 960

Asp Asp Lys Glu Phe Gln Ser Val Glu Glu Glu Met Gln Ser Thr Val
                965                 970                 975

Arg Glu His Arg Asp Gly Gly His Ala Gly Gly Ile Phe Asn Arg Tyr
            980                 985                 990

Asn Ile Leu Lys Ile Gln Lys Val  Cys Asn Lys Lys Leu  Trp Glu Arg
        995                 1000                1005

Tyr Thr  His Arg Arg Lys Glu  Val Ser Glu Glu Asn  His Asn His
    1010                1015                1020

Ala Asn  Glu Arg Met Leu Phe  His Gly Ser Pro Phe  Val Asn Ala
    1025                1030                1035

Ile Ile  His Lys Gly Phe Asp  Glu Arg His Ala Tyr  Ile Gly Gly
    1040                1045                1050

Met Phe  Gly Ala Gly Ile Tyr  Phe Ala Glu Asn Ser  Ser Lys Ser
    1055                1060                1065

Asn Gln  Tyr Val Tyr Gly Ile  Gly Gly Gly Thr Gly  Cys Pro Val
    1070                1075                1080

His Lys  Asp Arg Ser Cys Tyr  Ile Cys His Arg Gln  Leu Leu Phe
    1085                1090                1095

Cys Arg  Val Thr Leu Gly Lys  Ser Phe Leu Gln Phe  Ser Ala Met
    1100                1105                1110

Lys Met  Ala His Ser Pro Pro  Gly His His Ser Val  Thr Gly Arg
    1115                1120                1125

Pro Ser  Val Asn Gly Leu Ala  Leu Ala Glu Tyr Val  Ile Tyr Arg
    1130                1135                1140

Gly Glu  Gln Ala Tyr Pro Glu  Tyr Leu Ile Thr Tyr  Gln Ile Met
    1145                1150                1155

Arg Pro  Glu Gly Met Val Asp  Gly
    1160                1165
```

<210> SEQ ID NO 7
<211> LENGTH: 4134
<212> TYPE: DNA
<213> ORGANISM: Homo sapiens

<400> SEQUENCE: 7

```
cgaagatggc ggcgtcgcgt cgctctcagc atcatcacca ccatcatcaa caacagctcc     60

agcccgcccc aggggcttca gcgccgccgc cgccacctcc tcccccactc agccctggcc    120

tggccccggg gaccacccca gcctctccca cggccagcgg cctggccccc ttcgcctccc    180

cgcggcacgg cctagcgctg ccggaggggg atggcagtcg ggatccgccc gacaggcccc    240

gatccccgga cccggttgac ggtaccagct gttgcagtac caccagcaca atctgtaccg    300

tcgccgccgc tcccgtggtc ccagcggttt ctacttcatc tgccgctggg gtcgctccca    360

acccagccgg cagtggcagt aacaattcac cgtcgtcctc ttcttccccg acttcttcct    420
```

-continued

```
catcttcctc tccatcctcc cctggatcga gcttggcgga gagccccgag gcggccggag    480
ttagcagcac agcaccactg gggcctgggg cagcaggacc tgggacaggg gtcccagcag    540
tgagcggggc cctacgggaa ctgctggagg cctgtcgcaa tggggacgtg tcccgggtaa    600
agaggctggt ggacgcggca aacgtaaatg caaaggacat ggccggccgg aagtcttctc    660
ccctgcactt cgctgcaggt tttggaagga aggatgttgt agaacactta ctacagatgg    720
gtgctaatgt ccacgctcgt gatgatggag gtctcatccc gcttcataat gcctgttctt    780
ttggccatgc tgaggttgtg agtctgttat tgtgccaagg agctgatcca aatgccaggg    840
ataactggaa ctatacacct ctgcatgaag ctgctattaa agggaagatc gatgtgtgca    900
ttgtgctgct gcagcacgga gctgacccaa acattcggaa cactgatggg aaatcagccc    960
tggacctggc agatccttca gcaaaagctg tccttacagg tgaatacaag aaagacgaac   1020
tcctagaagc tgctaggagt ggtaatgaag aaaaactaat ggctttactg actcctctaa   1080
atgtgaattg ccatgcaagt gatgggcgaa agtcgactcc tttacatcta gcagcgggct   1140
acaacagagt tcgaatagtt cagcttcttc ttcagcatgg tgctgatgtt catgcaaaag   1200
acaaaggtgg acttgtgcct cttcataatg catgttcata tggacattat gaagtcacag   1260
aactgctact aaagcatgga gcttgtgtta atgccatgga tctctggcag tttactccac   1320
tgcacgaggc tgcttccaag aaccgtgtag aagtctgctc tttgttactt agccatggcg   1380
ctgatcctac gttagtcaac tgccatggca aaagtgctgt ggatatggct ccaactccgg   1440
agcttaggga gagattgact tatgaattta aaggtcattc tttactacaa gcagccagag   1500
aagcagactt agctaaagtt aaaaaaacac tcgctctgga aatcattaat ttcaaacaac   1560
cgcagtctca tgaaacagca ctgcactgtg ctgtggcctc tctgcatccc aaacgtaaac   1620
aagtgacaga attgttactt agaaaaggag caaatgttaa tgaaaaaaat aaagatttca   1680
tgactcccct gcatgttgca gccgaaagag cccataatga tgtcatggaa gttctgcata   1740
agcatggcgc caagatgaat gcactggaca cccttggtca gactgctttg catagagccg   1800
ccctagcagg ccacctgcag acctgccgcc tcctgctgag ttacggctct gacccctcca   1860
tcatctcctt acaaggcttc acagcagcac agatgggcaa tgaagcagtg cagcagattc   1920
tgagtgagag tacacctata cgtacttctg atgttgatta tcgactctta gaggcatcta   1980
aagctggaga cttggaaact gtgaagcaac tttgcagctc tcaaaatgtg aattgtagag   2040
acttagaggg ccggcattcc acgcccttac acttcgcagc aggctacaac cgcgtgtctg   2100
ttgtagagta cctgctacac cacggtgccg atgtccatgc caaagacaag ggtggcttgg   2160
tgccccttca taatgcctgt tcatatggac actatgaggt ggctgagctt ttagtaaggc   2220
atggggcttc tgtcaatgtg gcggacttat ggaaatttac ccctctccat gaagcagcag   2280
ctaaaggaaa gtatgaaatc tgcaagctcc ttttaaaaca tggagcagat ccaactaaaa   2340
agaacagaga tggaaataca cctttggatt tggtaaagga aggagacaca gatattcagg   2400
acttactgaa aggggatgct gctttgttgg atgctgccaa gaagggctgc ctggcaagag   2460
tgcagaagct ctgtacccca gagaatatca actgcagaga cacccagggc agaaattcaa   2520
cccctctgca cctggcagca ggctataata acctggaagt agctgaatat cttctagagc   2580
atggagctga tgttaatgcc caggacaagg gtggtttaat tcctcttcat aatgcggcat   2640
cttatgggca tgttgacata gcggctttat tgataaaata caacacgtgt gtaaatgcaa   2700
cagataagtg ggcgtttact cccctccatg aagcagccca gaaaggaagg acgcagctgt   2760
```

-continued

```
gcgccctcct cctagcgcat ggtgcagacc ccaccatgaa gaaccaggaa ggccagacgc   2820

ctctggatct ggcaacagct gacgatatca gagctttgct gatagatgcc atgcccccag   2880

aggccttacc tacctgtttt aaacctcagg ctactgtagt gagtgcctct ctgatctcac   2940

cagcatccac cccctcctgc ctctcggctg ccagcagcat agacaacctc actggccctt   3000

tagcagagtt ggccgtagga ggagcctcca atgcagggga tggcgccgcg ggaacagaaa   3060

ggaaggaagg agaagttgct ggtcttgaca tgaatatcag ccaatttcta aaaagccttg   3120

gccttgaaca ccttcgggat atctttgaaa cagaacagat tacactagat gtgttggctg   3180

atatgggtca tgaagagttg aaagaaatag gcatcaatgc atatgggcac cgccacaaat   3240

taatcaaagg agtagaaaga ctcttaggtg gacaacaagg caccaatcct tatttgactt   3300

ttcactgtgt taatcaggga acgattttgc tggatcttgc tccagaagat aaagaatatc   3360

agtcagtgga agaagagatg caaagtacta ttcgagaaca cagagatggt ggtaatgctg   3420

gcggcatctt caacagatac aatgtcattc gaattcaaaa agttgtcaac aagaagttga   3480

gggagcggtt ctgccaccga cagaaggaag tgtctgagga gaatcacaac catcacaatg   3540

agcgcatgtt gtttcatggt tctcctttca ttaatgccat tattcataaa gggtttgatg   3600

agcgacatgc atacatagga ggaatgtttg gggccgggat ttattttgct gaaaactcct   3660

caaaaagcaa ccaatatgtt tatggaattg gaggaggaac aggctgccct acacacaagg   3720

acaggtcatg ctatatatgt cacagacaaa tgctcttctg tagagtgacc cttgggaaat   3780

cctttctgca gtttagcacc atgaaaatgg cccacgcgcc tccagggcac cactcagtca   3840

ttggtagacc gagcgtcaat gggctggcat atgctgaata tgtcatctac agaggagaac   3900

aggcataccc agagtatctt atcacttacc agatcatgaa gccagaagcc ccttcccaga   3960

ccgcaacagc cgcagagcag aagacctagt gaatgcctgc tggtgaaggc cagatcagat   4020

ttcaacctgg gactggatta cagaggattg tttctaataa caacatcaat attctagaag   4080

tccctgacag cctagaaata agctgtttgt cttctataaa gcattgctat agtg         4134
```

```
<210> SEQ ID NO 8
<211> LENGTH: 1327
<212> TYPE: PRT
<213> ORGANISM: Homo sapiens

<400> SEQUENCE: 8

Met Ala Ala Ser Arg Arg Ser Gln His His His His His His Gln Gln
1               5                   10                  15

Gln Leu Gln Pro Ala Pro Gly Ala Ser Ala Pro Pro Pro Pro Pro Pro
            20                  25                  30

Pro Pro Leu Ser Pro Gly Leu Ala Pro Gly Thr Thr Pro Ala Ser Pro
        35                  40                  45

Thr Ala Ser Gly Leu Ala Pro Phe Ala Ser Pro Arg His Gly Leu Ala
    50                  55                  60

Leu Pro Glu Gly Asp Gly Ser Arg Asp Pro Pro Asp Arg Pro Arg Ser
65                  70                  75                  80

Pro Asp Pro Val Asp Gly Thr Ser Cys Cys Ser Thr Thr Ser Thr Ile
                85                  90                  95

Cys Thr Val Ala Ala Ala Pro Val Val Pro Ala Val Ser Thr Ser Ser
            100                 105                 110

Ala Ala Gly Val Ala Pro Asn Pro Ala Gly Ser Gly Ser Asn Asn Ser
        115                 120                 125

Pro Ser Ser Ser Ser Ser Pro Thr Ser Ser Ser Ser Ser Ser Pro Ser
```

-continued

```
    130                 135                 140

Ser Pro Gly Ser Ser Leu Ala Glu Ser Pro Glu Ala Ala Gly Val Ser
145                 150                 155                 160

Ser Thr Ala Pro Leu Gly Pro Gly Ala Ala Gly Pro Gly Thr Gly Val
                165                 170                 175

Pro Ala Val Ser Gly Ala Leu Arg Glu Leu Leu Glu Ala Cys Arg Asn
            180                 185                 190

Gly Asp Val Ser Arg Val Lys Arg Leu Val Asp Ala Ala Asn Val Asn
        195                 200                 205

Ala Lys Asp Met Ala Gly Arg Lys Ser Ser Pro Leu His Phe Ala Ala
    210                 215                 220

Gly Phe Gly Arg Lys Asp Val Val Glu His Leu Leu Gln Met Gly Ala
225                 230                 235                 240

Asn Val His Ala Arg Asp Asp Gly Gly Leu Ile Pro Leu His Asn Ala
                245                 250                 255

Cys Ser Phe Gly His Ala Glu Val Val Ser Leu Leu Leu Cys Gln Gly
            260                 265                 270

Ala Asp Pro Asn Ala Arg Asp Asn Trp Asn Tyr Thr Pro Leu His Glu
        275                 280                 285

Ala Ala Ile Lys Gly Lys Ile Asp Val Cys Ile Val Leu Leu Gln His
    290                 295                 300

Gly Ala Asp Pro Asn Ile Arg Asn Thr Asp Gly Lys Ser Ala Leu Asp
305                 310                 315                 320

Leu Ala Asp Pro Ser Ala Lys Ala Val Leu Thr Gly Glu Tyr Lys Lys
                325                 330                 335

Asp Glu Leu Leu Glu Ala Ala Arg Ser Gly Asn Glu Glu Lys Leu Met
            340                 345                 350

Ala Leu Leu Thr Pro Leu Asn Val Asn Cys His Ala Ser Asp Gly Arg
        355                 360                 365

Lys Ser Thr Pro Leu His Leu Ala Ala Gly Tyr Asn Arg Val Arg Ile
    370                 375                 380

Val Gln Leu Leu Leu Gln His Gly Ala Asp Val His Ala Lys Asp Lys
385                 390                 395                 400

Gly Gly Leu Val Pro Leu His Asn Ala Cys Ser Tyr Gly His Tyr Glu
                405                 410                 415

Val Thr Glu Leu Leu Leu Lys His Gly Ala Cys Val Asn Ala Met Asp
            420                 425                 430

Leu Trp Gln Phe Thr Pro Leu His Glu Ala Ala Ser Lys Asn Arg Val
        435                 440                 445

Glu Val Cys Ser Leu Leu Leu Ser His Gly Ala Asp Pro Thr Leu Val
    450                 455                 460

Asn Cys His Gly Lys Ser Ala Val Asp Met Ala Pro Thr Pro Glu Leu
465                 470                 475                 480

Arg Glu Arg Leu Thr Tyr Glu Phe Lys Gly His Ser Leu Leu Gln Ala
                485                 490                 495

Ala Arg Glu Ala Asp Leu Ala Lys Val Lys Lys Thr Leu Ala Leu Glu
            500                 505                 510

Ile Ile Asn Phe Lys Gln Pro Gln Ser His Glu Thr Ala Leu His Cys
        515                 520                 525

Ala Val Ala Ser Leu His Pro Lys Arg Lys Gln Val Thr Glu Leu Leu
    530                 535                 540

Leu Arg Lys Gly Ala Asn Val Asn Glu Lys Asn Lys Asp Phe Met Thr
545                 550                 555                 560
```

-continued

```
Pro Leu His Val Ala Ala Glu Arg Ala His Asn Asp Val Met Glu Val
                565                 570                 575

Leu His Lys His Gly Ala Lys Met Asn Ala Leu Asp Thr Leu Gly Gln
            580                 585                 590

Thr Ala Leu His Arg Ala Ala Leu Ala Gly His Leu Gln Thr Cys Arg
        595                 600                 605

Leu Leu Leu Ser Tyr Gly Ser Asp Pro Ser Ile Ile Ser Leu Gln Gly
    610                 615                 620

Phe Thr Ala Ala Gln Met Gly Asn Glu Ala Val Gln Gln Ile Leu Ser
625                 630                 635                 640

Glu Ser Thr Pro Ile Arg Thr Ser Asp Val Asp Tyr Arg Leu Leu Glu
                645                 650                 655

Ala Ser Lys Ala Gly Asp Leu Glu Thr Val Lys Gln Leu Cys Ser Ser
            660                 665                 670

Gln Asn Val Asn Cys Arg Asp Leu Glu Gly Arg His Ser Thr Pro Leu
        675                 680                 685

His Phe Ala Ala Gly Tyr Asn Arg Val Ser Val Val Glu Tyr Leu Leu
    690                 695                 700

His His Gly Ala Asp Val His Ala Lys Asp Lys Gly Gly Leu Val Pro
705                 710                 715                 720

Leu His Asn Ala Cys Ser Tyr Gly His Tyr Glu Val Ala Glu Leu Leu
                725                 730                 735

Val Arg His Gly Ala Ser Val Asn Val Ala Asp Leu Trp Lys Phe Thr
            740                 745                 750

Pro Leu His Glu Ala Ala Ala Lys Gly Lys Tyr Glu Ile Cys Lys Leu
        755                 760                 765

Leu Leu Lys His Gly Ala Asp Pro Thr Lys Lys Asn Arg Asp Gly Asn
    770                 775                 780

Thr Pro Leu Asp Leu Val Lys Glu Gly Asp Thr Asp Ile Gln Asp Leu
785                 790                 795                 800

Leu Lys Gly Asp Ala Ala Leu Leu Asp Ala Ala Lys Lys Gly Cys Leu
                805                 810                 815

Ala Arg Val Gln Lys Leu Cys Thr Pro Glu Asn Ile Asn Cys Arg Asp
            820                 825                 830

Thr Gln Gly Arg Asn Ser Thr Pro Leu His Leu Ala Ala Gly Tyr Asn
        835                 840                 845

Asn Leu Glu Val Ala Glu Tyr Leu Leu Glu His Gly Ala Asp Val Asn
    850                 855                 860

Ala Gln Asp Lys Gly Gly Leu Ile Pro Leu His Asn Ala Ala Ser Tyr
865                 870                 875                 880

Gly His Val Asp Ile Ala Ala Leu Leu Ile Lys Tyr Asn Thr Cys Val
                885                 890                 895

Asn Ala Thr Asp Lys Trp Ala Phe Thr Pro Leu His Glu Ala Ala Gln
            900                 905                 910

Lys Gly Arg Thr Gln Leu Cys Ala Leu Leu Leu Ala His Gly Ala Asp
        915                 920                 925

Pro Thr Met Lys Asn Gln Glu Gly Gln Thr Pro Leu Asp Leu Ala Thr
    930                 935                 940

Ala Asp Asp Ile Arg Ala Leu Leu Ile Asp Ala Met Pro Pro Glu Ala
945                 950                 955                 960

Leu Pro Thr Cys Phe Lys Pro Gln Ala Thr Val Val Ser Ala Ser Leu
                965                 970                 975
```

-continued

```
Ile Ser Pro Ala Ser Thr Pro Ser Cys Leu Ser Ala Ala Ser Ser Ile
            980                 985                 990

Asp Asn Leu Thr Gly Pro Leu Ala  Glu Leu Ala Val Gly  Gly Ala Ser
        995                 1000                1005

Asn Ala  Gly Asp Gly Ala Ala  Gly Thr Glu Arg Lys  Glu Gly Glu
    1010                 1015                 1020

Val Ala  Gly Leu Asp Met Asn  Ile Ser Gln Phe Leu  Lys Ser Leu
    1025                 1030                 1035

Gly Leu  Glu His Leu Arg Asp  Ile Phe Glu Thr Glu  Gln Ile Thr
    1040                 1045                 1050

Leu Asp  Val Leu Ala Asp Met  Gly His Glu Glu Leu  Lys Glu Ile
    1055                 1060                 1065

Gly Ile  Asn Ala Tyr Gly His  Arg His Lys Leu Ile  Lys Gly Val
    1070                 1075                 1080

Glu Arg  Leu Leu Gly Gly Gln  Gln Gly Thr Asn Pro  Tyr Leu Thr
    1085                 1090                 1095

Phe His  Cys Val Asn Gln Gly  Thr Ile Leu Leu Asp  Leu Ala Pro
    1100                 1105                 1110

Glu Asp  Lys Glu Tyr Gln Ser  Val Glu Glu Glu Met  Gln Ser Thr
    1115                 1120                 1125

Ile Arg  Glu His Arg Asp Gly  Gly Asn Ala Gly Gly  Ile Phe Asn
    1130                 1135                 1140

Arg Tyr  Asn Val Ile Arg Ile  Gln Lys Val Val Asn  Lys Lys Leu
    1145                 1150                 1155

Arg Glu  Arg Phe Cys His Arg  Gln Lys Glu Val Ser  Glu Glu Asn
    1160                 1165                 1170

His Asn  His His Asn Glu Arg  Met Leu Phe His Gly  Ser Pro Phe
    1175                 1180                 1185

Ile Asn  Ala Ile Ile His Lys  Gly Phe Asp Glu Arg  His Ala Tyr
    1190                 1195                 1200

Ile Gly  Gly Met Phe Gly Ala  Gly Ile Tyr Phe Ala  Glu Asn Ser
    1205                 1210                 1215

Ser Lys  Ser Asn Gln Tyr Val  Tyr Gly Ile Gly Gly  Gly Thr Gly
    1220                 1225                 1230

Cys Pro  Thr His Lys Asp Arg  Ser Cys Tyr Ile Cys  His Arg Gln
    1235                 1240                 1245

Met Leu  Phe Cys Arg Val Thr  Leu Gly Lys Ser Phe  Leu Gln Phe
    1250                 1255                 1260

Ser Thr  Met Lys Met Ala His  Ala Pro Pro Gly His  His Ser Val
    1265                 1270                 1275

Ile Gly  Arg Pro Ser Val Asn  Gly Leu Ala Tyr Ala  Glu Tyr Val
    1280                 1285                 1290

Ile Tyr  Arg Gly Glu Gln Ala  Tyr Pro Glu Tyr Leu  Ile Thr Tyr
    1295                 1300                 1305

Gln Ile  Met Lys Pro Glu Ala  Pro Ser Gln Thr Ala  Thr Ala Ala
    1310                 1315                 1320

Glu Gln  Lys Thr
    1325
```

<210> SEQ ID NO 9
<211> LENGTH: 384
<212> TYPE: DNA
<213> ORGANISM: Homo sapiens

<400> SEQUENCE: 9

-continued

```
tcgacagaca attgctggaa gctgcaaagg ctggagatgt cgaaactgta aaaaaactgt     60

gtactgttca gagtgtcaac tgcagagaca ttgaagggcg tcagtctaca ccacttcatt    120

ttgcagctgg gtataacaga gtgtccgtgg tggaatatct gctacagcat ggagctgatg    180

tgcatgctaa agataaagga ggccttgtac ctttgcacaa tgcatgttct tatggacatt    240

atgaagttgc agaacttctt gttaaacatg gagcagtagt taatgtagct gatttatgga    300

aatttacacc tttacatgaa gcagcagcaa aaggaaaata tgaaatttgc aaacttctgc    360

tccagcatgg tgcagaccct acaa                                           384


<210> SEQ ID NO 10
<211> LENGTH: 520
<212> TYPE: DNA
<213> ORGANISM: Homo sapiens

<400> SEQUENCE: 10

tttttttaac tgtggtgtgg gagccaagtc tatagcactt ttattgtgac aattgagcag     60

tgttgggtct gcaccataac ttaagagaag agaacatact tcaaccctgt tcttagaagc    120

tgcctcatga agaggagtga attgccacaa gtccattgca tttacacagg caccatgctt    180

gaccaaaagt tcagttactt cataatgacc ataagaacag gcattgtgta atggtaccag    240

atcaccttta tctttagcat ggacatcagc tccatgttgc agtaacagct gtacaatctt    300

tactctgtta tatcctgctg ccaaatgtaa tggagttgac tttctgccat cacttgcgtg    360

gcagttgaca tttaatggtg tgagtagagc catcattttt tcttcattgc cactcctggc    420

actttctaag agttcatctt tcttatattc accagtaagc actgctttgg cagatggatc    480

tgctaaatcc aatgctgtcc ttccatctgt atttcggatg                         520


<210> SEQ ID NO 11
<211> LENGTH: 22
<212> TYPE: DNA
<213> ORGANISM: Artificial Sequence
<220> FEATURE:
<223> OTHER INFORMATION: Primer
<221> NAME/KEY: misc_feature
<222> LOCATION: (1)..(22)
<223> OTHER INFORMATION:

<400> SEQUENCE: 11

tccagaggct ggtgacccct ga                                              22


<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12

ttgaactaac tactgaaga                                                  19


<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13

ctgtcttcag tagttagttc a                                               21
```

-continued

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
gttacaaacc ttctgaatct 20

<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15
gaaagataca ctcaccgga 19

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tagggttcag tgggaattag 20

<210> SEQ ID NO 17
<211> LENGTH: 18
<212> TYPE: DNA
<213> ORGANISM: Artificial Sequence
<220> FEATURE:
<223> OTHER INFORMATION: Primer

<400> SEQUENCE: 17
gactcctgga gcccgtca 18

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
ggtagcgacc gggcgtca 18

<210> SEQ ID NO 19
<211> LENGTH: 33
<212> TYPE: PRT
<213> ORGANISM: Artificial Sequence
<220> FEATURE:
<223> OTHER INFORMATION: Consensus
<221> NAME/KEY: MISC_FEATURE
<222> LOCATION: (1)..(1)
<223> OTHER INFORMATION: X can be any amino acid
<221> NAME/KEY: MISC_FEATURE
<222> LOCATION: (5)..(5)
<223> OTHER INFORMATION: Amino acid may be: Ala
<221> NAME/KEY: MISC_FEATURE
<222> LOCATION: (8)..(8)
<223> OTHER INFORMATION: Amino acid may be: Ile or Val
<221> NAME/KEY: MISC_FEATURE
<222> LOCATION: (10)..(10)

-continued

<223> OTHER INFORMATION: Amino acid may be: Ser
<221> NAME/KEY: MISC_FEATURE
<222> LOCATION: (11)..(11)
<223> OTHER INFORMATION: Amino acid may be: Gln or Lys
<221> NAME/KEY: MISC_FEATURE
<222> LOCATION: (13)..(13)
<223> OTHER INFORMATION: Amino acid may be: Asn
<221> NAME/KEY: MISC_FEATURE
<222> LOCATION: (14)..(14)
<223> OTHER INFORMATION: Amino acid may be: Asn
<221> NAME/KEY: MISC_FEATURE
<222> LOCATION: (15)..(15)
<223> OTHER INFORMATION: Amino acid may be: Leu or Thr
<221> NAME/KEY: MISC_FEATURE
<222> LOCATION: (16)..(16)
<223> OTHER INFORMATION: Amino acid may be: Asp
<221> NAME/KEY: MISC_FEATURE
<222> LOCATION: (17)..(17)
<223> OTHER INFORMATION: Amino acid may be: Ile or Met
<221> NAME/KEY: MISC_FEATURE
<222> LOCATION: (18)..(18)
<223> OTHER INFORMATION: Amino acid may be: Ala
<221> NAME/KEY: MISC_FEATURE
<222> LOCATION: (19)..(19)
<223> OTHER INFORMATION: Amino acid may be: Glu or Arg
<221> NAME/KEY: MISC_FEATURE
<222> LOCATION: (20)..(20)
<223> OTHER INFORMATION: Amino acid may be: Val
<221> NAME/KEY: MISC_FEATURE
<222> LOCATION: (23)..(23)
<223> OTHER INFORMATION: Amino acid may be: Lys or Gln or Glu
<221> NAME/KEY: MISC_FEATURE
<222> LOCATION: (27)..(27)
<223> OTHER INFORMATION: Amino acid may be: Asn or Ser
<221> NAME/KEY: MISC_FEATURE
<222> LOCATION: (28)..(28)
<223> OTHER INFORMATION: Amino acid may be: Pro or Ile
<221> NAME/KEY: MISC_FEATURE
<222> LOCATION: (29)..(29)
<223> OTHER INFORMATION: Amino acid may be: Asp
<221> NAME/KEY: MISC_FEATURE
<222> LOCATION: (32)..(32)
<223> OTHER INFORMATION: Amino acid may be: Asp or Asn
<221> NAME/KEY: MISC_FEATURE
<222> LOCATION: (3)..(3)
<223> OTHER INFORMATION: X can be any amino acid
<221> NAME/KEY: MISC_FEATURE
<222> LOCATION: (12)..(12)
<223> OTHER INFORMATION: X can be any amino acid
<221> NAME/KEY: MISC_FEATURE
<222> LOCATION: (24)..(24)
<223> OTHER INFORMATION: X can be any amino acid
<221> NAME/KEY: MISC_FEATURE
<222> LOCATION: (31)..(31)
<223> OTHER INFORMATION: X can be any amino acid

<400> SEQUENCE: 19

Xaa Gly Xaa Thr Pro Leu His Leu Ala Ala Arg Xaa Gly His Val Glu
1               5                   10                  15

Val Val Lys Leu Leu Leu Asp Xaa Gly Ala Asp Val Asn Ala Xaa Thr
            20                  25                  30

Lys

<210> SEQ ID NO 20
<211> LENGTH: 160
<212> TYPE: PRT
<213> ORGANISM: Homo sapiens

<400> SEQUENCE: 20

Glu Arg Tyr Thr His Arg Arg Lys Glu Val Ser Glu Glu Asn His Asn
1               5                   10                  15

His Ala Asn Glu Arg Met Leu Phe His Gly Ser Pro Phe Val Asn Ala
            20                  25                  30

-continued

```
Ile Ile His Lys Gly Phe Asp Glu Arg His Ala Tyr Ile Gly Gly Met
        35                  40                  45

Phe Gly Ala Gly Ile Tyr Phe Ala Glu Asn Ser Ser Lys Ser Asn Gln
    50                  55                  60

Tyr Val Tyr Gly Ile Gly Gly Gly Thr Gly Cys Pro Val His Lys Asp
65                  70                  75                  80

Arg Ser Cys Tyr Ile Cys His Arg Gln Leu Leu Phe Cys Arg Val Thr
                85                  90                  95

Leu Gly Lys Ser Phe Leu Gln Phe Ser Ala Met Lys Met Ala His Ser
            100                 105                 110

Pro Pro Gly His His Ser Val Thr Gly Arg Pro Ser Val Asn Gly Leu
        115                 120                 125

Ala Leu Ala Glu Tyr Val Ile Tyr Arg Gly Glu Gln Ala Tyr Pro Glu
    130                 135                 140

Tyr Leu Ile Thr Tyr Gln Ile Met Arg Pro Glu Gly Met Val Asp Gly
145                 150                 155                 160


<210> SEQ ID NO 21
<211> LENGTH: 22
<212> TYPE: PRT
<213> ORGANISM: Homo sapiens

<400> SEQUENCE: 21

Met Ser Gly Arg Arg Cys Ala Gly Gly Gly Ala Ala Cys Ala Ser Ala
1               5                   10                  15

Ala Ala Glu Ala Val Glu
            20


<210> SEQ ID NO 22
<211> LENGTH: 90
<212> TYPE: PRT
<213> ORGANISM: Homo sapiens

<400> SEQUENCE: 22

Thr Ala Ala Met Pro Pro Ser Ala Leu Pro Ser Cys Tyr Lys Pro Gln
1               5                   10                  15

Val Leu Asn Gly Val Arg Ser Pro Gly Ala Thr Ala Asp Ala Leu Ser
            20                  25                  30

Ser Gly Pro Ser Ser Pro Ser Ser Leu Ser Ala Ala Ser Ser Leu Asp
        35                  40                  45

Asn Leu Ser Gly Ser Phe Ser Glu Leu Ser Ser Val Val Ser Ser Ser
    50                  55                  60

Gly Thr Glu Gly Ala Ser Ser Leu Glu Lys Lys Glu Val Pro Gly Val
65                  70                  75                  80

Asp Phe Ser Ile Thr Gln Phe Val Arg Asn
                85                  90


<210> SEQ ID NO 23
<211> LENGTH: 8
<212> TYPE: PRT
<213> ORGANISM: Homo sapiens

<400> SEQUENCE: 23

Arg Pro Glu Gly Met Val Asp Gly
1               5


<210> SEQ ID NO 24
<211> LENGTH: 20
```

-continued

<212> TYPE: DNA
<213> ORGANISM: Artificial Sequence
<220> FEATURE:
<223> OTHER INFORMATION: Primer

<400> SEQUENCE: 24
gttacatttg ccacaggcag 20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
gtctttcttg cagttcagtg 20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
gagtcgagag acttatctcc 20

<210> SEQ ID NO 27
<211> LENGTH: 19
<212> TYPE: DNA
<213> ORGANISM: Artificial Sequence
<220> FEATURE:
<223> OTHER INFORMATION: Primer

<400> SEQUENCE: 27
gagcacagag atggaggtc 19

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
atgtacagca actcctccaa ga 22

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
cagacaattg ctggaagctg 20

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30

-continued cagacaattg ctggaagctg c 21

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
ctactcctga gctatgggtg 20

<210> SEQ ID NO 32
<211> LENGTH: 22
<212> TYPE: DNA
<213> ORGANISM: Artificial Sequence
<220> FEATURE:
<223> OTHER INFORMATION: Primer

<400> SEQUENCE: 32
gtgtactgtt cagagtgtca ac 22

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
ccatgctgga gcagaagttt g 21

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
gctaaaatct ctcctggaac c 21

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
gtttgtgcct atgtccataa gc 22

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
caaaagagca gctgcctgtg 20

<210> SEQ ID NO 37
<211> LENGTH: 22
<212> TYPE: DNA
<213> ORGANISM: Artificial Sequence -continued
<220> FEATURE:
<223> OTHER INFORMATION: Primer

<400> SEQUENCE: 37
ctgcaggaaa gactttccca ag 22

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
gcagccagtg gccctctacg 20

<210> SEQ ID NO 39
<211> LENGTH: 19
<212> TYPE: DNA
<213> ORGANISM: Artificial Sequence
<220> FEATURE:
<223> OTHER INFORMATION: Primer

<400> SEQUENCE: 39
gccccacagg cctgtggcc 19

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
gaaactaatt cccactaacc 20

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
aataaatact gggctagtac 20

<210> SEQ ID NO 42
<211> LENGTH: 22
<212> TYPE: DNA
<213> ORGANISM: Artificial Sequence
<220> FEATURE:
<223> OTHER INFORMATION: Primer

<400> SEQUENCE: 42
agggtctgca ccatgctgga gc 22

<210> SEQ ID NO 43
<211> LENGTH: 22
<212> TYPE: DNA
<213> ORGANISM: Artificial Sequence
<220> FEATURE:
<223> OTHER INFORMATION: Primer

<400> SEQUENCE: 43
ataaatcagc tacattaact ac 22

-continued

<210> SEQ ID NO 44
<211> LENGTH: 19
<212> TYPE: DNA
<213> ORGANISM: Artificial Sequence
<220> FEATURE:
<223> OTHER INFORMATION: Primer

<400> SEQUENCE: 44
cccagctgca aaatgaagt 19

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
aatgactctg cagttgacac 20

<210> SEQ ID NO 46
<211> LENGTH: 21
<212> TYPE: DNA
<213> ORGANISM: Artificial Sequence
<220> FEATURE:
<223> OTHER INFORMATION: Primer

<400> SEQUENCE: 46
gatacactca ccggagaaaa g 21

<210> SEQ ID NO 47
<211> LENGTH: 21
<212> TYPE: DNA
<213> ORGANISM: Artificial Sequence
<220> FEATURE:
<223> OTHER INFORMATION: Primer

<400> SEQUENCE: 47
gtgaactgga cacccagtac c 21

<210> SEQ ID NO 48
<211> LENGTH: 22
<212> TYPE: DNA
<213> ORGANISM: Artificial Sequence
<220> FEATURE:
<223> OTHER INFORMATION: Primer

<400> SEQUENCE: 48
ggtatggtcg atggataaat ag 22

<210> SEQ ID NO 49
<211> LENGTH: 19
<212> TYPE: DNA
<213> ORGANISM: Artificial Sequence
<220> FEATURE:
<223> OTHER INFORMATION: Primer

<400> SEQUENCE: 49
gaacacagta ttgtattag 19

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
cggcgggcag gaaatccacc 20

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
ttggggtctg caccatgtcg 20

<210> SEQ ID NO 52
<211> LENGTH: 22
<212> TYPE: DNA
<213> ORGANISM: Artificial Sequence
<220> FEATURE:
<223> OTHER INFORMATION: Primer

<400> SEQUENCE: 52
tccagaggct ggtgacccct ga 22

<210> SEQ ID NO 53
<211> LENGTH: 22
<212> TYPE: DNA
<213> ORGANISM: Artificial Sequence
<220> FEATURE:
<223> OTHER INFORMATION: Primer

<400> SEQUENCE: 53
tctgctaaat ccaatgctgt cc 22

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
tgcagcgggg tggatttcct 20

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
cattttgaag caaatattta 20

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
ggaataaggc ccccattata 20

<210> SEQ ID NO 57

-continued

<211> LENGTH: 20
<212> TYPE: DNA
<213> ORGANISM: Artificial Sequence
<220> FEATURE:
<223> OTHER INFORMATION: Primer

<400> SEQUENCE: 57
cattttgaag caaatattta 20

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
ggaataaggc ccccattata 20

<210> SEQ ID NO 59
<211> LENGTH: 34
<212> TYPE: DNA
<213> ORGANISM: Artificial Sequence
<220> FEATURE:
<223> OTHER INFORMATION: Primer

<400> SEQUENCE: 59
atcgatgcca gccatggagg ttccaggagt agat 34

<210> SEQ ID NO 60
<211> LENGTH: 26
<212> TYPE: DNA
<213> ORGANISM: Artificial Sequence
<220> FEATURE:
<223> OTHER INFORMATION: Primer

<400> SEQUENCE: 60
gctctagatc aggcctcata atctgg 26

<210> SEQ ID NO 61
<211> LENGTH: 9
<212> TYPE: PRT
<213> ORGANISM: Homo sapiens

<400> SEQUENCE: 61

Met Ala Ala Ser Arg Arg Ser Gln Cys
1 5

<210> SEQ ID NO 62
<211> LENGTH: 9
<212> TYPE: PRT
<213> ORGANISM: Homo sapiens

<400> SEQUENCE: 62

Met Ser Gly Arg Arg Cys Ala Gly Lys
1 5

<210> SEQ ID NO 63
<211> LENGTH: 15
<212> TYPE: PRT
<213> ORGANISM: Homo sapiens

<400> SEQUENCE: 63

Gln Glu Gly Ile Ser Leu Gly Asn Ser Glu Ala Asp Arg Gln Cys
1 5 10 15

-continued

```
<210> SEQ ID NO 64
<211> LENGTH: 11
<212> TYPE: PRT
<213> ORGANISM: Homo sapiens

<400> SEQUENCE: 64

Gly Glu Tyr Lys Lys Asp Glu Leu Leu Glu Cys
1               5                   10
```